(12) United States Patent
Nishikawa et al.

(10) Patent No.: US 7,364,670 B2
(45) Date of Patent: Apr. 29, 2008

(54) LIQUID CRYSTALLINE COMPOUND, LIQUID CRYSTALLINE COMPOSITION AND RETARDATION FILM

(75) Inventors: Hideyuki Nishikawa, Kanagawa (JP); Atsuhiro Ohkawa, Kanagawa (JP)

(73) Assignee: Fujifilm Corporation, Minato-Ku, Tokyo (JP)

( * ) Notice: Subject to any disclaimer, the term of this patent is extended or adjusted under 35 U.S.C. 154(b) by 360 days.

(21) Appl. No.: 10/892,297

(22) Filed: Jul. 16, 2004

(65) Prior Publication Data

US 2005/0056811 A1   Mar. 17, 2005

(30) Foreign Application Priority Data

Jul. 17, 2003 (JP) .................. P. 2003-276042
Sep. 24, 2003 (JP) .................. P. 2003-330969
Apr. 30, 2004 (JP) .................. P. 2004-135438

(51) Int. Cl.
C09K 19/34 (2006.01)
C09K 19/52 (2006.01)
G02B 5/30 (2006.01)

(52) U.S. Cl. .................. 252/299.01; 252/299.61; 428/1.1; 428/1.31

(58) Field of Classification Search .......... 252/299.01, 252/299.67, 299.61, 299.63; 349/117; 428/1.31, 428/1.1
See application file for complete search history.

(56) References Cited

U.S. PATENT DOCUMENTS 6,139,771 A * 10/2000 Walba et al. .......... 252/299.01

2003/0039770 A1   2/2003  Sato et al.
2003/0044518 A1 *  3/2003  Senoo et al. .................. 427/66
2004/0201797 A1 * 10/2004  Wu et al. ..................... 349/96

FOREIGN PATENT DOCUMENTS

EP   0 928 984 A2   7/1999
EP   1 156 349 A1  11/2001
EP   1 295 866 A1   3/2003

OTHER PUBLICATIONS

Caplus 2001: 760118.*
Bong Gi Kim et al., "Star-Shaped Discotic Nematic Liquid Crystal Containing 1,3,5-Triethynylbenzene and Oxadiazole-Based Rigid Arms", Tetrahedron Letters, Elsevier Science Publishers, vol. 42, No. 14, Apr. 2, 2001, pp. 2697-2699.
Frederic Cherioux, "Synthesis and Characterisation of a Octupolar Polymer and New Molecular Octupoles with Off-Resonant Third Order Optical Nonlinearities", Chemical Communications, vol. 20, 1999, pp. 2083-2084.
European Patent Office Search Report.

* cited by examiner

Primary Examiner—Shean C Wu
(74) Attorney, Agent, or Firm—Buchanan Ingersoll & Rooney PC

(57) ABSTRACT

To provide a liquid crystalline composition, which can be obtained by mixing a plurality of liquid crystalline compositions each of which can exhibit different liquid crystal phases from one another, being capable of exhibiting a biaxial liquid crystal phase, a liquid crystalline composition contains a liquid crystalline composition R which exhibits a liquid crystal phase having a positive birefringence; and a liquid crystalline composition D which exhibits a liquid crystal phase having a negative birefringence, in which the liquid crystalline composition R comprises a compound having a rectangular plate-like shape.

18 Claims, No Drawings

LIQUID CRYSTALLINE COMPOUND, LIQUID CRYSTALLINE COMPOSITION AND RETARDATION FILM

BACKGROUND OF THE INVENTION

1. Field of the Invention

The present invention relates to a liquid crystalline composition extremely useful in preparation of a retardation film and the like and, particularly, to a liquid crystalline composition which exhibits a biaxial liquid crystal phase. Further, the present invention relates to a retardation film having an optically anisotropic layer formed from the liquid crystalline composition and an elliptically polarizing film.

2. Background Art

An optical biaxial film having controlled refractive indices in three axial directions is useful in an optical art field in which polarization is utilized. Particularly, in the field of a liquid crystal display art, since polarization can be finely controlled with the biaxial film, an importance of such film is high. When such optical biaxial film as described above is prepared, it is an ordinary method that the biaxial film is prepared by biaxially drawing a film obtained from a polymer (for example, see JP-A No.2-264905). When the biaxial film is prepared by the biaxial drawing, since refractive indices in three axial directions can be controlled by a draw ratio, they can comparatively easily be controlled to be of desired refractive indices.

Since the biaxial film using a biaxial liquid crystal has a merit such that a film thickness thereof can be extremely thin, compared with a biaxially drawn film which has been used in many cases, it is a useful measure for aiming for reducing thickness of a layer, weight or the like of a device to use the biaxial liquid crystal in the biaxial film. Further, a film prepared by the drawing has a problem in that it is inferior in dimensional stability and an optical property thereof is liable to be changed by moisture, heat and the like. By using a polymerizable biaxial liquid crystal, such problems as described above may possibly be solved.

However, when the biaxial film is prepared by using the biaxial liquid crystal, it is a problem that refractive indices in three axial directions can not arbitrarily be controlled. This is because the refractive indices in three directions of the biaxial film using a biaxial liquid crystal are determined nearly uniquely by the refractive indices in three directions of a compound (biaxial liquid crystalline compound) which exhibits a biaxial liquid crystal phase. Namely, in order to allow the refractive indices in three directions of the biaxial film to be desired refractive indices, there have not been other measures than synthesizing a biaxial liquid crystalline compound having the desired refractive indices. However, since the number of biaxial liquid crystalline compounds is small compared with a compound which exhibits a uniaxial liquid crystal phase (uniaxial liquid crystalline compound), it was extremely difficult to arbitrarily control the refractive indices in three directions.

In order to avoid such problems as described above, a proposal in which a biaxial liquid crystal phase is exhibited by mixing a rod-like liquid crystal and a discotic liquid crystal are mixed with each other has been made (for example, see Y. Rabin, *Mol. Cry. Liq. Cry.*, Vol. 89, p. 67 (1982)). In such method as described above, since the refractive indices in three directions can be controlled by changing a mixing ratio of the rod-like liquid crystal to the discotic liquid crystal, the method is extremely convenient. At the proposal, many trials for exhibiting the biaxial liquid crystal phase by mixing the rod-like liquid crystal and the discotic liquid crystal have been performed (for example, see R. Pratiba and N. V. Madhususana, *Mol. Cry. Liq. Cry.*, Vol. 1, p. 111 (1985)). However, since the compatibility of the rod-like liquid crystal and the discotic liquid crystal was not favorable, there were problems in that, in the mixing of the two liquid crystal, crystallinity was disappeared or two types of liquid crystal phases caused a phase separation. Accordingly, in such mixing system as described above, the biaxial liquid crystal phase was not allowed to be exhibited.

SUMMARY OF THE INVENTION

Under these circumstances, an object of the present invention is to provide a liquid crystalline composition, which can be obtained by mixing a plurality of liquid crystalline compositions each of which can exhibit different liquid crystal phases from one another, being capable of exhibiting a biaxial liquid crystal phase. Further, another object of the present invention is to provide a novel liquid crystalline compound useful in exhibiting a biaxial liquid crystal phase by being mixed with any one of other liquid crystalline compositions and a liquid crystalline composition thereof. Furthermore, still another object of the present invention is to provide a retardation film using these liquid crystalline compositions.

The aforementioned objects can be solved by the following techniques:

(1) A liquid crystalline composition, which comprises:
a liquid crystalline composition R which exhibits a liquid crystal phase having a positive birefringence; and
a liquid crystalline composition D which exhibits a liquid crystal phase having a negative birefringence,
wherein the liquid crystalline composition R comprises a compound having a rectangular plate-like shape.

(2) A liquid crystalline composition, which comprises:
a liquid crystalline composition R which exhibits a liquid crystal phase having a positive birefringence; and
a liquid crystalline composition D which exhibits a liquid crystal phase having a negative birefringence,
wherein the liquid crystalline composition D comprises a compound represented by the following formula (D-2):

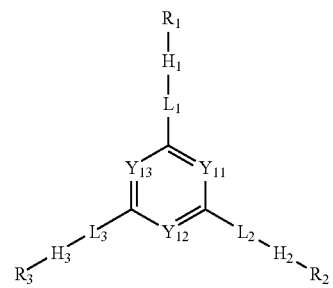

wherein $Y_{11}$, $Y_{12}$ and $Y_{13}$ each independently represent a methine group or a nitrogen atom;

$H_1$, $H_2$ and $H_3$ each independently represent a divalent 5-membered cyclic group;

$L_1$, $L_2$ and $L_3$ each independently represent a single bond or a divalent linking group;

$R_1$, $R_2$ and $R_3$ each independently represent an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, an alkylsulfonylamino group, an arylsulfonylamino group, a sulfamoyl group, a carbamoyl group, an alkylthio group, an arylthio group, an alkylsulfonyl group, an arylsulfonyl group, an alkylsulfinyl group, an arylsulfinyl group, an ureido group, a phosphoric acid amido group, a hydroxyl group, a mercapto group, a halogen atom, a cyano group, a sulfo group, a carboxyl group, a nitro group, a hydroxamic acid group, a sulfino group, a hydrazino group, an imino group, a heterocyclic group or a silyl group.

(3) The liquid crystalline composition according to item (2), wherein the formula (D-2) is represented by the following formula (I):

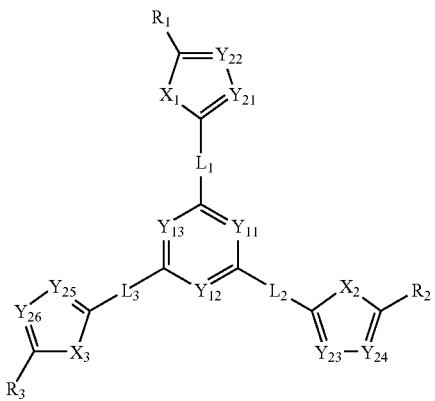

wherein $Y_{11}$, $Y_{12}$, $Y_{13}$, $L_1$, $L_2$, $L_3$, $R_1$, $R_2$ and $R_3$ are identical to those as defined in the formula (D-2);

$Y_{21}$, $Y_{22}$, $Y_{23}$, $Y_{24}$, $Y_{25}$ and $Y_{26}$ each independently represent a methine group or a nitrogen atom;

$X_1$, $X_2$ and $X_3$ each independently represent an oxygen atom, a sulfur atom, a methylene group or an imino group.

(4) The liquid crystalline composition according to item (2) or (3), wherein the liquid crystalline composition R comprises a liquid crystalline compound having a rectangular plate-like shape.

(5) The liquid crystalline composition according to item (1) or (4), wherein the compound having the rectangular plate-like shape has at least two core moieties each of which has liquid crystallinity, the at least two core moieties being linked by at least one covalent bond to form the rectangular plate-like shape.

(6) The liquid crystalline composition according to item (1) or (4), wherein the compound having the rectangular plate-like shape is a liquid crystalline compound represented by the following formula (R-I):

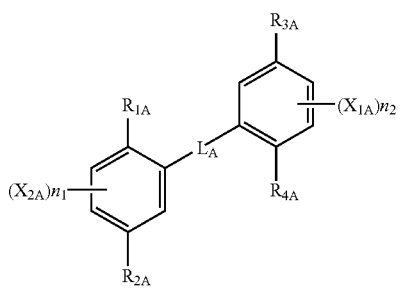

wherein $L_A$ represents —═— or —═—═—;

$X_{1A}$ and $X_{2A}$ each independently represent a halogen atom, a carboxyl group, a hydroxyl group, a cyano group, a nitro group, an alkyl group or an alkyloxy group;

$n_1$ and $n_2$ each independently represent an integer of from 0 to 3; and $R_{1A}$, $R_{2A}$, $R_{3A}$ and $R_{4A}$ are each independently represented by the following formula (R-IA):

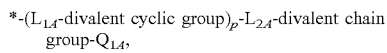

*-($L_{1A}$-divalent cyclic group)$_p$-$L_{2A}$-divalent chain group-$Q_{1A}$, wherein * denotes a position to be bonded to the benzene ring in the formula (R-I);

$L_{1A}$ and $L_{2A}$ each independently represent a single bond or a divalent linking group;

the divalent cyclic group is a divalent linking group having at least one cyclic structure;

the divalent chain group is an alkylene group, a substituted alkylene group, an alkenylene group, a substituted alkenylene group, an alkynylene group or a substituted alkynylene group, wherein the —CH$_2$— group in the alkylene group and the substituted alkylene group may be substituted with one of —O— or —S—, and when the alkenylene group, the substituted alkenylene group, the alkynylene group or the substituted alkynylene group contains —CH$_2$— group, the —CH$_2$— group may be substituted with one of —O— or —S—;

$Q_{1A}$ represents a polymerizable group; and p represents an integer of from 0 to 3.

(7) A liquid crystalline composition, which comprises:
a liquid crystalline composition R which exhibits a liquid crystal phase having a positive birefringence; and
a liquid crystalline composition D which exhibits a liquid crystal phase having a negative birefringence,
wherein the liquid crystalline composition exhibits a liquid crystal phase in a mixed state of the liquid crystalline composition R and the liquid crystalline composition D, at any mixing ratio of the liquid crystalline composition R to the liquid crystalline composition D.

(8) The liquid crystalline composition according to any one of items (1) to (7), wherein the liquid crystal phase having the positive birefringence is a nematic phase.

(9) The liquid crystalline composition according to any one of items (1) to (8), wherein the liquid crystal phase having the negative birefringence is a discotic nematic phase.

(10) The liquid crystalline composition according to any one of items (1) to (9), which exhibits a liquid crystal phase at a temperature of from 20° C. to 300° C.

(11) The liquid crystalline composition according to any one of items (1) to (10), which exhibits a liquid crystal phase satisfying the following numerical formula (III):

$$1.1 \leq (nx-nz)/(nx-ny) \leq 20,$$

wherein nx, ny and nz represent refractive indices in three perpendicular directions to each other in the liquid crystal phase, while nx denotes a largest refractive index and nz denotes a smallest refractive index.

(12) A retardation film comprising: a transparent support; and at least one optically anisotropic layer formed from a liquid crystalline composition according to any one of items (1) to (11).

(13) An elliptically polarizing film comprising: a retardation film according to item (12) and a polarizing film.

(14) A liquid crystalline compound represented by the following formula (II):

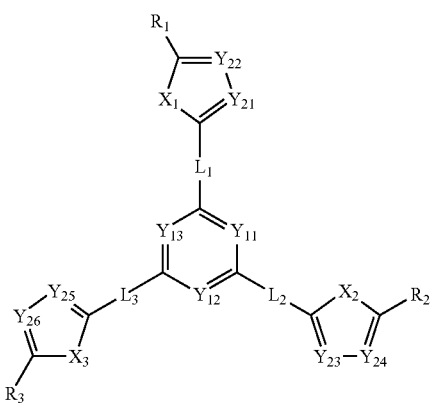

wherein $Y_{11}$, $Y_{12}$, $Y_{13}$, $Y_{21}$, $Y_{22}$, $Y_{23}$, $Y_{24}$, $Y_{25}$ and $Y_{26}$ each independently represent a methine group or a nitrogen atom;

$X_1$, $X_2$ and $X_3$ each independently represent an oxygen atom, a sulfur atom, a methylene group or an imino group;

$L_1$, $L_2$ and $L_3$ each independently represent a single bond or a divalent linking group;

$R_1$, $R_2$ and $R_3$ each independently represent the following formula (V):

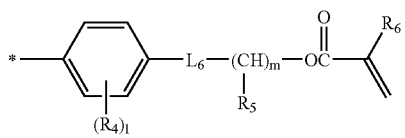

wherein * denotes a position to be bonded to the 5-membered ring in the formula (II);

$R_4$ represents a halogen atom, an alkyl group having from 1 to 8 carbon atoms, an alkyloxy group having from 2 to 8 carbon atoms, an alkoxycarbonyl group having from 2 to 8 carbon atoms, a nitro group or a cyano group;

l represents an integer of from 0 to 4;

$L_6$ represents at least one group selected from the group consisting of —O—, —CO—O, —O—CO—, —O—CO—O and —CH$_2$—, wherein  denotes a position to be bonded to the benzene ring in the formula (V);

$R_5$ represents a hydrogen atom, a methyl group, an ethyl group or a propyl group;

m represents an integer of from 2 to 16; and $R_6$ represents a hydrogen atom or a methyl group.

(15) A liquid crystalline compound represented by the following formula (R-I):

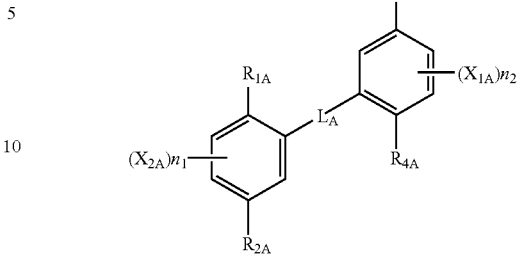

wherein $L_A$ represents 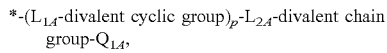;

$X_{1A}$ and $X_{2A}$ each independently represent a halogen atom, a carboxyl group, a hydroxyl group, a cyano group, a nitro group, an alkyl group or an alkyloxy group;

$n_1$ and $n_2$ each independently represent an integer of from 0 to 3; and $R_{1A}$, $R_{2A}$, $R_{3A}$ and $R_{4A}$ are each independently represented by the following formula (R-IA):

*-($L_{1A}$-divalent cyclic group)$_p$-$L_{2A}$-divalent chain group-$Q_{1A}$, wherein * denotes a position to be bonded to the benzene ring in the formula (R-I);

$L_{1A}$ and $L_{2A}$ each independently represent a single bond or a divalent linking group;

the divalent cyclic group is a divalent linking group having at least one cyclic structure;

the divalent chain group is an alkylene group, a substituted alkylene group, an alkenylene group, a substituted alkenylene group, an alkynylene group or a substituted alkynylene group, wherein the —CH$_2$— group in the alkylene group and the substituted alkylene group may be substituted with one of —O— or —S—, and when the alkenylene group, the substituted alkenylene group, the alkynylene group or the substituted alkynylene group contains —CH$_2$— group, the —CH$_2$— group may be substituted with one of —O— or —S—;

$Q_{1A}$ represents a polymerizable group; and p represents an integer of from 0 to 3.

The present invention can provide a liquid crystalline composition which can exhibit a biaxial liquid crystal phase, by mixing a plurality of liquid crystalline compositions which exhibit different liquid crystal phases from one another. A liquid crystalline composition exhibiting a biaxial liquid crystal phase can be obtained by mixing, as liquid crystalline compositions which exhibit liquid crystal phases different from each other, a liquid crystalline composition which exhibits a liquid crystal phase having a positive birefringence and a liquid crystalline composition which exhibits a liquid crystal phase having a negative birefringence. Further, refractive indices in three axial directions of the liquid crystal phase which the obtained liquid crystalline composition exhibits can be controlled by a mixing ratio of the liquid crystalline composition which exhibits a liquid crystal phase having a positive birefringence to the liquid crystalline composition which exhibits a liquid crystal phase having a negative birefringence.

Still further, the present invention can provide a retardation film having an optically anisotropic layer formed from these liquid crystalline compositions and in which a refractive index is controlled in a desired value. By using the retardation film, an elliptically polarizing film which can finely control polarization and a liquid crystal display device having a wide viewing angle can be provided.

DETAILED DESCRIPTION OF THE INVENTION

A liquid crystalline composition according to the present invention exhibits a biaxial liquid crystal phase by mixing a liquid crystal line composition R which exhibits (or expresses) a liquid crystal phase having a positive birefringence and a liquid crystal line composition D which exhibits a liquid crystal phase having a negative birefringence.

On this occasion, the liquid crystal phase having the positive birefringence is a liquid crystal phase which satisfies the following numerical formula (I), while the liquid crystal phase having the negative birefringence is a liquid crystal phase which satisfies the following numerical formula (II):

$$1.0 \leq (nx-nz)/(nx-ny) < 1.1 \qquad (I),$$

$$20 < (nx-nz)/(nx-ny) \leq \infty \qquad (II),$$

wherein nx, ny and nz represent refractive indices in three perpendicular directions in an individual liquid crystal phase exhibited by each of the liquid crystalline composition R and the liquid crystalline composition D, while, in the individual liquid crystal phase, nx denotes a largest refractive index and nz denotes a smallest refractive index.

As for a method for obtaining the refractive indices in three directions of the liquid crystal phase, for example, Sakai, "Birefringence analysis method of film by utilizing automatic birefringence meter", *Plastics*, Vol. 51, No. 3, 57 (2000) can be of reference.

The liquid crystalline composition R and the liquid crystalline composition D according to the present invention are each a liquid crystalline composition comprising at least one kind of liquid crystalline compound. When in a case in which the liquid crystalline composition comprises two kinds of liquid crystalline compounds, a polymerizable liquid crystalline compound and a non-polymerizable liquid crystalline compound can simultaneously be used. Further, a low molecular weight liquid crystalline compound and a polymer liquid crystalline compound can simultaneously be used.

Still further, other than liquid crystalline compounds, the liquid crystalline composition may contain an additive (for example, an air interface alignment controlling agent, an anti-shedding agent, a polymerization initiator, a polymerizable monomer and a solvent), which may be added into the liquid crystalline composition at the time of forming an optically anisotropic layer as described below. These additives may be added at the time of forming the liquid crystalline composition according to the present invention by mixing the liquid crystalline composition R and the liquid crystalline composition D.

(Liquid Crystalline Composition R Exhibiting Liquid Crystal Phase Satisfying Numerical Formula (I))

As for liquid crystal phases which satisfy the numerical formula (I), for example, a nematic phase, a smectic A phase or a smectic C phase can be mentioned. Since these liquid crystal phases each satisfy a relationship of nx>ny=nz, they are each a uniaxial liquid crystal phase having a positive birefringence. A detail thereof is described in, for example, *Ekisho Binraun* (*Liquid Crystal Handbook*), Chapter 2 (Maruzen, published in 2000) and, according to the present invention, as for the liquid crystal phase which satisfies the numerical formula (I), the nematic phase is particularly preferred.

The liquid crystal phase which is difficult to be judged whether it belongs to a uniaxial liquid crystal phase or a biaxial liquid crystal phase has been known. For example, the liquid crystal phase described in D. Demus and J. Goodby, "*Handbook of Liquid Crystal*", Vol. 2B: Low Molecular Weight Liquid Crystals II, pp. 933 to 943, published by WILEY-VCH can be said to be a liquid crystal phase which is difficult to be judged. As for the liquid crystal phase which satisfies the numerical formula (I), such liquid crystal phase which is difficult to be judged whether it is uniaxial or biaxial as described above is included (in this case, (nx–nz)/(nx–ny) is not equal to 1).

A judgment as to whether the liquid crystal phase is uniaxial or biaxial and a judgment as to whether the birefringence is positive or negative can be performed through a conoscope observation of a liquid crystalline composition in homeotropic alignment by using a polarization microscope. These judgments can be performed in accordance with a reference described in Seitaro Tsuboi, "*Polarization Microscope*", Chapter 3, Iwanami (1959).

The liquid crystalline compound used for the liquid crystalline composition R which exhibits a liquid crystal phase satisfying the numerical formula (I) may either be a low molecular weight liquid crystal line compound or a polymer liquid crystalline compound. However, from the standpoint of compatibility between the liquid crystalline composition R and the liquid crystalline composition D which exhibits a liquid crystal phase satisfying the numerical formula (II), the low molecular weight liquid crystalline compound is preferable.

As for the liquid crystalline compound used for the liquid crystalline composition R which exhibits a liquid crystal phase satisfying the numerical formula (I), such liquid crystalline compounds which exhibit a uniaxial liquid crystal phase having a positive birefringence are preferable and examples of the compounds include azomethines, azoxys, cyanobiphenyls, cyanophenyl esters, benzoic esters, phenyl cyclohexanecarbonate esters, cyanophenylcyclohexanes, cyano-substituted phenylpyrimidines, alkoxy-substituted phenylpyrimidines, phenyldioxanes, tolans and alkenylcyclohexylbenzonitriles.

The liquid crystalline compound used for the liquid crystalline composition R which exhibits a liquid crystal phase satisfying the numerical formula (I) preferably contains a substituent capable of performing an interaction (for example, a hydrogen bonding interaction or a dipole interaction) or a substituent capable of forming a covalent bonding (for example, a polymerizable group) between the liquid crystalline compound used for the liquid crystalline composition D which exhibits a liquid crystal phase satisfying the numerical formula (II). By containing such substituents as described above, when the liquid crystalline composition R and the liquid crystalline composition D are mixed with each other, compatibility of these compositions to each other is allowed to be favorable and, accordingly, phase separation into phases comprising respective compositions can be avoided. By a same reason, the liquid crystalline compound used for the liquid crystalline composition D preferably contains a similar group.

The liquid crystalline compound used for the liquid crystalline composition R which exhibits a liquid crystal phase satisfying the numerical formula (I) preferably contains a polymerizable group and more preferably contains a polymerizable group at an end of a molecule of the compound. By containing the polymerizable group, not only the phase separation between the liquid crystalline composition R and the liquid crystalline composition D can be prevented as described above, but also, when the liquid crystalline composition according to the present invention compound is used for a retardation film, a change of the phase difference by heat or the like can be prevented; therefore, this case is favorable.

As for the uniaxial liquid crystalline compounds each having a polymerizable group and a positive birefringence, compounds as described in *Makromol, Chem.*, Vol. 190, page 2255 (1989); *Advanced Materials*, Vol 5, page 107 (1993), U.S. Pat. Nos. 4,683,327, 5,622,648, 5770107, WO 95/225868, 95/24455, 97/00600, 98/23580, 98/52905, JP-A Nos. 1-272551, 6-16616, 7-110469, 11-80081 or 2001-328973 can be used.

Favorable examples as polymerizable groups each of which the liquid crystalline compound used for the liquid crystalline composition R has are set forth below:

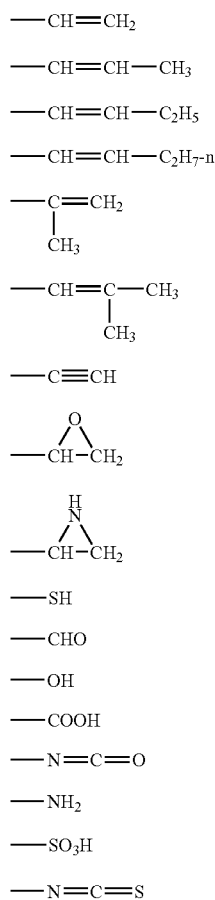

Among the aforementioned polymerizable groups, unsaturated polymerizable groups (Q1 to Q7), an epoxy group (Q8) or an aziridinyl group (Q-9) is preferable, an unsaturated polymerizable group is more preferable and an ethylenically unsaturated polymerizable groups (Q-1 to Q-6) are most preferable.

A shape of the liquid crystalline compound used for the liquid crystalline composition R which exhibits the liquid crystal phase satisfying the numerical formula (I) is not specifically limited and a rod-like shape, a rectangular plate-like shape or any other appropriate shape is permissible. Among these shapes, the rectangular plate-like shape is preferable from the standpoint of compatibility with the liquid crystalline composition D which exhibits the liquid crystal phase satisfying the numerical formula (II) or ease with which the liquid crystalline composition according to the present invention exhibits a biaxial liquid crystal phase.

In the case a liquid crystalline compound having a "rectangular plate-like" shape, it means that, not only the liquid crystalline compound individually contains at least two core moieties each of which has liquid crystallinity, but also it is a uniaxial liquid crystalline compound having a positive birefringence and a planar shape formed by the at least two core moieties being linked by at least one covalent bond. For example, in an illustrative compound (m-1) according to the present invention to be described below, a moiety of RO-Ph-OR (Ph representing benzene ring) corresponds to a core moiety which singly have crystallinity. The moieties of RO-Ph-OR are linked by a covalent bond, to thereby form the illustrative compound (m-1).

Generally, in the case of a compound having a "rectangular plate-like" shape, it means as described below. Namely, when a compound has a "rectangular plate-like" shape, both relations of Ll/Lm>1.1 and Lm/Ls·1.5 are established, wherein Ll, Lm, and Ls are a longest side length, a middle side length and a shortest side length of a rectangular parallelepiped in which inscribes the compound with a stabilized structure, respectively. A maximally stabilized structure of a compound can be determined by using MOPAC (semi-empirical molecular orbital-calculating program) and, more specifically, by using an AMI method (usable software: WinMOPAC; available from Fujitsu Limited) of the MOPAC.

According to the present invention, it is more preferable that the liquid crystalline compound having a rectangular plate-like shape, the compound being used for the liquid crystalline composition R which exhibits the liquid crystal phase satisfying the numerical formula (I), has further satisfies both of the following numerical formulae (IV) and (V):

$$1.2 < Ll/Lm < 10 \qquad (IV),$$

$$2.0 < Lm/Ls < 10 \qquad (V).$$

As for liquid crystalline compounds each having a rectangular plate-like shape, compounds as described in *Mol. Cry. Liq. Cry.*, Vol. 323, page 231 (1998), "*Senryo to Yakuhin (Dyes and Chemicals)*", Vol. 42, No. 4, page 85 (1997), "*Senryo to Yakuhin (Dyes and Chemicals)*", Vol. 42, No. 3, page 68 (1997) and the like, and compounds in each of which a polymerizable group is introduced into the thus-described compounds can be used.

Hereinafter, examples of liquid crystalline compounds which each have a rectangular plate-like shape and are favorable to be used for the liquid crystalline composition R are set forth below, but the present invention is not limited thereto.

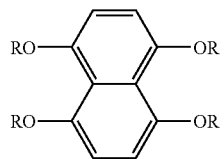
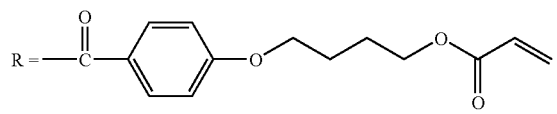
m-1
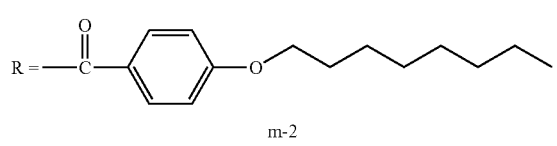
m-2
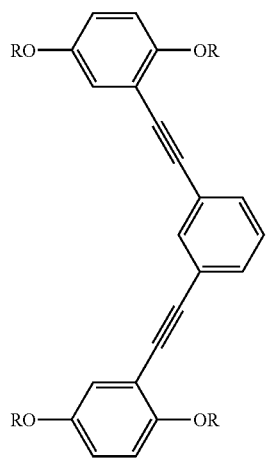
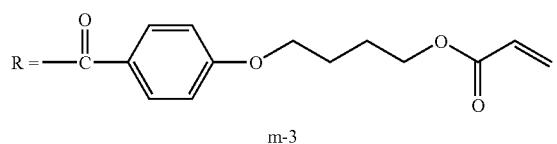
m-3
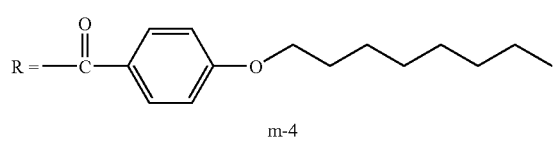
m-4
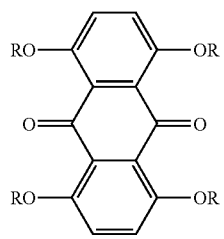
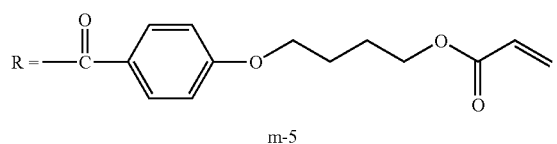
m-5
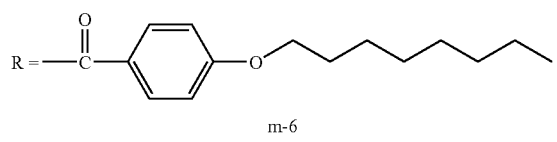
m-6
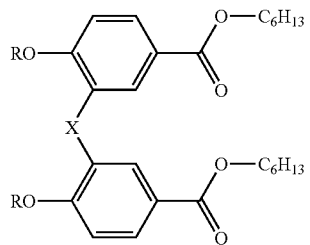
X = S
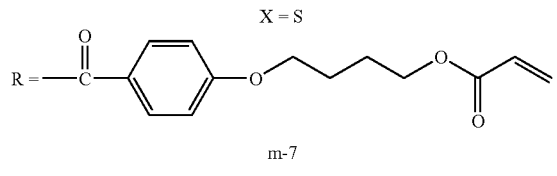
m-7
X = S
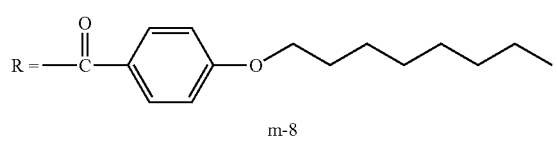
m-8

-continued
X = SO
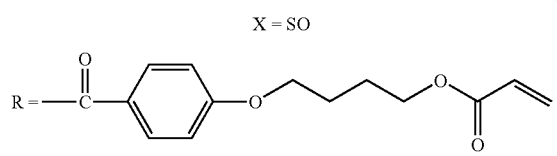
m-9
X = SO
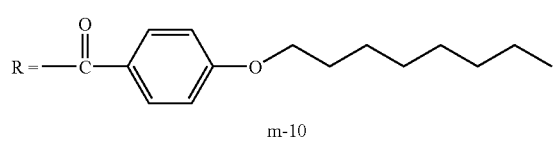
m-10
X = SO$_2$
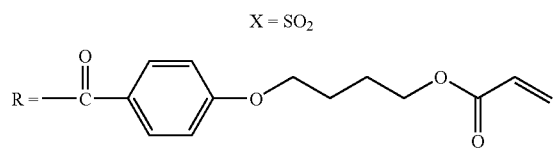
m-11
X = SO$_2$
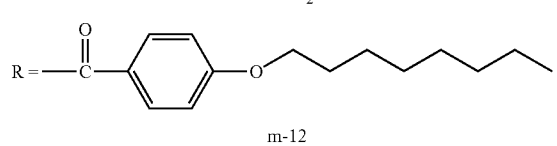
m-12
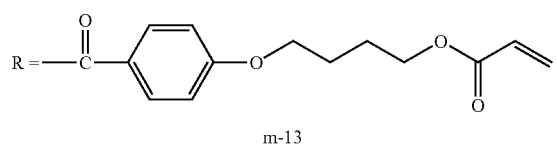
m-13
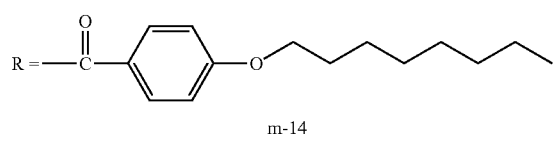
m-14
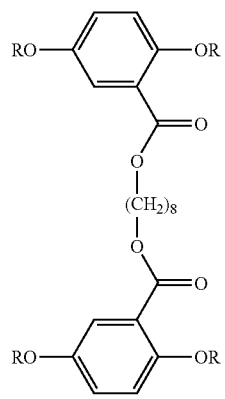
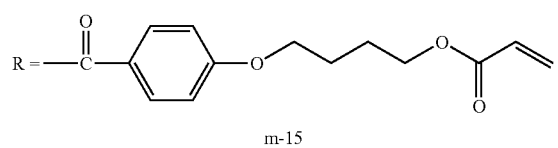
m-15
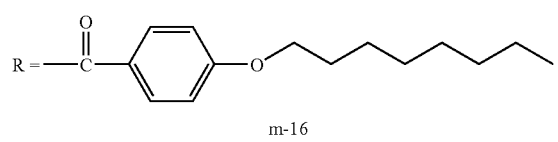
m-16
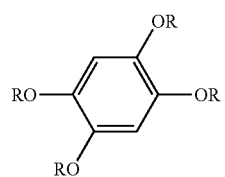
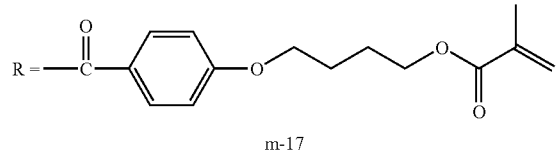
m-17
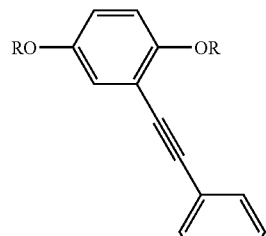
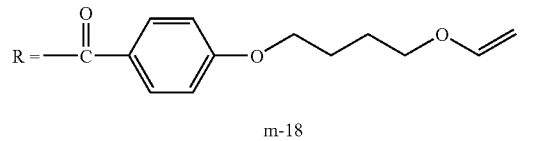
m-18
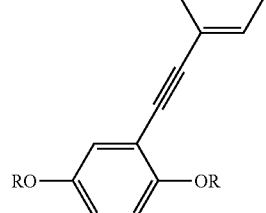
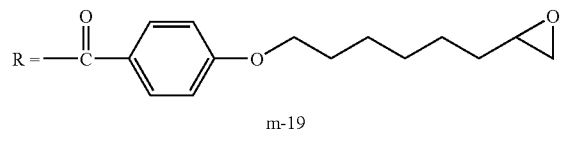
m-19

-continued
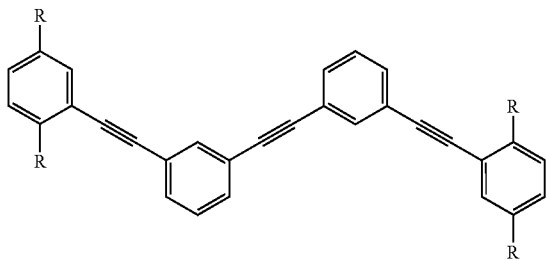
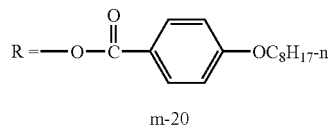
m-20
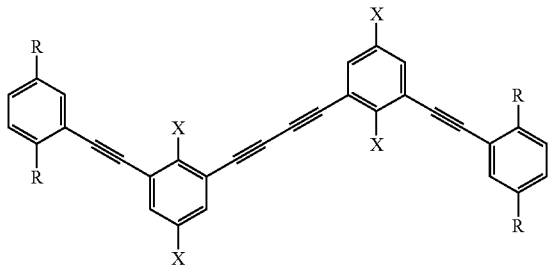
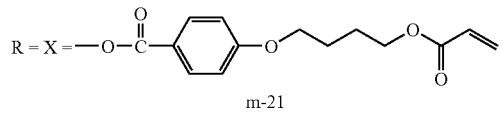
m-21
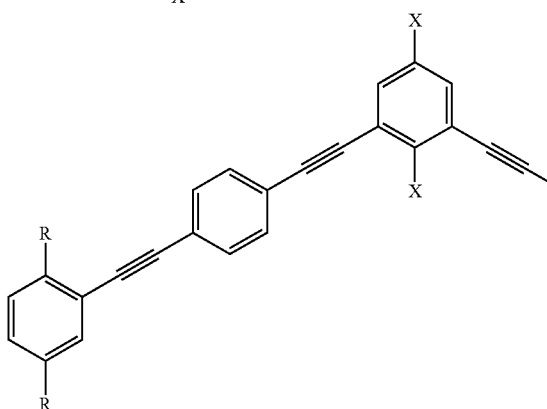
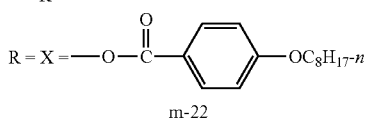
m-22
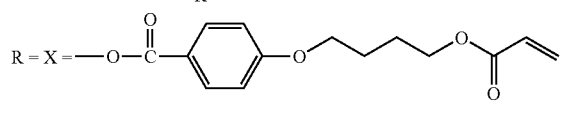
m-23
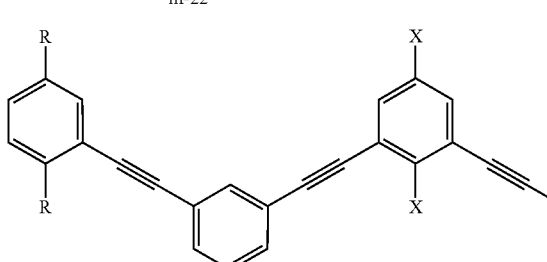
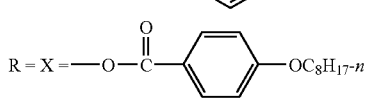
m-24
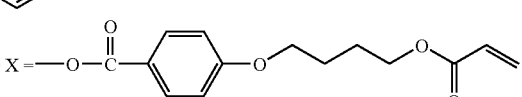
m-25
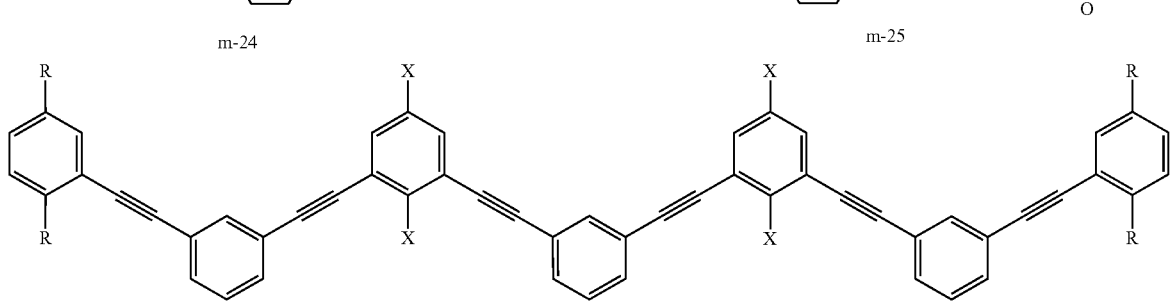

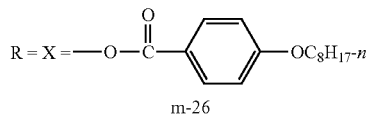

m-26

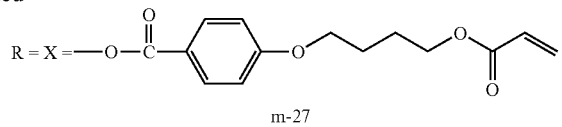

m-27

As for the liquid crystalline compounds each having a rectangular plate-like shape, other than the aforementioned specific examples, a liquid crystalline compound represented by the following formula (R-I) is preferable:

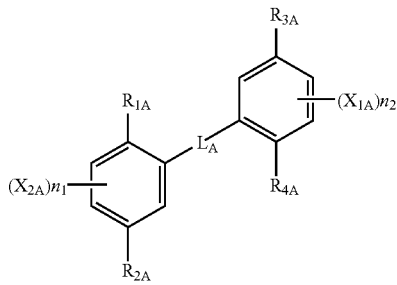

In the formula (R-I), $L_A$ represents —=— or —=—=—.

$X_{1A}$ and $X_{2A}$ each independently represent a halogen atom (preferably, a fluorine atom, a chlorine atom, a bromine atom or an iodine atom), a carboxyl group, a hydroxyl group, a cyano group, a nitro group, an alkyl group, an alkyloxy group, an acyl group, an acyloxy group or an alkyloxycarbonyl group. Particularly, a halogen atom, a carboxyl group, a hydroxyl group, a cyano group, an alkyl group having from 1 to 10 carbon atoms or an alkyloxy group having from 1 to 10 carbon atoms is preferably, and a halogen atom or a cyano group is most preferable.

$n_1$ and $n_2$ each independently represent an integer of from 0 to 3. $n_1$ and $n_2$ are each preferably an integer of from 0 to 2. Particularly, ($n_1+n_2$) is preferably an integer of from 1 to 4.

$R_{1A}$, $R_{2A}$, $R_{3A}$ and $R_{4A}$ are each independently represented by the following formula (R-IA):

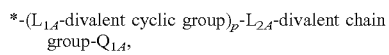

wherein * denotes a position to be bonded to the benzene ring in the formula (R-I).

$L_{1A}$ represents a single bond or a divalent linking group. When $L_{1A}$ is a divalent linking group, the divalent linking group is preferably at least one divalent group selected from the group consisting of —O—, —S—, —C(=O)—, —NR$_7$—, —CH$_2$—, —CH=CH— and —C≡C—. R$_7$ represents an alkyl group having from 1 to 7 carbon atoms or a hydrogen atom, wherein an alkyl group having from 1 to 4 carbon atoms or a hydrogen atom is preferable, and a methyl group, an ethyl group or a hydrogen atom is more preferable and a hydrogen atom is most preferable.

As for $L_{1A}$, a single bond, *—O—CO—, *—CO—O—, *—CH$_2$—CH$_2$—, *—O—CH$_2$—, *—CH$_2$—O—, *—CO—CH$_2$—CH$_2$—, *—CH=CH— or *—C≡C— (in this occasion, * denotes that in the formula (R-IA)) is preferable and, particularly, a single bond or *—O—CO— is preferable.

$L_{2A}$ represents a single bond or a divalent linking group. When $L_{2A}$ represents a divalent linking group, , the divalent linking group is preferably at least one divalent linking group selected from the group consisting of —O—, —S—, —C(=O)— and —NR$_7$—. R$_7$ represents an alkyl group having from 1 to 7 carbon atoms or a hydrogen atom, in which an alkyl group having from 1 to 4 carbon atoms or a hydrogen atom is preferable, and a methyl group, an ethyl group or a hydrogen atom is more preferable and a hydrogen atom is most preferable.

As for $L_{2A}$, a single bond, *—O—, *—O—CO—, *—CO—O—, *—O—CO—O—, *—CO—, *—S— or *—NR$_7$— (in this case, * denotes a position to be liked to a divalent cyclic group in the formula (R-IA)) is preferable and, particularly, a single bond, *—O—, *—O—CO—, *—CO—O— or *—O—CO—O— is preferable.

The divalent cyclic group is a divalent linking group having at least one cyclic structure. The ring in the divalent cyclic group is preferably a 5-membered, 6-membered or 7-membered ring and, more preferably, 5-membered or 6-membered ring and, most preferably, 6-membered ring. The ring in the cyclic group may be a condensed ring. However, a single ring is more preferable than the condensed ring. Further, the ring in the cyclic group may be any one of an aromatic ring, an aliphatic ring and a heterocycle. Examples of aromatic rings include a benzene ring and a naphthalene ring. Examples of aliphatic rings include a cyclohexane ring. Examples of heterocycles include a pyridine ring, a pyrimidine ring, a thiophene ring, a 1,3-dioxane ring and a 1,3-dithiane ring.

Among divalent cyclic groups, the cyclic group having a benzene ring is preferably 1,4-phenylene. The cyclic group having a naphthalene ring is preferably naphthalene-1,5-diyl or naphthalene-2,6-diyl. The cyclic group having a cyclohexane ring is preferably 1,4-cyclohexylene. The cyclic group having a pyridine ring is preferably pyridine-2,5-diyl. The cyclic group having a pyrimidine ring is preferably pyrimidine-2,5-diyl. The cyclic group having a thiophene ring is preferably thiophene-2,5-diyl. The cyclic group having a 1,3-dioxane ring is preferably 1,3-dioxylene-2,5-diyl. A skeleton having a 1,3-dithiane ring is preferably 1,3-dithianylene-2,5-diyl.

The divalent cyclic group is preferably 1,4-phenylene, 1,4-cyclohexylene, pyridine-2,5-diyl, pyrimidine-2,5-diyl or 1,3-dioxylene-2,5-diyl, more preferably 1,4-phenylene, 1,4-cyclohexylene or 1,3-dioxylene-2,5-diyl and, most preferably, 1,4-phenylene.

The divalent cyclic group may have a substituent, and the substituent is preferably a halogen atom (preferably a fluorine atom, a chlorine atom, a bromine atom or an iodine atom), an alkyl group having from 1 to 8 carbon atoms, an alkyloxy group having from 1 to 8 carbon atoms, an acyl group having from 2 to 8 carbon atoms, an acyloxy group having from 2 to 8 carbon atoms, an alkoxycarbonyl group having from 2 to 8 carbon atoms, a nitro group or a cyano group and particularly preferably a halogen atom, an alkyl group having from 1 to 3 carbon atoms, an alkyloxy group having from 1 to 3 carbon atoms, an acyl group having from 2 to 4 carbon atoms, an acyloxy group having from 2 to 4 carbon atoms, an alkoxycarbonyl group having from 2 to 4 carbon atoms or a cyano group.

The divalent chain group is an alkylene group, a substituted alkylene group, an alkenylene group, a substituted alkenylene group, an alkynylene group or a substituted alkynylene group. Among these groups, an alkylene group, a substituted alkylene group, an alkenylene group or a substituted alkenylene group is preferable, and an alkylene group or an alkenylene group is more preferable.

The alkylene group as a chain group may have a branch. Further, —CH$_2$— in the alkylene group may be substituted by, for example, —O— or —S—. The number of carbon atoms of the alkylene group is preferably from 1 to 16, more preferably from 2 to 14 and, most preferably, from 2 to 12. An alkylene moiety of a substituted alkylene group is same as that of the aforementioned alkylene group. Examples of such substituents include an alkyl group and a halogen atom.

The alkenylene group as a divalent chain group may either have a substituted or unsubstituted alkylene group or a branch in a main chain. Further, when —CH$_2$— is present in the alkenylene group, —CH$_2$— may be substituted by —O— or —S—. The number of carbon atoms of the alkenylene group is preferably from 2 to 16, more preferably from 2 to 14 and, most preferably, from 2 to 12. An alkenylene moiety of a substituted alkenylene group is same as that of the aforementioned alkenylene group. Examples of such substituents include an alkyl group and a halogen atom.

The alkynylene group as a divalent chain group may either have a substituted or unsubstituted alkylene group or a branch in a main chain. Further, when —CH$_2$— is present in the alkynylene group, —CH$_2$— may be substituted by —O— or —S—. The number of carbon atoms of the alkynylene group is preferably from 2 to 16, more preferably from 2 to 14 and, most preferably, from 2 to 12. An alkynylene moiety of a substituted alkynylene group is same as that of the aforementioned alkynylene group. Examples of such substituents include an alkyl group and a halogen atom.

Specific examples of the divalent chain group include ethylene, trimethylene, tetramethylene, 1-methyl-tetramethylene, pentamethylene, hexamethylene, octamethylene, nonamethylene, decamethylene, undecamethylene, dodecamethylene, 2-butenylene and 2-butynylene.

The divalent chain group is preferably a substituted or unsubstituted alkylene group having from 1 to 16 carbon atoms, a substituted or unsubstituted alkenylene group having from 2 to 16 carbon atoms or a substituted or unsubstituted alkynylene group having from 2 to 16 carbon atoms, particularly preferably, a substituted or unsubstituted alkylene group having from 1 to 12 carbon atoms and, most preferably, an unsubstituted alkylene group having from 1 to 12 carbon atoms. A substituent of the chain group is preferably an alkyl group having from 1 to 5 carbon atoms or a halogen atom.

$Q_{14}$ represents a polymerizable group. Examples of such polymerizable groups are described below.

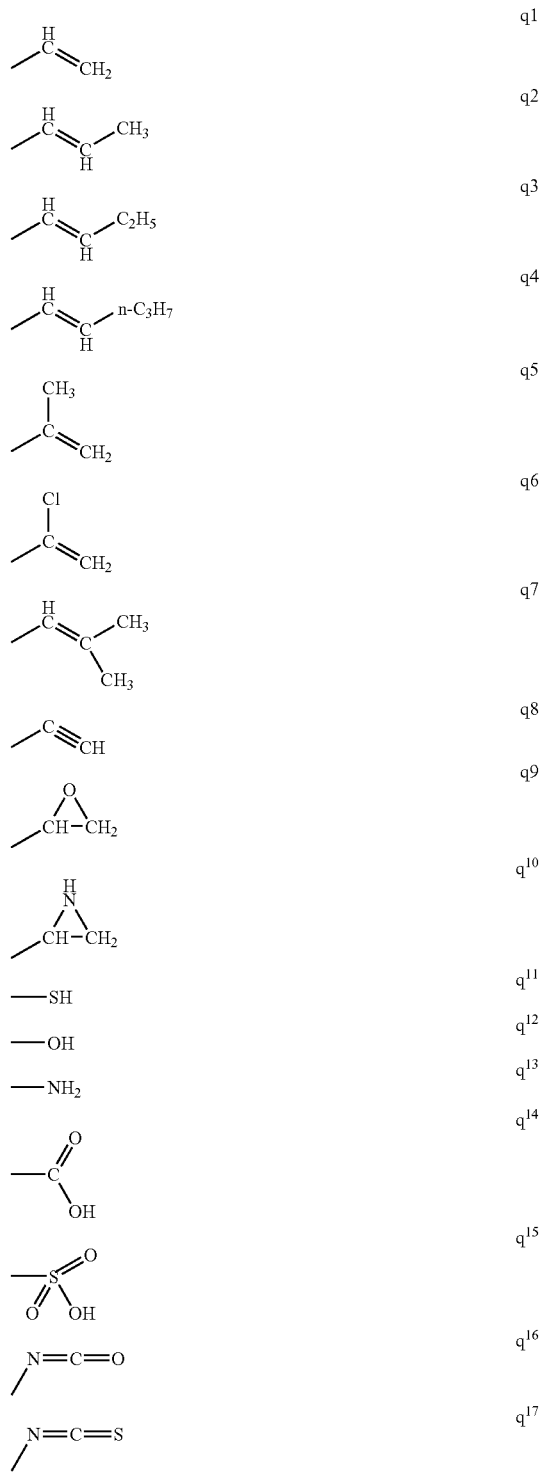

In the aforementioned examples, $q_1$ to $q_{10}$ are preferable and $q_1$ to $q_8$ are more preferable.

Further, the polymerizable group is particularly preferably a functional group capable of performing an addition-polymerization reaction. As for such polymerizable group, a polymerizable ethylenic unsaturated group or a ring-opening polymerizable group is preferable.

Examples of such polymerizable ethylenic unsaturated groups include groups represented by the following formulas (M-1) to (M-6).

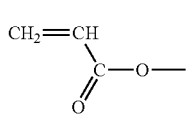
(M-1)

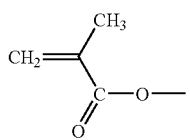
(M-2)

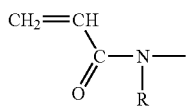
(M-3)

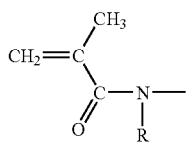
(M-4)

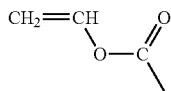
(M-5)

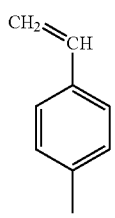
(M-6)

In the formulas (M-3) and (M-4), R represents a hydrogen atom or an alkyl group. R is preferably a hydrogen atom or a methyl group.

Among the formulas (M-1) to (M-6), the formula (M-1) or (M-2) is preferable, and the formula (M-1) is most preferable.

The ring-opening polymerizable group is preferably a cyclic ether group and, especially, an epoxy group or an oxetanyl group is more preferable, and an epoxy group is most preferable.

p represents an integer of from 0 to 3, in which 1 or 2 is preferable and 1 is most preferable.

A methine group in benzene rings of the compound represented by formula (R-I) may be substituted by a nitrogen atom.

Hereinafter, examples of compounds represented by the formula (R-I) are set forth below, but the present invention is not limited thereto.

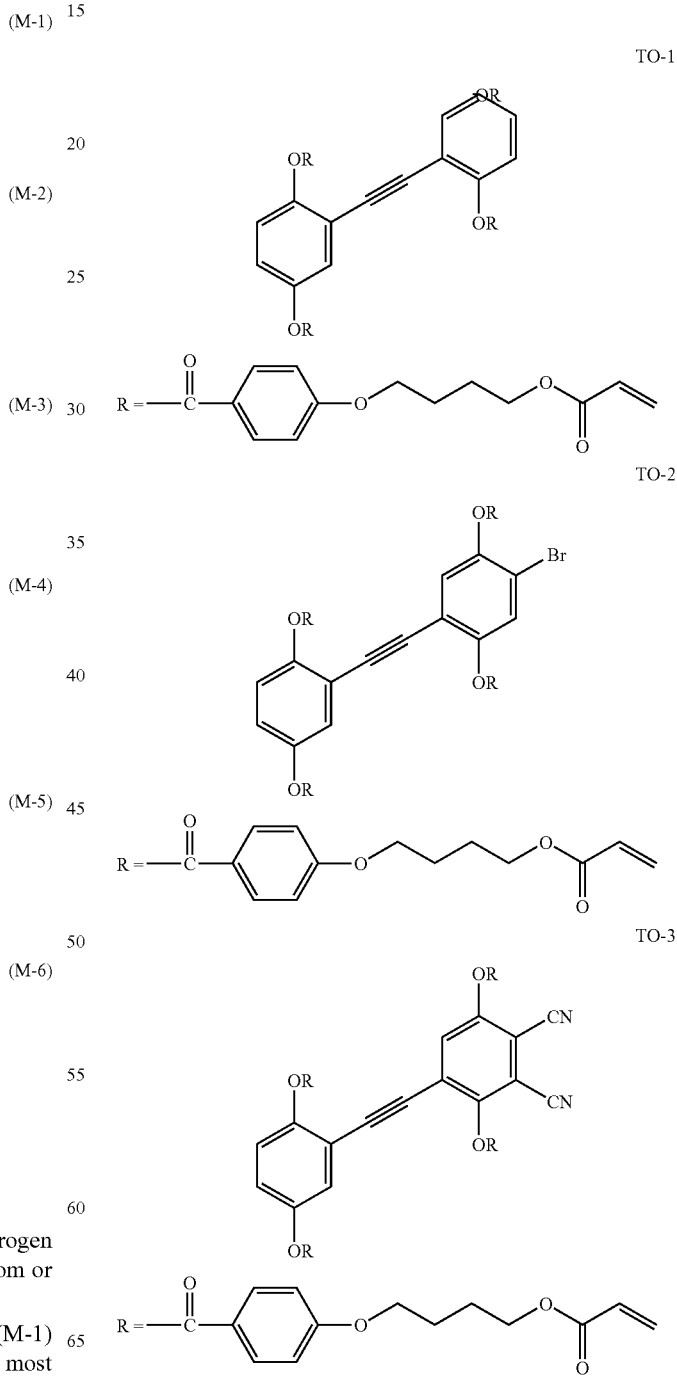

TO-4
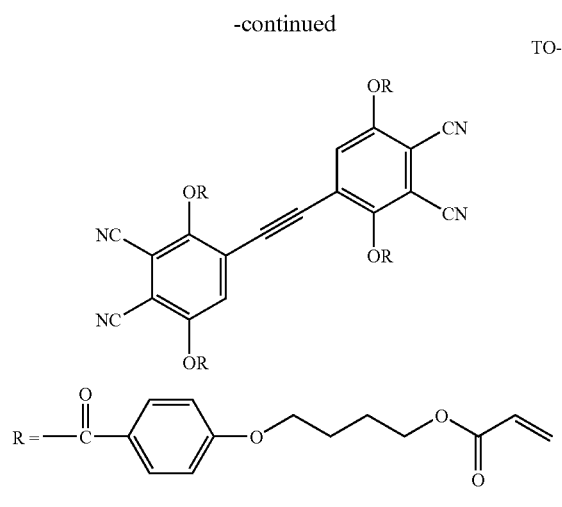
TO-7
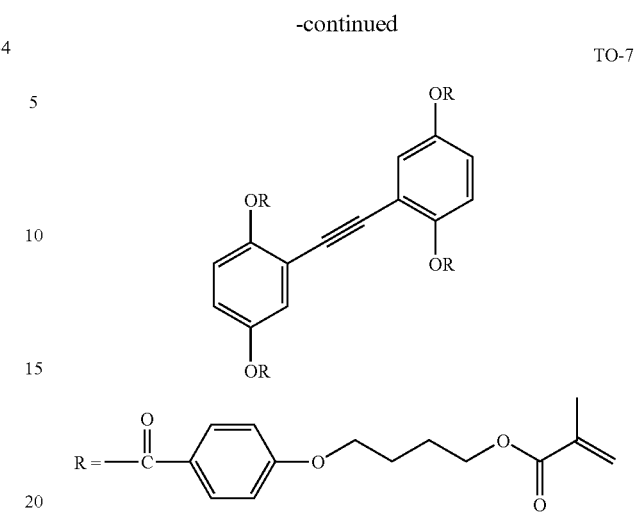
TO-5
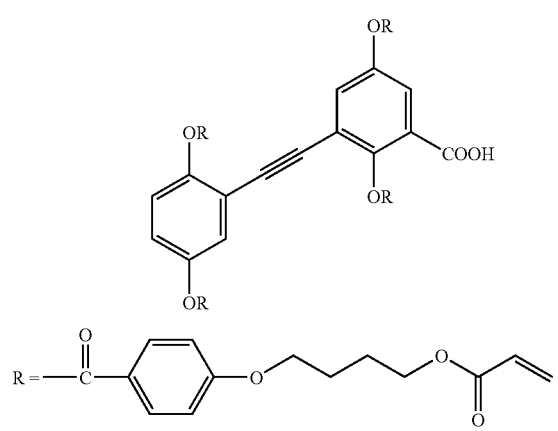
TO-8
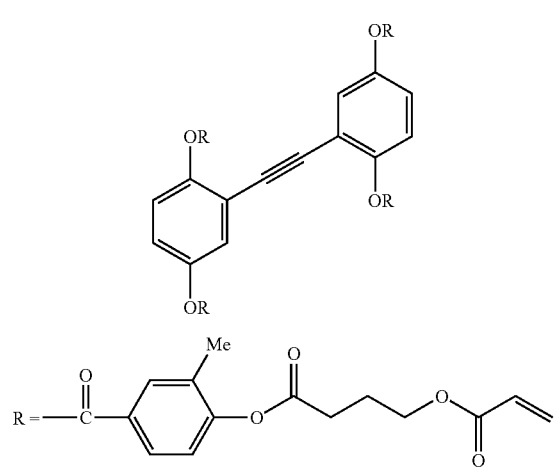
TO-6
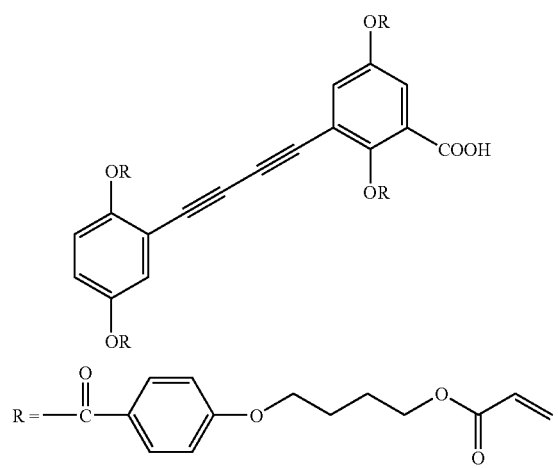
TO-9
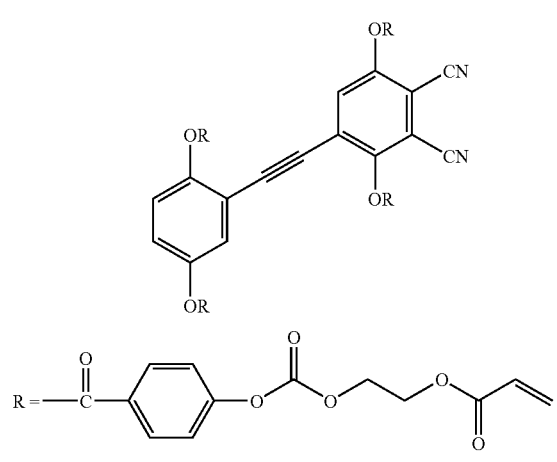

-continued

TO-10
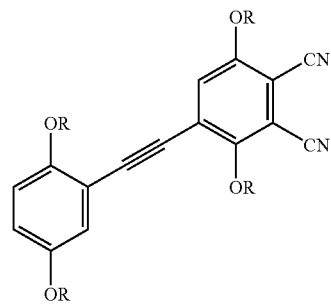

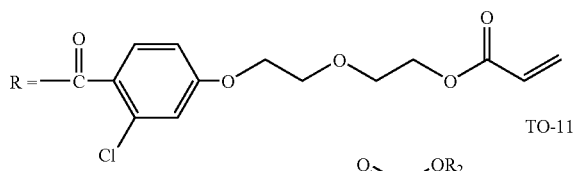

TO-11
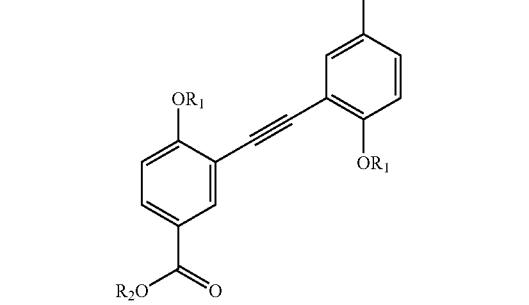

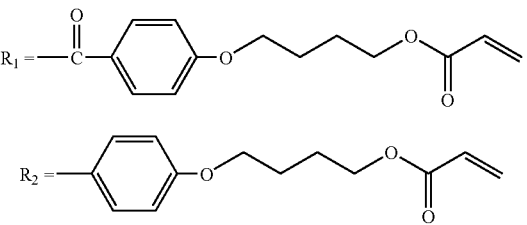

TO-12
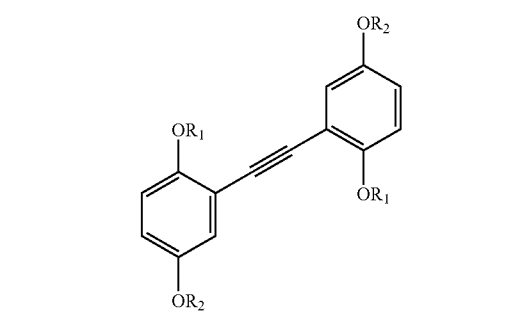

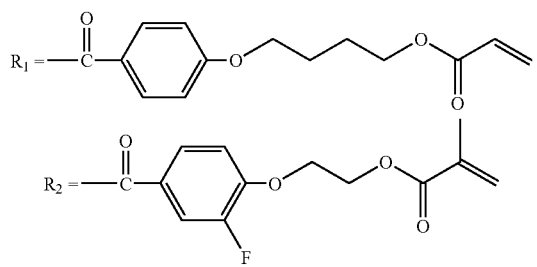

(Liquid Crystalline Composition R Exhibiting Liquid Crystal Phase Satisfying Numerical Formula (II))

As for liquid crystal phases which satisfy the numerical formula (II), for example, a discotic nematic phase, a columnar phase and a columnar-lamella phase can be mentioned. According to the present invention, the liquid crystal phase which satisfies the numerical formula (II) is particularly preferably the discotic nematic phase.

On the other hand, the The liquid crystal phase which is difficult to be judged whether it belongs to a uniaxial liquid crystal phase or a biaxial liquid crystal phase has been known. For example, the liquid crystal phase described in D. Demus and J. Goodby, "*Handbook of Liquid Crystal*", Vol. 2B: Low Molecular Weight Liquid Crystals II, pp. 933 to 943, published by WILEY-VCH can be said to be a liquid crystal phase which is difficult to be judged. As for the liquid crystal phase which satisfies the numerical formula (II), such liquid crystal phase which is difficult to be judged whether it is uniaxial or biaxial as described above is included.

The liquid crystalline compound used for the liquid crystalline composition D which exhibits a liquid crystal phase satisfying the numerical formula (II) may either be a low molecular weight liquid crystalline compound or a polymer liquid crystalline compound. However, from the standpoint of compatibility between the liquid crystalline composition D and the liquid crystalline composition R which exhibits a liquid crystal phase satisfying the numerical formula (I), the low molecular weight liquid crystalline compound is preferable.

As for the liquid crystalline composition D which exhibits a liquid crystal phase satisfying the numerical formula (II) compounds described in various documents (for example, C. Destrade et al, *Mol. Crys. Liq. Crys.*, Vol. 71, page 111 (1981); *Japan Chemical Society, Quarterly Chemical Review*, No. 22, "*Ekisho no Kagaku* (*Liquid Crystal Chemistry*)", Chapters 5 and Chapter 10, Section 2 (1994); B. Kohne et al., *Angew. Chem. Soc. Chem. Comm.*, page 1794 (1985); and J. Zhanget et al., *J. Am. Chem. Soc.*, Vol. 116, page 2655 (1994)) may be used in the present invention.

The liquid crystalline compound used for the liquid crystalline composition D which exhibits a liquid crystal phase satisfying the numerical formula (II) preferably has a polymerizable group and more preferably has the polymerizable group at a terminal of a molecule of the compound. It is preferable to have the polymerizable group since a phase separation between the liquid crystalline composition D and the liquid crystalline composition R can be prevented as described above and, also, a change of phase difference by heat or the like to be caused at the time of utilizing the liquid crystalline composition according to the present invention to a retardation film or the like can be prevented. The compound represented by the following formula (D) is preferable: Formula (D): D(-L-Q)$_n$.

In the formula (D), D represents a discotic core; L represents a divalent linking group; and Q represents a polymerizable group. Further, n represents an integer of from 3 to 12. Examples of such discotic cores (D) are set forth below. In the examples, LQ (or QL) means a combination of the divalent linking group (L) with the polymerizable group (Q). Structural formulas of specific examples (D1 to D15) represented by the formula (D) are set forth below.

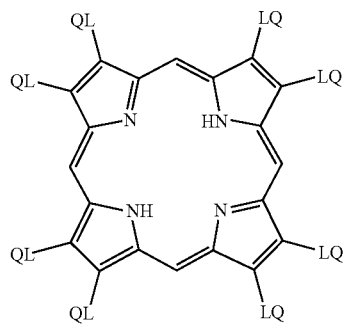 (D1)
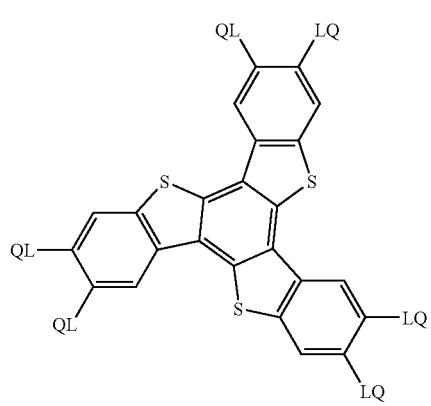 (D2)
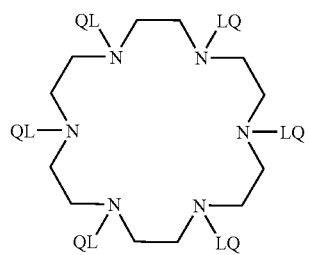 (D3)
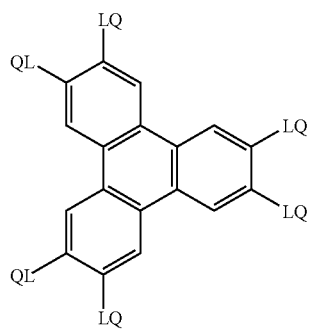 (D4)
-continued
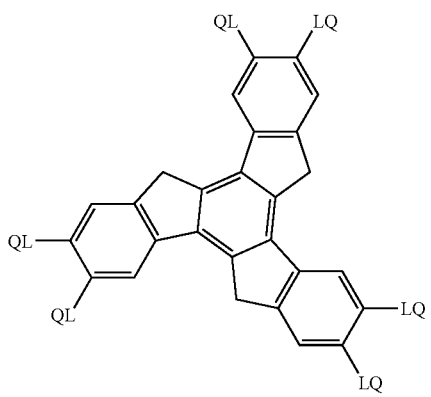 (D5)
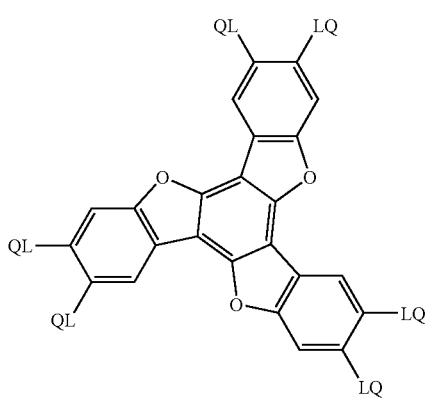 (D6)
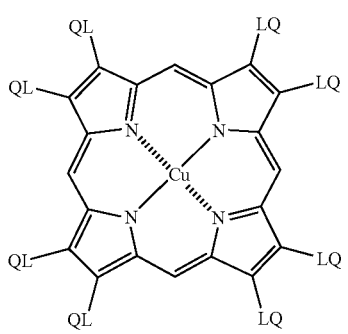 (D7)
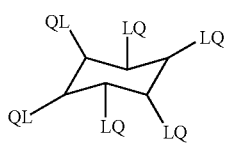 (D8)

-continued
(D9)
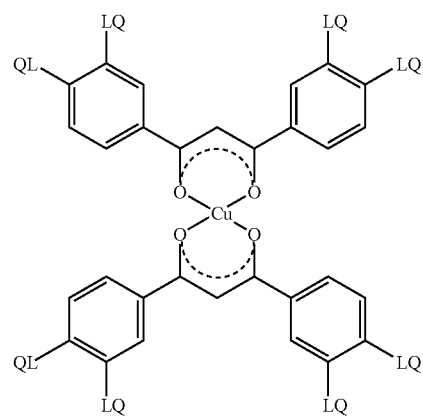
(D10)
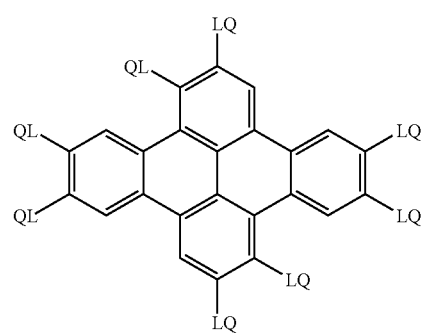
(D11)
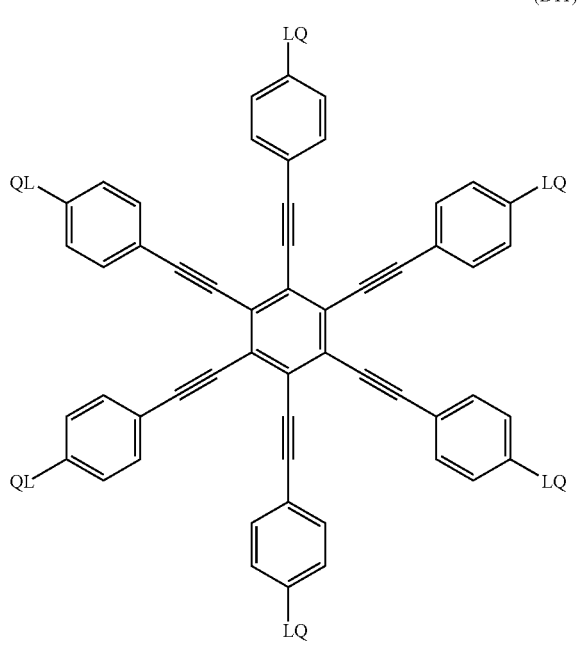
-continued
(D12)
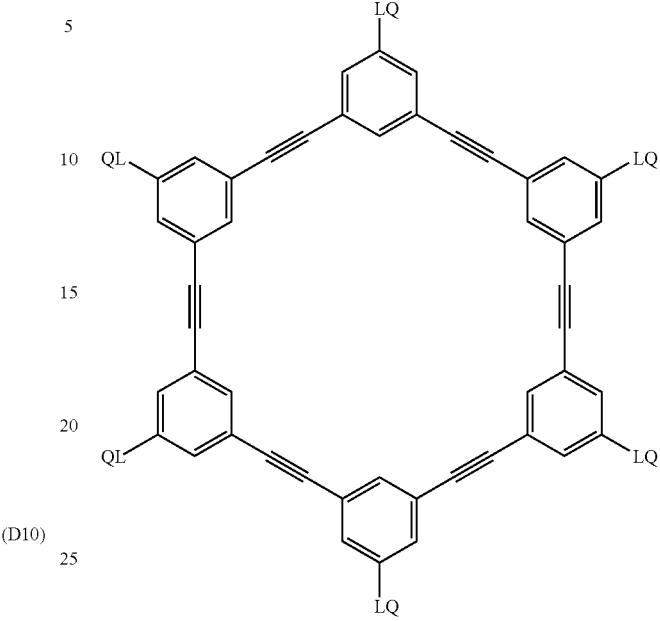
(D13)
(D14)
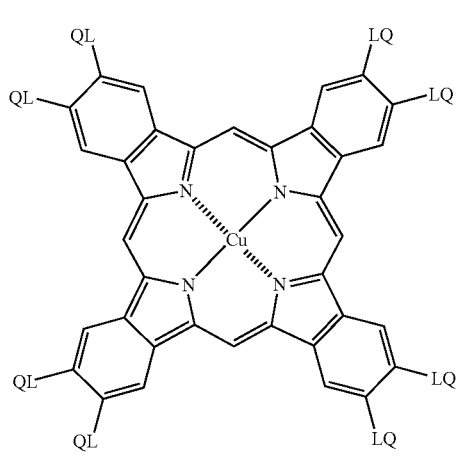

-continued

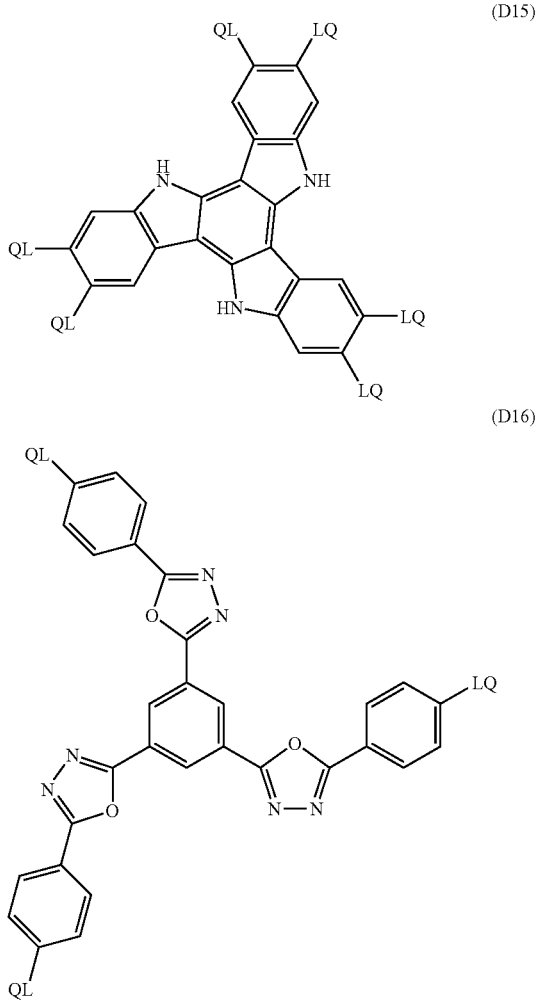

(D15)

(D16)

L in the formula (D) is preferably at least one divalent linking group selected from the group consisting of an alkylene group, an alkenylene group, an arylene group, —C(=O)—, —NH—, —O— and —S—. L is more preferably a group in which at least two divalent groups selected from the group consisting of an alkylene group, an alkenylene group, an arylene group, —C (=O)—, —NH—, —O— and —S— are combined with each other. L is most preferably a group in which at least two divalent groups selected from the group consisting of an alkylene group, an alkenylene group, an arylene group, —C (=O)— and —O— are combined with each other. The number of carbon atoms of the alkylene group is preferably from 1 to 12. The number of carbon atoms of the alkenylene group is preferably from 2 to 12. The number of carbon atoms of the arylene group is preferably from 6 to 10. The alkylene group, the alkenylene group and the arylene group may have a substituent group (such as an alkyl group, a halogen atom, a cyano group, an alkoxy group, an acyloxy group).

Examples of the divalent linking groups (L) are described below. In each formula of the examples, a left side thereof is bonded to a discotic core (D), while a right side thereof is bonded to a polymerizable group (Q). AL represents an alkylene group or an alkenylene group, while AR represents an arylene group.

L1: -AL-C(=O)—O-AL-
L2: -AL-C(=O)—O-AL-O—
L3: -AL-C(=O)—O-AL-C-AL-
L4: -AL-C(=O)—O-AL-O—C(=O)—
L5: —C(=O)-AR-O-AL-
L6: —C(=O)-AR-O-AL-O—
L7: —C(=O)-AR-O-AL-O—C(=O)—
L8: —C(=O)—NH-AL-
L9: —NH-AL-O—
L10: —NH-AL-O—C(=O)—
L11: —O-AL-
L12: —O-AL-O—
L13: —O-AL-O—C(=O)—
L14: —O-AL-O—C(=O)—NH-AL-
L15: —O-AL-S-AL-
L16: —O—C(=O)-AL-AR-O-AL-O—C(=O)—
L17: —O—C(=O)-AR-O-AL-C(=O)—
L18: —O—C(=O)-AR-O-AL-O—C(=O)—
L19: —O—C(=O)-AR-O-AL-O-AL-O—C(=O)—
L20: —O—C(=O)-AR-O-AL-O-AL-O-AL-O—C(=O)—
L21: —S-AL-
L22: —S-AL-O—
L23: —S-AL-O—C(=O)—
L24: —S-AL-S-AL-
L25: —S-AR-AL-

The polymerizable group (Q) in the formula (D) is not particularly limited. When the liquid crystalline composition according to the present invention is polymerized, it can be determined in accordance with types of polymerization reactions.

Preferable specific examples of such polymerizable groups (Q) are same as those described in the liquid crystalline composition R which exhibits a liquid crystal phase satisfying the numerical formula (I) and, also, the more preferable polymerizable groups (Q) are same as those described in the liquid crystalline composition R which exhibits a liquid crystal phase satisfying the numerical formula (I).

In the formula (D), n is an integer of from 3 to 12. A specific number is determined in accordance with types of discotic cores (D). n is an integer of particularly preferably from 3 to 6 and, most preferably, 3. Further, plural combinations of L and Q each may be different from one another; however, they are preferably same with one another.

Two or more types of discotic liquid crystalline compounds can simultaneously be used each as a discotic compound. For example, a molecule having a polymerizable group (Q) and a molecule having no polymerizable group can simultaneously be used in combination.

The non-polymerizable discotic liquid crystalline compound is preferably a compound in which the polymerizable group (Q) of the aforementioned polymerizable discotic liquid crystalline compound is changed into a hydrogen atom or an alkyl group. Namely, the non-polymerizable discotic liquid crystalline compound is preferably represented by the following formula:

D(-L-R), wherein D represents a discotic core; L represents a divalent linking group; R represents a hydrogen atom or an alkyl group; and n represents an integer of from 3 to 12. Examples of the discotic cores (D) in the formula are the same as those described in the aforementioned polymerizable discotic liquid crystalline compound except that LQ (or QL) is changed into LR (or RL). Further, examples of the divalent linking groups (L) are also same as those described in the aforementioned polymerizable discotic liquid crystalline compound. The alkyl group of R has preferably from 1 to 40 carbon atoms and, more preferably, from 1 to 30 carbon atoms. A chain alkyl group is preferred to a cyclic alkyl group and, further, a straight chain alkyl group is preferred to a branched chain alkyl group. R is particularly preferably a hydrogen atom or a straight chain alkyl group having from 1 to 30 carbon atoms.

The liquid crystalline compound used for the liquid crystalline composition D which exhibits a liquid crystal phase satisfying the numerical formula (II) is more preferably a compound represented by the following formula (D-2):

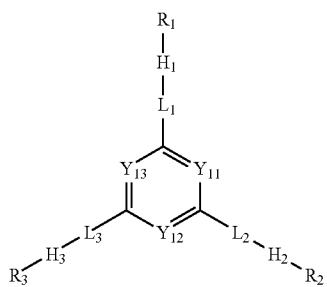

In the formula (D-2), $Y_{11}$, $Y_{12}$ and $Y_{13}$ each independently represent a methine group or a nitrogen atom.

In a case in which $Y_{11}$, $Y_{12}$ and $Y_{13}$ each independently represent a methine group, the methine group may have a substituent. Examples of such substituents include an alkyl group (for example, a methyl group, an ethyl group, an isopropyl group or a tert-butyl group), an alkenyl group (for example, a vinyl group, an allyl group, a 2-butenyl group or a 3-pentenyl group), an alkynyl group (for example, a propargyl group or a 3-pentynyl group), an aryl group (for example, a phenyl group, a p-methylphenyl group or a naphthyl group), a substituted or unsubstituted amino group (for example, an unsubstituted amino group, a methylamino group, a dimethylamino group, a diethylamino group or an anilino group), an alkoxy group (for example, a methoxy group, an ethoxy group or a butoxy group), an aryloxy group (for example, a phenyloxy group or a 2-naphthyloxy group), an acyl group (for example, an acetyl group, a benzoyl group, a formyl group or a pivaloyl group), an alkoxycarbonyl group (for example, a methoxycarbonyl group or an ethoxycarbonyl group), an aryloxycarbonyl group (for example, a phenyloxycarbonyl group), an acyloxy group (for example, an acetoxy group or a benzoyloxy group), an acylamino group (for example, an acetylamino group, or a benzoylamino group), an alkoxycarbonylamino group (for example, a methoxycarbonylamino group), an aryloxycarbonylamino group (for example, a phenyloxycarbonylamino group), an alkylsulfonylamino group (for example, a methane sulfonylamino group), an arylsulfonylamino group (for example, a benzene sulfonylamino group), a sulfamoyl group (for example, a sulfamoyl group, an N-methyl sulfamoyl group, an N,N-dimethylsulfamoyl group or an N-phenylsulfamoyl group), a carbamoyl group (for example, an unsubstituted carbamoyl group, an N-methylcarbamoyl group, an N,N-diethylcarbamoyl group or an N-phenylcarbamoyl group), an alkylthio group (for example, a methylthio group, an ethylthio group), an arylthio group (for example, a phenylthio group), an alkylsulfonyl group (for example, a mesyl group), an arylsulfonyl group (for example, a tosyl group), an alkylsulfinyl group (for example, a methane sulfinyl group), an arylsulfinyl group (a benzene sulfinyl group), an ureido group (for example, an unsubstituted ureido group, a 3-methylureido group, or a 3-phenylureido group), a phosphoric acid amido group (for example, a diethyl phosphoric acid amido group or a phenyl phosphoric acid amido group), a hydroxyl group, a mercapto group, a halogen atom (for example, a fluorine atom, a chlorine atom, a bromine atom or an iodine atom), a cyano group, a sulfo group, a carboxyl group, a nitro group, a hydroxamic acid group, a sulfino group, a hydrazino group, an imino group, a heterocyclic group (namely, a heterocyclic group containing a hetero atom such as a nitrogen atom, an oxygen atom or a sulfur atom, for example, an imidazolyl group, a pyridyl group, a quinolyl group, a furyl group, a piperidyl group, a morpholino group, benzoxazolyl group, a benzimidazolyl group or a benzothiazolyl group) and a silyl group (for example, a trimethylsilyl group or a triphenylsilyl group) These substituents may each independently be further substituted by any one of these substituents.

Among these substituents, substituents for a methine group is preferably an alkyl group, an alkoxy group, an aryloxy group, an acyl group, an alkoxycarbonyl group, an acyloxy group, an acylamino group, an alkoxycarbonylamino group, an alkylthio group, an arylthio group, a halogen atom or a cyano group, more preferably an alkyl group, an alkoxy group, an alkoxycarbonyl group, an acyloxy group, a halogen atom or a cyano group, and most preferably an alkyl group having from 1 to 12 carbon atoms, an alkoxy group having from 1 to 12 carbon atoms, an alkoxycarbonyl group having from 2 to 12 carbon atoms, an acyloxy group having from 2 to 12 carbon atoms, a halogen atom or a cyano group.

Most preferably, all of $Y_{11}$, $Y_{12}$ and $Y_{13}$ are a methine group. A methine group is most preferably unsubstituted.

In the formula (D-2), $L_1$, $L_2$ and $L_3$ each independently represent a single bond or a divalent linking group. When $L_1$, $L_2$ and $L_3$ each independently represent the divalent linking group, they are each independently preferably at least one divalent linking group selected from the group consisting of —O—, —S—, —C(=O)—, —NR$_7$—, —CH=CH—, —C≡C— and a divalent cyclic group. R$_7$ represents an alkyl group having from 1 to 7 carbon atoms or a hydrogen atom, preferably an alkyl group having from 1 to 4 carbon atoms or a hydrogen atom, more preferably a methyl group, an ethyl group or a hydrogen atom, and most preferably a hydrogen atom.

The divalent cyclic group represented by each of $L_1$, $L_2$ and $L_3$ is a divalent linking group having at least one type of cyclic structure. A ring in the divalent cyclic group is preferably a 5-membered ring, 6-membered ring or a 7-membered ring, more preferably a 5-membered ring or a 6-membered ring, and most preferably a 6-membered ring. The ring in the cyclic group may be a condensed ring. However, a single ring is preferred to a condensed ring. Further, the ring contained in the cyclic group may be any one of an aromatic ring, an aliphatic ring and a heterocycle. Examples of such aromatic rings include a benzene ring and a naphthalene ring. Examples of such aliphatic rings include a cyclohexane ring. Examples of such heterocycles include a pyridine ring and a pyrimidine ring. The cyclic ring is preferably an aromatic ring or a heterocycle.

Among divalent cyclic rings represented by $L_1$, $L_2$ and $L_3$, as for a cyclic group having a benzene ring, 1,4-phehylene is preferable; as for a cyclic group having a naphthalene ring, naphthalene-1,5-diyl or naphthalene-2,6-diyl is preferable; as for a cyclic group having a cyclohexane ring, 1,4-cyclohexylene is preferable; as for a cyclic group having a pyridine ring, pyridine-2,5-diyl is preferable; and as for a cyclic group having a pyrimidine ring, pyrimidine-2,5-diyl is preferable.

The divalent cyclic group represented by each of $L_1$, $L_2$ and $L_3$ may have a substituent. Examples of such substituents include a halogen atom, a cyano group, a nitro group, an alkyl group having from 1 to 16 carbon atoms, a halogen-substituted alkyl group having from 1 to 16 carbon atoms, an alkoxy group having from 1 to 16 carbon atoms, an acyl group having from 2 to 16 carbon atoms, an alkylthio group having from 1 to 16 carbon atoms, an acyloxy group having from 2 to 16 carbon atoms, an alkoxycarbonyl group having from 2 to 16 carbon atoms, a carbamoyl group, an alkyl-substituted carbamoyl group having from 2 to 16 carbon atoms and an acylamino group having from 2 to 16 carbon atoms.

As for $L_1$, $L_2$ and $L_3$, a single bond, *—O—CO—, *—CO—O—, *—CH=CH—, *—C≡C—, *-divalent cyclic group-, *—O—CO-divalent cyclic group-, *—CO—O-divalent cyclic group-, *—CH=CH-divalent cyclic group-, *—C≡C-divalent cyclic group-, *-divalent cyclic group-O—CO—, *-divalent cyclic group-CO—O—, *-divalent cyclic group-CH=CH— or *-divalent cyclic group-C≡C— is preferable. Particularly, a single bond, *—CH=CH—, *—C≡C—, -, *—CH=CH-divalent cyclic group- or *—C≡C-divalent cyclic group- is preferable. * denotes a position to be bonded to the 6-membered ring containing $Y_{11}$, $Y_{12}$ and $Y_{13}$ in the formula (D-2).

$H_1$, $H_2$ and $H_3$ each independently represent a divalent 5-membered cyclic group. The divalent 5-membered cyclic group is preferably a heterocycle. Examples of hetero atoms include an oxygen atom, a nitrogen atom, a sulfur atom, a boron atom and a phosphorous atom. Particularly, an oxygen atom, a nitrogen atom or a sulfur atom is preferable. Particularly, a heterocycle containing a nitrogen atom and an oxygen atom is preferable.

A divalent 5-membered cyclic group has preferably at least one methine group, more preferably two methine groups. Especially, a hydrogen atom of the mechine group is preferably substituted by any one of $L_1$, $L_2$, $L_3$, $R_1$, $R_2$ and $R_3$.

Examples of such divalent 5-membered cyclic groups include thiophene-2,5-diyl, furan-2,5-diyl, oxazole-2,5-diyl, imidazole-2,5-diyl, 1,3,4-oxadiazole-2,5-diyl and tetrahydrofuran-2,4-diyl.

The divalent 5-membered cyclic group may have a substituent. As for such substituents, same substituents as those described in $Y_{11}$, $Y_{12}$ and $Y_{13}$ can be mentioned.

In the formula (D-2), $R_1$, $R_2$ and $R_3$ each independently represent an alkyl group (for example, a methyl group, an ethyl group, an isopropyl group or a tert-butyl group), an alkenyl group (for example, a vinyl group, an allyl group, a 2-butenyl group or 3-pentenyl group), an alkynyl group (for example, a propargyl group or a 3-pentynyl group), an aryl group (for example, a phenyl group, a p-methylphenyl group or a naphthyl group), a substituted or unsubstituted amino group (for example, an unsubstituted amino group, a methylamino group, a dimethylamino group, a diethylamino group or an anilino group), an alkoxy group (for example, a methoxy group, an ethoxy group or a butoxy group), an aryloxy group (for example, a phenyloxy group or 2-naphthyloxy group), an acyl group (for example, an acetyl group, a benzoyl group, a formyl group or a pivaloyl group), an alkoxycarbonyl group (for example, a methoxycarbonyl group or an ethoxycarbonyl group), an aryloxycarbonyl group (for example, a phenyloxycarbonyl group), an acyloxy group (for example, an acetoxy group or a benzoyloxy group), an acylamino group (for example, an acetylamino group or a benzoylamino group), an alkoxycarbonylamino group (for example, a methoxycarbonylamino group), an aryloxycarbonylamino group (for example, a phenyloxycarbonylamino group), an alkylsulfonylamino group (for example, a methane sulfonylamino group), an arylsulfonylamino group (for example, a benzene sulfonylamino group), a sulfamoyl group (for example, a sulfamoyl group, an N-methyl sulfamoyl group, an N,N-dimethylsulfamoyl group or an N-phenylsulfamoyl group), a carbamoyl group (for example, an unsubstituted carbamoyl group, an N-methylcarbamoyl group, an N,N-diethylcarbamoyl group or an N-phenylcarbamoyl group), an alkylthio group (for example, a methylthio group, an ethylthio group), an arylthio group (for example, a phenylthio group), an alkylsulfonyl group (for example, a mesyl group), an arylsulfonyl group (for example, a tosyl group), an alkylsulfinyl group (for example, a methane sulfinyl group), an arylsulfinyl group (a benzene sulfinyl group), an ureido group (for example, an unsubstituted ureido group, a 3-methylureido group or a 3-phenylureido group), a phosphoric acid amido group (for example, a diethyl phosphoric acid amido group or a phenyl phosphoric acid amido group), a hydroxyl group, a mercapto group, a halogen atom (for example, a fluorine atom, a chlorine atom, a bromine atom or an iodine atom), a cyano group, a sulfo group, a carboxyl group, a nitro group, a hydroxamic acid group, a sulfino group, a hydrazino group, an imino group, a heterocyclic group (namely, a heterocyclic group containing a hetero atom such as a nitrogen atom, an oxygen atom or a sulfur atom, for example, an imidazolyl group, a pyridyl group, a quinolyl group, a furyl group, a piperidyl group, a morpholino group, benzoxazolyl group, a benzimidazolyl group or a benzothiazolyl group) and a silyl group (for example, a trimethylsilyl group or a triphenylsilyl group). These substituents may each independently be further substituted by any one of these substituents.

It is more preferable that $R_1$, $R_2$ and $R_3$ are each independently represented by the following formula (III):

*-L$_{11}$-Q,                                            Formural (III):

wherein * denotes a position to be bonded to $H_1$, $H_2$ or $H_3$ in the formula (D-2).

Q each independently represents a polymerizable group or a methyl group. When a compound represented by the formula (D-2) is used in an optical film like an optical compensatory film, inclusive of a retardation film, in which a magnitude of a phase difference is preferably not changed by heat, Q is preferably a polymerizable group. A polymerization reaction is an addition polymerization (inclusive of ring-opening polymerization) or condensation polymerization. In other words, the polymerizable group is preferably a functional group capable of performing an addition polymerization reaction or a condensation polymerization reaction. Examples of such polymerizable groups are set forth below.

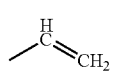

q1

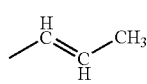

q2

-continued

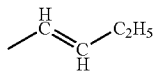 q3

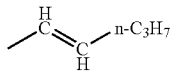 q4

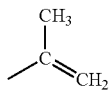 q5

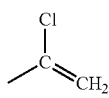 q6

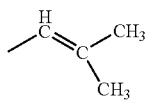 q7

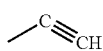 q8

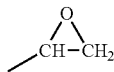 q9

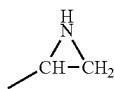 q10

—SH q11

—OH q12

—NH₂ q13

 q14

 q15

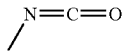 q16

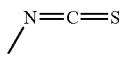 q17

Among these examples, q1 to q10 are preferable, and q1 to q8 are more preferable.

Further, the polymerizable group is particularly preferably a functional group capable of performing an addition polymerization reaction. As for such polymerizable group as described above, an ethylenic unsaturated group or a ring-opening polymerizable group is preferable.

Examples of such ethylenic unsaturated groups include compounds represented by the following formulas (M-1) to (M-6)

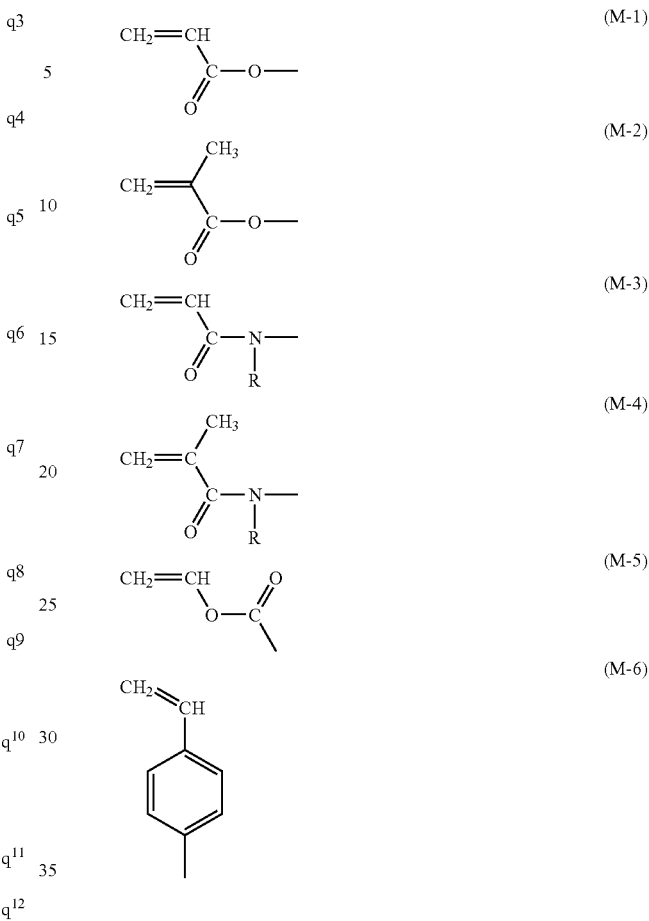

In the formulas (M-3) and (M-4), R represents a hydrogen atom or an alkyl group. As for R, a hydrogen atom or a methyl group is preferable.

Among the formulas (M-1) to (M-6), the formula (M-1) or (M-2) is preferable, and the formula (M-1) is most preferable.

The ring-opening polymerizable group is preferably a cyclic ether group, more preferably an epoxy group or an oxetanyl group, and most preferably an epoxy group.

In the formula (III), $L_{11}$ represents a divalent linking group. $L_{11}$ is preferably at least one divalent linking group selected from the group consisting of —O—, —S—, —C(=O)—, —NR$_7$—, a divalent chain group and a divalent cyclic group. $R_7$ represents an alkyl group having from 1 to 7 carbon atoms or a hydrogen atom, in which an alkyl group having from 1 to 4 carbon atoms or a hydrogen atom is preferable, and a methyl group, an ethyl group or a hydrogen atom is more preferable and a hydrogen atom is most preferable.

The divalent chain group is an alkylene group, a substituted alkylene group, an alkenylene group, a substituted alkenylene group, an alkynylene group or a substituted alkynylene group. Among these groups, an alkylene group, a substituted alkylene group, an alkenylene group or a substituted alkenylene group is preferable, and an alkylene group or an alkenylene group is more preferable.

The alkylene group as a divalent chain group represented by $L_{11}$ may have a branch. The number of carbon atoms of the alkylene group is preferably from 1 to 16, more preferably from 2 to 14 and, most preferably, from 2 to 12. An alkylene moiety of a substituted alkylene group is same as that of the aforementioned alkylene group. Examples of such substituents include a halogen atom.

The alkenylene group as a divalent chain group represented by $L_{11}$ may have a substituted or unsubstituted alkylene group in a main chain, or a branch. The number of carbon atoms of the alkenylene group is preferably from 2 to 16, more preferably from 2 to 14, and most preferably from 2 to 12. An alkenylene moiety of a substituted alkenylene group is same as that of the aforementioned alkenylene group. Examples of such substituents include a halogen atom.

The alkynylene group as a divalent chain group represented by $L_{11}$ may have a substituted or unsubstituted alkylene group in a main chain. The number of carbon atoms of the alkynylene group is preferably from 2 to 16, more preferably from 2 to 14, and most preferably from 2 to 12. An alkynylene moiety of a substituted alkynylene group is same as that of the aforementioned alkynylene group. Examples of such substituents include a halogen atom.

Specific examples of the divalent chain group represented by $L_{11}$ include ethylene, trimethylene, tetramethylene, 1-methyl-1,4-butylene, pentamethylene, hexamethylene, octamethylene, nonamethylene, decamethylene, undecamethylene, dodecamethylene, 2-butenylene and 2-butynylene.

The divalent cyclic group represented by $L_{11}$ is a divalent linking group having at least one cyclic structure. The divalent cyclic group is preferably a 5-membered, 6-membered or 7-membered ring, more preferably 5-membered or 6-membered ring, and most preferably 6-membered ring. The ring contained in the cyclic group may be a condensed ring. However, a single ring is more preferable than the condensed ring. Further, the ring contained in the cyclic group may be any one of an aromatic ring, an aliphatic ring and a heterocycle. Examples of aromatic rings include a benzene ring and a naphthalene ring. Examples of aliphatic rings include a cyclohexane ring. Examples of heterocycles include a pyridine ring and a pyrimidine ring.

Among divalent cyclic groups represented by $L_{11}$, as for the cyclic group having a benzene ring, 1,4-phenylene is preferable. As for the cyclic group having a naphthalene ring, naphthalene-1,5-diyl or naphthalene-2,6-diyl is preferable. As for the cyclic group having a cyclohexane ring, 1,4-cyclohexylene is preferable. As for the cyclic group having a pyridine ring, pyridine-2,5-diyl is preferable. As for the cyclic group having a pyrimidine ring, pyrimidine-2,5-diyl is preferable.

The divalent cyclic group represented by $L_{11}$ may have a substituent. Examples of such substituents include a halogen atom, a cyano group, a nitro group, an alkyl group having from 1 to 16 carbon atoms, a halogen-substituted alkyl group having from 1 to 16 carbon atoms, an alkoxy group having from 1 to 16 carbon atoms, an acyl group having from 2 to 16 carbon atoms, an alkylthio group having from 1 to 16 carbon atoms, an acyloxy group having from 2 to 16 carbon atoms, an alkoxycarbonyl group having from 2 to 16 carbon atoms, a carbamoyl group, an alkyl-substituted carbamoyl group having from 2 to 16 carbon atoms and an acylamino group having from 2 to 16 carbon atoms.

It is further preferable that $R_1$, $R_2$ and $R_3$ are each independently represented by the following formula (IV):

$$\text{*-}L_{21}\text{-divalent cyclic group-}L_{22}\text{-}Q_1, \quad \text{Formula (IV):}$$

wherein * denotes a position to be bonded to $H_1$, $H_2$ or $H_3$ in the formula (D-2).

$Q_1$ has a same definition as that of Q in the formula (III).

$L_{21}$ is a single bond or a divalent linking group. When $L_{21}$ is the divalent linking group, the divalent linking group is preferably at least one divalent group selected from the group consisting of —O—, —S—, —C(=O)—, —NR$_7$—, —CH=CH— and —C≡C—. R$_7$ represents an alkyl group having from 1 to 7 carbon atoms or a hydrogen atom, in which an alkyl group having from 1 to 4 carbon atoms or a hydrogen atom is preferable, and a methyl group, an ethyl group or a hydrogen atom is more preferable, and a hydrogen atom is most preferable.

As for $L_{21}$, a single bond, *—O—CO—, *—CO—O—, *—CH=CH— and *—C≡C— (in this occasion, * denotes that in the formula (IV)) is preferable.

The divalent cyclic group in the formula (IV) has a same definition as that of the divalent cyclic group in the formula (III).

In the formula (IV), $L_{22}$ has a same definition as that of $L_{11}$ in the formula (III).

Examples of the divalent linking groups represented by $L_{22}$ are set forth below. In the examples, respective right sides thereof are bonded to the divalent cyclic group in the formula (IV), while respective left sides thereof are bonded to $Q_1$.

L-1: -divalent chain group-O-divalent cyclic group-
L-2: -divalent chain group-O-divalent cyclic group-CO—O—
L-3: -divalent chain group-O-divalent cyclic group-O—CO—
L-4: -divalent chain group-O-divalent cyclic group-CO—NR$_7$—
L-5: -divalent chain group-O-divalent cyclic group-divalent chain group-
L-6: -divalent chain group-O-divalent cyclic group-divalent chain group-CO—O—
L-7: -divalent chain group-o-divalent cyclic group-divalent chain group-O—CO—
L-8: -divalent chain group-O—CO-divalent cyclic group-
L-9: -divalent chain group-O—CO-divalent cyclic group-CO—O—
L-10: -divalent chain group-O—CO-divalent cyclic group-O—CO—
L-11: -divalent chain group-O—CO-divalent cyclic group-CO—NR$_7$—
L-12: -divalent chain group-O—CO-divalent cyclic group-divalent chain group-
L-13: -divalent chain group-O—CO-divalent cyclic group-divalent chain group-CO—O—
L-14: -divalent chain group-O—CO-divalent cyclic group-divalent chain group-O—CO—
L-15: -divalent chain group-CO—O-divalent cyclic group-
L-16: -divalent chain group-CO—O-divalent cyclic group-CO—O—
L-17: -divalent chain group-CO—O-divalent cyclic group-O—CO—
L-18: -divalent chain group-CO—O-divalent cyclic group-CO—NR$_7$—
L-19: -divalent chain group-CO—O-divalent cyclic group-divalent chain group-
L-20: -divalent chain group-CO—O-divalent cyclic group-divalent chain group-CO—O—
L-21: -divalent chain group-CO—O-divalent cyclic group-divalent chain group-O—CO—
L-22: -divalent chain group-O—CO—O-divalent cyclic group-
L-23: -divalent chain group-O—CO—O-divalent cyclic group-CO—O—

L-24: -divalent chain group-O—CO—O-divalent cyclic group-O—CO—
L-25: -divalent chain group-O—CO—O-divalent cyclic group-CO—NR$_7$—
L-26: -divalent chain group-O—CO—O-divalent cyclic group-divalent chain group-
L-27: -divalent chain group-O—CO—O-divalent cyclic group-divalent chain group-CO—O—
L-28: -divalent chain group-O—CO—O-divalent cyclic group-divalent chain group-O—CO—
L-29: -divalent chain group-
L-30: -divalent chain group-O—
L-31: -divalent chain group-CO—O—
L-32: -divalent chain group-O—CO—
L-33: -divalent chain group-CO—NR$_7$—
L-34: -divalent chain group-O-divalent chain group-
L-35: -divalent chain group-O-divalent chain group-O—
L-36: -divalent chain group-O-divalent chain group-CO—O—
L-37: -divalent chain group-O-divalent chain group-O—CO—

Among these examples, L-2, L-3, L-9, L-10, L-16, L-17, L-23, L-24, L-30, L-31, L-32, L-35, L-36 or L-37 is preferable.

It is most preferable that $R_1$, $R_2$ and $R_3$ are each independently represented by the following formula (V):

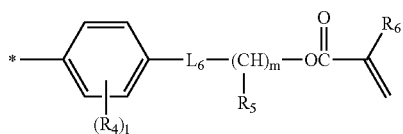

wherein * denotes a position to be bonded to $H_1$, $H_2$ or $H_3$ in the formula (D-2).

$R_4$ represents a halogen atom (preferably, a fluorine atom, a chlorine atom, a bromine atom or an iodine atom), an alkyl group having from 1 to 8 carbon atoms, an alkyloxy group having from 1 to 8 carbon atoms, an acyl group having from 2 to 8 carbon atoms, an acyloxy group having from 2 to 8 carbon atoms, an alkoxycarbonyl group having from 2 to 8 carbon atoms, a nitro group or a cyano group. Among these, a halogen atom, an alkyl group having from 1 to 3 carbon atoms, an alkyloxy group having from 1 to 3 carbon atoms, an acyl group having from 2 to 4 carbon atoms, an alkoxycarbonyl group having from 2 to 4 carbon atoms or a cyano group is preferable.

l represents an integer of from 0 to 4, in which 0 or 1 is preferable, and 0 is most preferable. When l represents 2 or more, plural groups represented by $R_4$ each maybe different from one another.

$L_6$ represents —O—, —CO—O, —O—CO—, —O—CO—O or —CH$_2$—, in which  denotes a position to be bonded to the benzene ring in the formula (V).

$R_5$ represents a hydrogen atom, a methyl group, an ethyl group or a propyl group, in which a hydrogen atom or a methyl group is more preferable, and a hydrogen atom is most preferable.

m represents an integer of from 2 to 16, in which an integer of from 2 to 12 is preferable.

$R_6$ represents a hydrogen atom or a methyl group, in which a hydrogen atom is preferable.

As for the liquid crystalline compound used for the liquid crystalline composition D which exhibits a liquid crystal phase satisfying the numerical formula (II), a compound represented by the following formula (I) is most preferable:

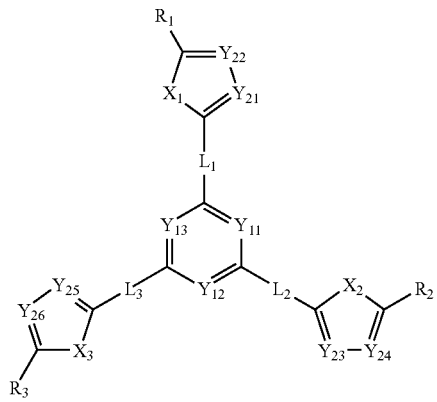

wherein $Y_{11}$, $Y_{12}$, $Y_{13}$, $Y_{21}$, $Y_{22}$, $Y_{23}$, $Y_{24}$, $Y_{25}$ and $Y_{26}$ each independently represent a methine group or a nitrogen atom.

When $Y_{11}$, $Y_{12}$, $Y_{13}$, $Y_{21}$, $Y_{22}$, $Y_{23}$, $Y_{24}$, $Y_{25}$ and $Y_{26}$ each independently represent a methine group, the methine group may have a substituent. Examples of such substituents are same as those of $Y_{11}$, $Y_{12}$ and $Y_{13}$ in the formula (D-2).

In the formula (I), $X_1$, $X_2$ and $X_3$ each independently represent an oxygen atom, a sulfur atom, a methylene group or an imino group. When $X_1$, $X_2$ and $X_3$ each independently represent a methylene group or an imino group, they may have a substituent. As for such substituents, those as described in the methine group are preferable. These substituents may further be substituted; in this occasion, such substituents are same as those which the substituents of the methine group may have.

In the formula (I), definitions and favorable examples of $L_1$, $L_2$ and $L_3$ are same as those in the formula (D-2), respectively.

In the formula (I), definitions and favorable examples of $R_1$, $R_2$ and $R_3$ are same as those in the formula (D-2), respectively. According to the present invention, among compounds represented by the formula (I), compounds represented by the formula (II) in which $R_1$, $R_2$ and $R_3$ are each independently represented by the formula (V) are preferable.

As for the liquid crystal phase which the compound represented by the formula (I) and the liquid crystalline composition containing the compound exhibit, the liquid crystal phase which is referred to as satisfying the numerical formula (II) can be mentioned. Among these phases, the columnar phase or the discotic nematic phase is preferable and, particularly, the dichotic nematic phase is preferable. The liquid crystal phase is preferably exhibited at a temperature of from 30 to 300° C., more preferably at a temperature of form 50 to 250° C.

Specific examples of compounds represented by the formula (I) or (II) are set forth below, but the present invention is not limited thereto.

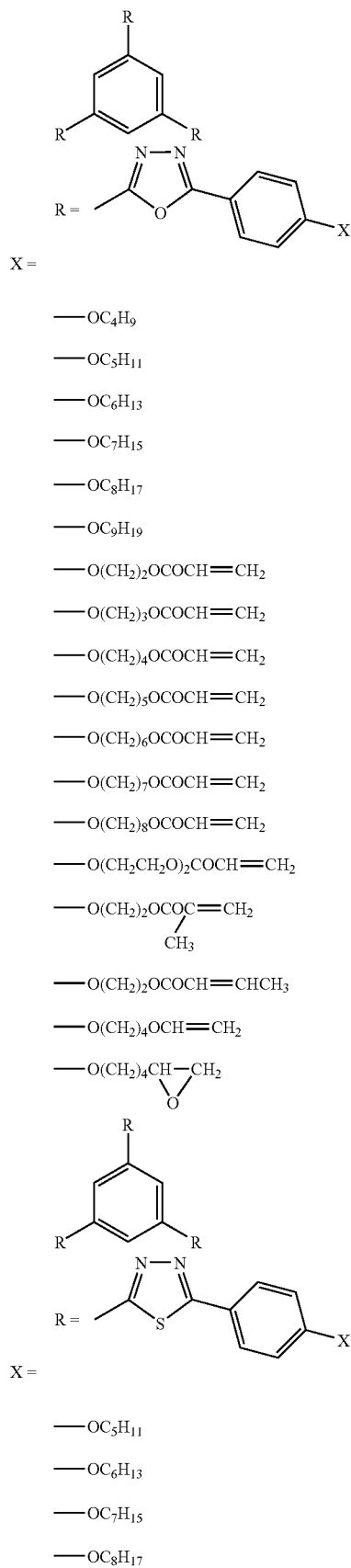

R =  —CH₃

X =

| | |
|---|---|
| —OC₄H₉ | D-1 |
| —OC₅H₁₁ | D-2 |
| —OC₆H₁₃ | D-3 |
| —OC₇H₁₅ | D-4 |
| —OC₈H₁₇ | D-5 |
| —OC₉H₁₉ | D-6 |
| —O(CH₂)₂OCOCH=CH₂ | D-7 |
| —O(CH₂)₃OCOCH=CH₂ | D-8 |
| —O(CH₂)₄OCOCH=CH₂ | D-9 |
| —O(CH₂)₅OCOCH=CH₂ | D-10 |
| —O(CH₂)₆OCOCH=CH₂ | D-11 |
| —O(CH₂)₇OCOCH=CH₂ | D-12 |
| —O(CH₂)₈OCOCH=CH₂ | D-13 |
| —O(CH₂CH₂O)₂COCH=CH₂ | D-14 |
| —O(CH₂)₂OCOC(CH₃)=CH₂ | D-15 |
| —O(CH₂)₂OCOCH=CHCH₃ | D-16 |
| —O(CH₂)₄OCH=CH₂ | D-17 |
| —O(CH₂)₄CH(O)CH₂ (epoxide) | D-18 |

(thiadiazole structure with R on benzene, R = —CH₃)

X =

| | |
|---|---|
| —OC₅H₁₁ | D-19 |
| —OC₆H₁₃ | D-20 |
| —OC₇H₁₅ | D-21 |
| —OC₈H₁₇ | D-22 |
| —O(CH₂)₂OCOCH=CH₂ | D-23 |
| —O(CH₂)₃OCOCH=CH₂ | D-24 |
| —O(CH₂)₄OCOCH=CH₂ | D-25 |
| —O(CH₂CH₂O)₂COCH=CH₂ | D-26 |
| —O(CH₂)₂OCOC(CH₃)=CH₂ | D-27 |
| —O(CH₂)₄OCH=CH₂ | D-28 |
| —O(CH₂)₄CH(O)CH₂ (epoxide) | D-29 |

(thiophene structure with R on benzene, R = —CH₃)

X =

| | |
|---|---|
| —OC₅H₁₁ | D-30 |
| —OC₆H₁₃ | D-31 |
| —OC₇H₁₅ | D-32 |
| —OC₈H₁₇ | D-33 |
| —O(CH₂)₂OCOCH=CH₂ | D-34 |
| —O(CH₂)₃OCOCH=CH₂ | D-35 |
| —O(CH₂)₄OCOCH=CH₂ | D-36 |
| —O(CH₂CH₂O)₂COCH=CH₂ | D-37 |
| —O(CH₂)₂OCOC(CH₃)=CH₂ | D-38 |
| —O(CH₂)₄OCH=CH₂ | D-39 |
| —O(CH₂)₄CH(O)CH₂ (epoxide) | D-40 |

(furan structure with R on benzene, R = —CH₃)

X =

| | |
|---|---|
| —OC₅H₁₁ | D-41 |
| —OC₆H₁₃ | D-42 |
| —OC₇H₁₅ | D-43 |

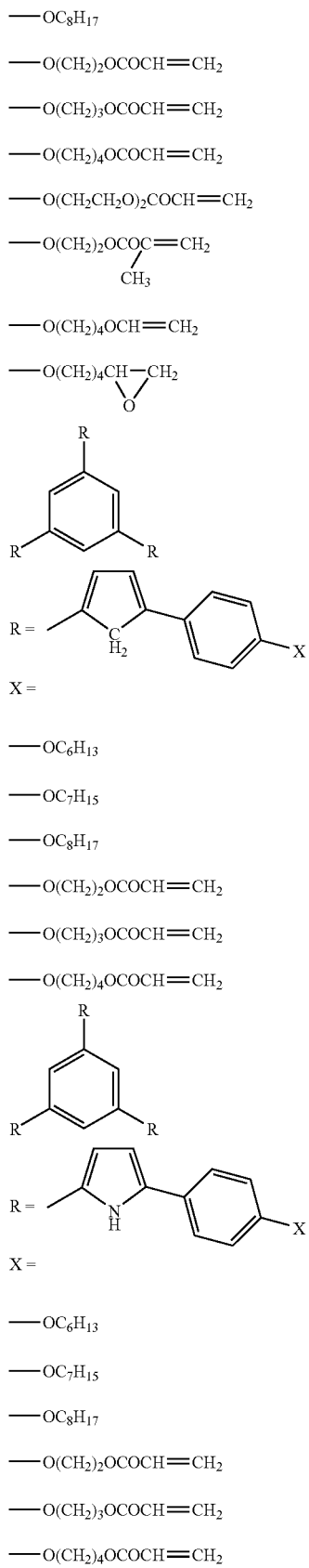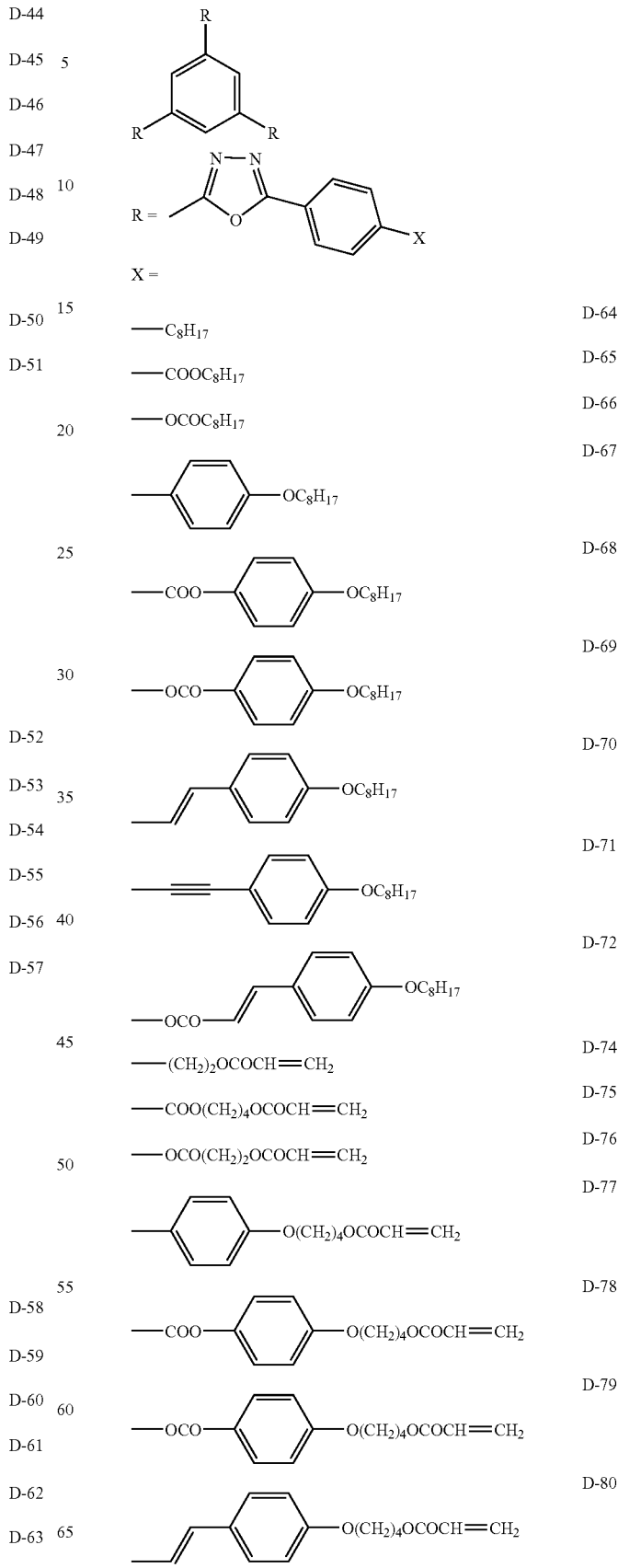

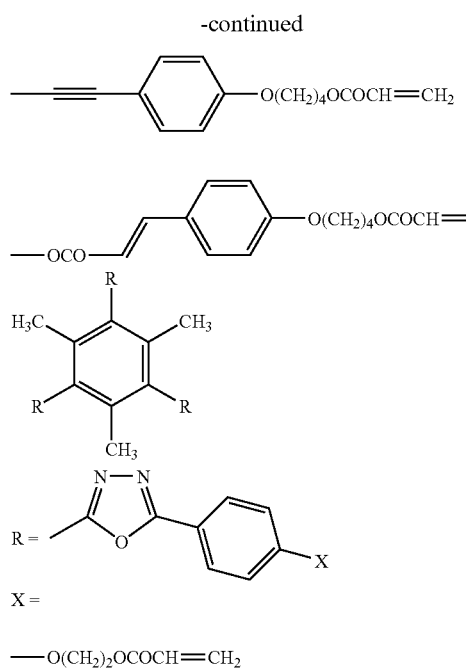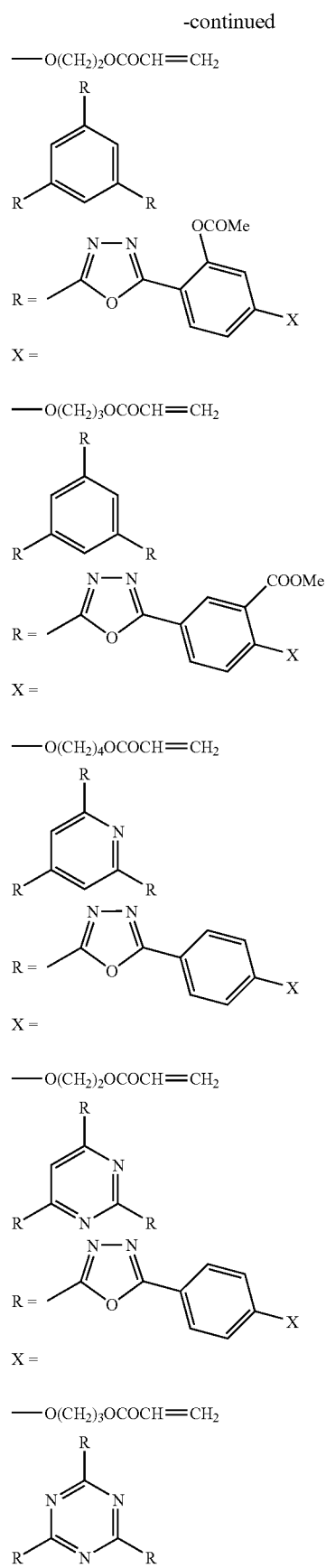

-continued
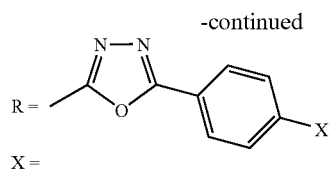
X =
—O(CH₂)₄OCOCH=CH₂  D-91
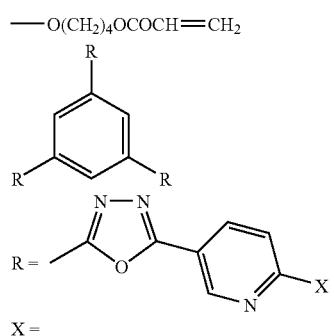
X =
—O(CH₂)₂OCOCH=CH₂  D-92
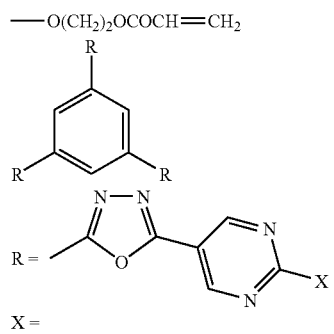
X =
—O(CH₂)₃OCOCH=CH₂  D-93
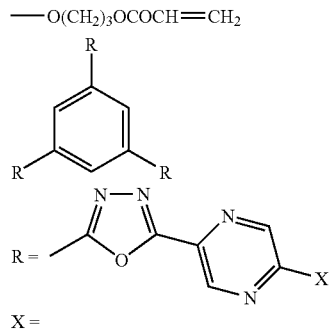
X =
—O(CH₂)₄OCOCH=CH₂  D-94
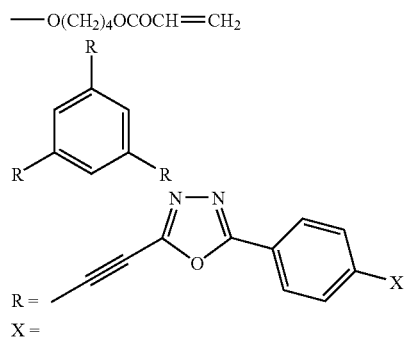
X =
—O(CH₂)₂OCOCH=CH₂  D-95
—OC₆H₁₃  D-96
-continued
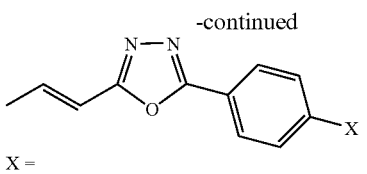
X =
—O(CH₂)₂OCOCH=CH₂  D-97
—OC₆H₁₃  D-98
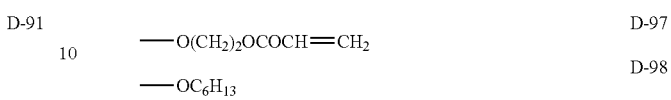
X =
—O(CH₂)₂OCOCH=CH₂  D-99
—OC₆H₁₃  D-100
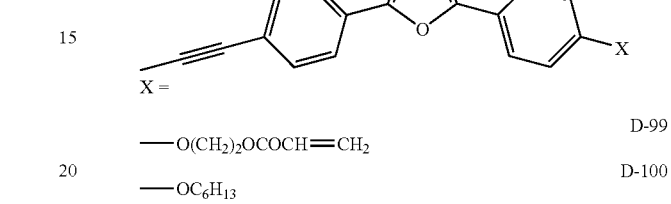
X =
—O(CH₂)₂OCOCH=CH₂  D-101
—OC₆H₁₃  D-102
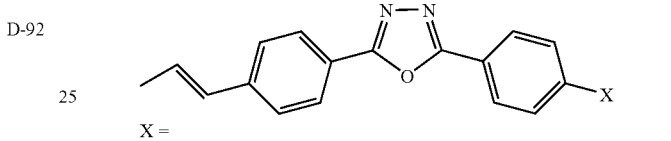
X =
—O(CH₂)₂OCOCH=CH₂  D-103
—OC₆H₁₃  D-104
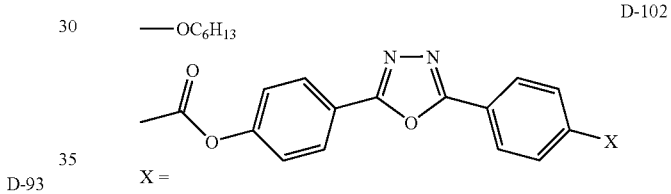
X =
—O(CH₂)₂OCOCH=CH₂  D-105
—OC₆H₁₃  D-106
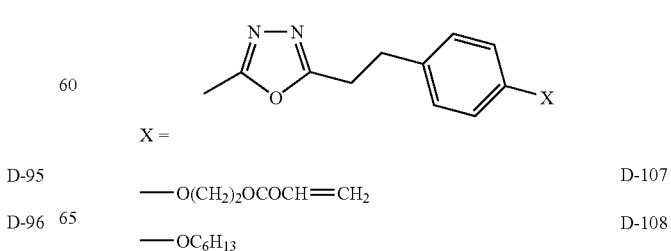
X =
—O(CH₂)₂OCOCH=CH₂  D-107
—OC₆H₁₃  D-108

-continued

R =

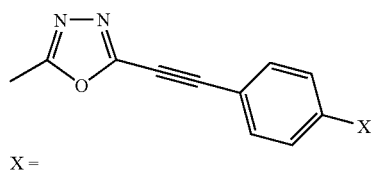

X =

—O(CH$_2$)$_2$OCOCH=CH$_2$  D-109
—OC$_6$H$_{13}$  D-110

R =

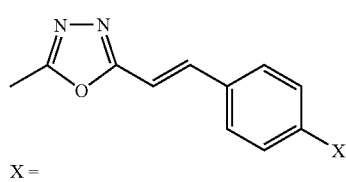

X =

—O(CH$_2$)$_2$OCOCH=CH$_2$  D-111
—OC$_6$H$_{13}$  D-112

R =

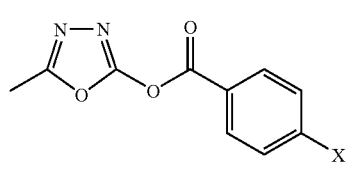

X =

—O(CH$_2$)$_2$OCOCH=CH$_2$  D-113
—OC$_6$H$_{13}$  D-114

R =

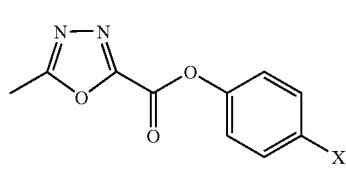

X =

—O(CH$_2$)$_2$OCOCH=CH$_2$  D-115
—OC$_6$H$_{13}$  D-116

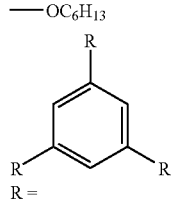

R =

X =

—O(CH$_2$)$_2$OCOCH=CH$_2$  D-117

-continued

R =

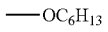

X =

—O(CH$_2$)$_2$OCOCH=CH$_2$  D-118
—OC$_6$H$_{13}$  D-119

R =

—O(CH$_2$)$_2$OCOCH=CH$_2$  D-120

—OC$_6$H$_{13}$  D-121

R =

X =

—O(CH$_2$)$_2$OCOCH=CH$_2$  D-122
—OC$_6$H$_{13}$  D-123

R =

X =

—O(CH$_2$)$_2$OCOCH=CH$_2$  D-124
—OC$_6$H$_{13}$  D-125

R =

—O(CH$_2$)$_2$OCOCH=CH$_2$  D-126

R =

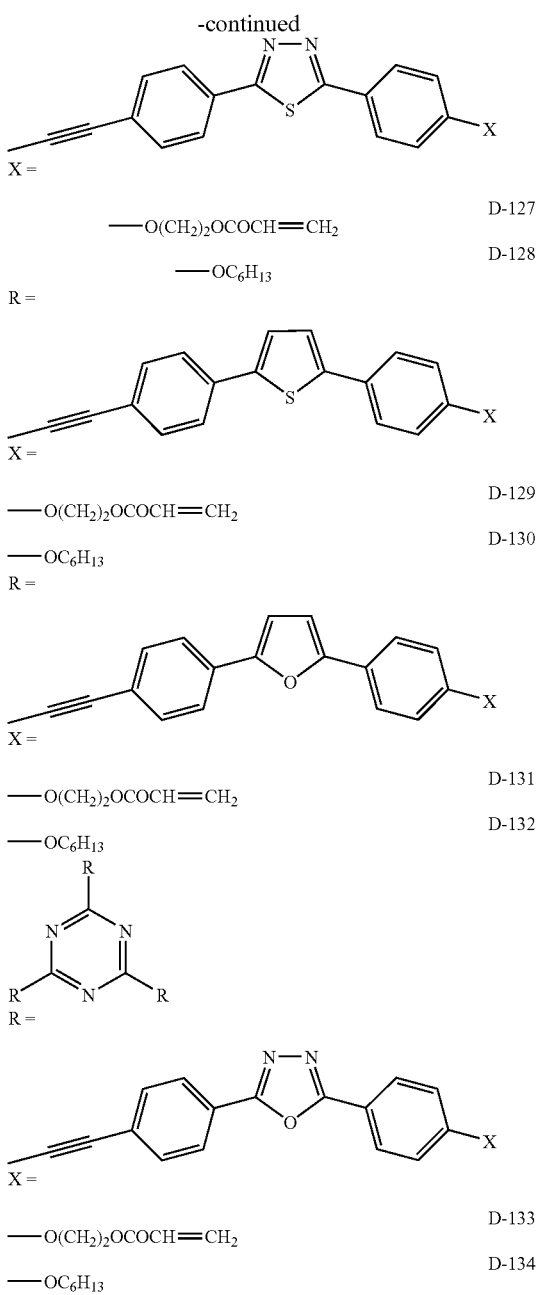

(Liquid Crystalline Composition Comprising Liquid Crystalline Composition R and Liquid Crystalline Composition D)

It is preferable that a liquid crystalline composition according to the present invention, comprising a liquid crystalline composition R which exhibits a liquid crystal phase satisfying the numerical formula (I) and a liquid crystalline composition D which exhibits a liquid crystal phase satisfying the numerical formula (II), exhibits a liquid crystal phase in a mixed state of the liquid crystalline composition R and the liquid crystalline composition D, at any mixing ratio of the liquid crystalline composition R to the liquid crystalline composition D.

According to the present invention, when the liquid crystalline composition exhibits a liquid crystal phase in a mixed state of the liquid crystalline composition R and the liquid crystalline composition D, at any mixing ratio of the liquid crystalline composition R to the liquid crystalline composition D, the liquid crystalline composition R and the liquid crystalline composition D are allowed to be in a state of being mixed with each other without causing phase separation therebetween at any mixing ratio, and the liquid crystal phase is exhibited in the state. Therefore, for example, as described in R. Pratiba et al, *Molecular Cryastals and Liquid Crystals*, Vol. 1, page 111 (1985), a case in which a liquid crystal phase is exhibited in a state of a phase separation between the crystalline composition R and the liquid crystalline composition D is excluded from the present invention.

The fact that the liquid crystalline composition according to the present invention, comprising the liquid crystalline composition R and the liquid crystalline composition D, can exhibit a liquid crystal phase in a mixed state of the liquid crystalline composition R and the liquid crystalline composition D at any mixing ratio therebetween can be proved by performing a contact test (described in, for example, "*Ekisho Binran (Handbook of Liquid Crystals)*", Chapter 2, page 156, Maruzen (2000)) of the liquid crystalline composition which exhibits the liquid crystal phase satisfying the numerical formula (I) with the liquid crystalline composition which exhibits the liquid crystal phase satisfying the numerical formula (II). Namely, such proving can be conducted by observing, under a polarizing microscope, presence or absence of the liquid crystallinity in an area in which two types of liquid crystalline compositions are mixed with each other. In the contact test, so long as the liquid crystallinity can be noticed in an entire area, the liquid crystallinity can be exhibited at any mixing ratio between the two types of liquid crystalline compositions.

The liquid crystalline composition according to the present invention, comprising the liquid crystalline composition R and the liquid crystalline composition D, can exhibit a liquid crystal phase, in a mixed state of the liquid crystalline composition R and the liquid crystalline composition D, in the range of preferably from 20° C. to 300° C., more preferably from 40° C. to 280° C., and most preferably from 60° C. to 250° C. The term "exhibit a liquid crystal phase in the range of from 20° C. to 300° C." means to include a case in which the liquid crystal phase is exhibited in the range of temperature crossing over 20° C. (specifically, for example, in the range of from 10° C. to 22° C.) or 300° C. (specifically, for example, in the range of from 298° C. to 310° C.). The same can be said regarding the temperature ranges of from 40° C. to 280° C. and from 60° C. to 250° C.

The liquid crystalline composition according to the present invention, comprising the liquid crystalline composition R and the liquid crystalline composition D, is preferably a liquid crystalline composition which exhibits an optically biaxial liquid crystal phase. The biaxial liquid crystal phase means a liquid crystal phase in which refractive indices nx, ny and nz in three axial directions are different from one another, for example, satisfy a relation of nx>ny>nz.

In the liquid crystalline composition according to the present invention, comprising the liquid crystalline composition R and the liquid crystalline composition D, a mixing ratio of the liquid crystalline composition R to the liquid crystalline composition D for exhibiting the biaxial liquid crystal phase can not clearly be defined since it differs from one occasion to another in accordance with molecular structures or molecular weights thereof; however, in terms of mass ratios, the ratio of liquid crystalline composition R to the liquid crystalline composition D is, preferably from 10 to 0.02, more preferably form 5 to 0.05, and most preferably from 2 to 0.1.

The biaxial liquid crystal phase is in many cases exhibited at a lower temperature than that of a uniaxial liquid crystal. For example, the uniaxial nematic phase (rod-like nematic phase or discotic nematic phase) is in many cases, transferred to a biaxial nematic phase by reducing the temperature thereof. There are many cases in which, when a content ratio of the liquid crystalline composition R is slightly increased over a given mixing ratio (the liquid crystalline composition R/the liquid crystalline composition D), transfer of the rod-like nematic phase to the biaxial nematic phase occurs with reduce of the temperature. Further, when a content ratio of the liquid crystalline composition D is slightly increased over the mixing ratio, transfer of the discotic nematic phase to the biaxial nematic phase occurs.

In the liquid crystalline composition according to the present invention, comprising the liquid crystalline composition R and the liquid crystalline composition D, when the uniaxial nematic phase exists at a high temperature side of the biaxial nematic phase, a value of $(nx-nz)/(nx-ny)$ of the biaxial liquid crystal phase can be controlled.

For example, when the rod-like nematic phase having a value of $(nx-nz)/(nx-ny)=1.0$ is subjected to a temperature reduce, the value of $(nx-nz)/(nx-ny)$ is not abruptly changed, but is in a tendency in which the value is gradually increased with temperature. Therefore, the value of $(nx-nz)/(nx-ny)$ can be controlled by selecting the temperature for fixing the alignment of the liquid crystalline compounds, such as polymerization by UV irradiation or the like. A controllable range of the value of $(nx-nz)/(nx-ny)$ at the time the rod-like nematic phase is transferred to the biaxial nematic phase can not uniformly defined since it differs from one occasion to another in accordance with molecular structures or the like of the liquid crystalline composition R and the liquid crystalline composition D; however, the range close to 1.0 is easily controlled. Specifically, the range of $1.0<(nx-nz)/(nx-ny)<10$ is easily controlled.

When the discotic nematic phase is transferred to the biaxial nematic phase, the value of $(nx-nz)/(nx-ny)$ can be controlled in the same way at the time the rod-like nematic phase is transferred to the biaxial nematic phase. In this case, the range of the value of $(nx-nz)/(nx-ny)$ close to $\infty$ is easily controlled. Specifically, the range of $1.2<(nx-nz)/(nx-ny)<\infty$ is easily controlled.

When the liquid crystalline composition according to the present invention, comprising the liquid crystalline composition R and the liquid crystalline composition D, exhibits an optically biaxial liquid crystal phase, while denoting the refractive indices in three directions of the biaxial liquid crystal phase as nx, ny and nz (nx>ny>nz), respective values preferably satisfy the numerical formula (III) described below and more preferably satisfy the numerical formula (VI) described below. By being the value of this range satisfied, an angle dependency of retardation of a liquid crystal display device can be controlled in accordance with the liquid crystal display device.

$$1.1 \leq (nx-nz)/(nx-ny) \leq 20 \quad \text{(III)},$$

$$1.2 \leq (nx-nz)/(nx-ny) \leq 10 \quad \text{(VI)}.$$

Further, it is desirous that the liquid crystalline composition according to the present invention, comprising the liquid crystalline composition R and the liquid crystalline composition D, not only has the aforementioned optical properties, but also performs a uniform defectless alignment (orientaiton) and exhibits a good monodomain property. If the monodomain property is bad, a polydomain structure results to cause alignment defects at the boundary between domains and in turn cause scattering of light. By exhibiting a good monodomain property, the retardation film tends to have a high light transmittance property.

As for the biaxial liquid crystal phase which is exhibited by the liquid crystalline composition according to the present invention, comprising the liquid crystalline composition R and the liquid crystalline composition D, a biaxial nematic phase, a biaxial smectic phase and a biaxial smectic C phase can be mentioned. Among these liquid crystal phases, the biaxial nematic phase (Nb phase) which exhibits a good monodomain property is preferable. The biaxial nematic phase is a type of liquid crystal phase which a nematic liquid crystalline compound can take, and when a space of the liquid crystal phase is defined by an x axis, a y axis and a z axis, the liquid crystalline compound is prohibited from performing a free rotation of an xz plane around the y axis, as well as a free rotation of an xy plane around the z axis.

Retardation Film

A retardation film according to the present invention comprises a transparent support and an optically anisotropic formed from a liquid crystalline composition according to the present invention. An alignment film is preferably provided between the transparent support and the optically anisotropic layer. The optically anisotropic layer can be obtained by optionally adding other additives to the liquid crystalline composition according to the present invention, applying the resultant composition on an alignment film and, then, fixing an alignment of liquid crystal compounds in a liquid crystal state.

Thickness of the optically anisotropic layer in the retardation film according to the present invention is preferably from 0.1 to 20 µm, more preferably from 0.2 to 15 µm, and most preferably from 0.5 to 10 µm.

The retardation film according to the present invention can be applied to an elliptically polarizing plate in combination with a polarizing film. Further, by being applied, in combination with the polarizing film, to a transmittance-type, reflective-type or semi-transmittance-type liquid crystal display device, it can contribute to enlargement of a viewing angle of the aforementioned devices.

Optically Anisotropic Layer

By forming an optically anisotropic layer through using the liquid crystalline composition according to the present invention, optical anisotropy of the optically anisotropic layer can be controlled so as to have an optically biaxial property in which principal values of refractive indices in three directions perpendicular to one another are different from one another. The principal values of the refractive indices in three direction of the optically anisotropic layer also satisfy the following numerical formula (III) and more preferably the following numerical formula (VI) in a same manner as in the refractive indices of the biaxial liquid crystal phase:

$$1.1 \leq (nx-nz)/(nx-ny) \leq 20 \quad \text{(III)},$$

$$1.2 \leq (nx-nz)/(nx-ny) \leq 10 \quad \text{(VI)}.$$

A biaxial retardation film formed from a biaxial liquid crystalline composition i on a transparent support and a uniaxial retardation film formed from a uniaxial liquid crystalline composition on a transparent support are different from each other in angle dependency of retardation. For example, in a retardation film using the uniaxial liquid crystalline composition, retardation in the normal direction to a film surface and retardation in the direction of a few dozens angles apart from the normal direction are greatly different from each other (the retardation becomes smaller, as it is inclined in the direction of a slow axis (phase retarding axis) more, while it becomes larger, as it is inclined in the direction of a fast axis (phase advancing axis) more). On the other hand, in a case of a biaxial liquid crystalline composition, a manner of the change of retardation differs from that of the uniaxial liquid crystalline composition. When a retardation film for use in various types of liquid crystal display devices is prepared, it is necessary to control the angle dependency of retardation in accordance with the liquid crystal display device; however, by using the biaxial liquid crystalline composition and, then, changing refractive indices of nx, ny and nz and orientations of respective axes, the angle dependency of the retardation can arbitrarily be controlled and, accordingly, the biaxial liquid crystalline composition is extremely useful.

The optical anisotropic layer can be formed by first once heating the liquid crystalline composition according to the present invention up to a liquid crystal phase-forming temperature and, then, cooling the thus-heated layer while maintaining the resulting aligned state while maintaining the resultant aligned state to fix an alignment form in the liquid crystal state without damaging the alignment form. Further, the optical anisotropic layer can be formed by heating a composition in which the liquid crystalline composition according to the present invention has been added with a polymerization initiator up to the liquid crystal phase-forming temperature, performing polymerization and, then, cooling to fix the alignment form in the liquid crystal state.

The fixed state according to the present invention, in which the alignment state is fixed, is most typically and most preferably a state in which the alignment form in t is maintained, but the fixed state is not limited thereto and specifically indicates a state in which the optically anisotropic layer does not exhibit flowability at a temperature range usually from 0° C. to 50° C., in severer conditions, from −30° C. to 70° C., and also the fixed alignment form can be stably maintained without causing any change in the alignment form due to external field or force. Further, at the time the optically anisotropic layer in which the alignment state is finally fixed has been formed, it is not necessary to allow the liquid crystal composition according to the present invention to exhibit liquid crystallinity. For example, since a liquid crystal compound having a polymerizable group is used, a polymerization or cross-linking reaction is progressed by heat, light or the like and, as a result, the compound is polymerized and may lose liquid crystallinity thereof.

Examples of additives which can be added to the liquid crystalline composition according to the present invention in forming the optically anisotropic layer include an air interface alignment controlling agent, an anti-shedding agent, a polymerization initiator and a polymerizable monomer.

Air Interface Alignment Controlling Agent

The liquid crystalline composition is aligned at the tilt angel at an air interface. For example, in a case of the biaxial liquid crystalline composition, there are three types of tilt angles in this tilt angle, namely, a sub-tilt angle formed by an nx refractive index direction and the air interface, another sub-tilt angle formed by an ny refractive index direction and the air interface, and still another sub-tilt angle formed by an nz refractive index direction and the air interface. When two types or more of the liquid crystalline compounds are contained in the liquid crystalline composition, since an extent of this tilt angle is changeable depending on a mixing ratio thereof, it is necessary to arbitrarily control the tilt angle at the air interface in accordance with applications.

In order to control the tilt angle, for example, although an outer field such as an electric field or a magnetic field can be applied or an additive can be added, an additive is preferably added. As for such additives, a compound which contains at least one group of a substituted or unsubstituted aliphatic group having from 6 to 40 carbon atoms or a substituted or unsubstituted aliphatic-substituted oligosiloxanoxy group having from 6 to 40 carbon atoms in the molecule is preferable and a compound which contains at least two group thereof is more preferable. For example, as for the air interface alignment controlling agent, a hydrophobic compound having an excluded volume effect as described in JP-A No. 2002-20363 can be used.

The amount added of the additive for controlling the alignment of the liquid crystalline composition in the air interface side is preferably from 0.001 to 20 mass %, more preferably from 0.01 to 10 mass %, and most preferably from 0.1 to 5 mass %, based on the liquid crystalline composition according to the present invention.

In general, as the material used together with the liquid crystalline compound for preventing the shedding at the coating of the liquid crystalline composition, a polymeric compound (polymer) can be suitably used.

Examples of such polymers are described in JP-A NO. 8-95030 and preferable specific examples thereof include cellulose esters. Examples of cellulose esters include cellulose acetate, cellulose acetate propionate, hydroxypropyl cellulose and cellulose acetate butyrate. In order to avoid interference of alignment of the liquid crystalline composition according to the present invention, an amount of the polymer used for the purpose of preventing the shedding is in the range of, based on the liquid crystalline composition according to the present invention, from 0.1 to 10% by mass, more preferably from 0.1 to 8% by mass, and still more preferably from 0.1 to 5% by mass.

Polymerization Initiator

According to the present invention, the liquid crystalline composition is preferably in a monodomain alignment, namely, fixed in a state in which it is substantially uniformly aligned. For this account, when a compound contained in the liquid crystalline composition R and/or the liquid crystalline composition D has a polymerizable group, polymerization is preferably performed by a polymerization reaction to fix the liquid crystalline composition. The polymerization reaction includes a thermal polymerization reaction using a thermal polymerization initiator, a photopolymerization reaction using a photopolymerization initiator, and a polymerization reaction by irradiating an electron beam and, in order to prevent a support or the like from being deformed or deteriorated in quality by heat, the photopolymerization reaction or the polymerization reaction by irradiating the electron beam is preferable.

Examples of photopolymerization initiators include an α-carbonyl compound (as described in U.S. Pat. Nos. 2,367,661 and 2,367,670), an acyloin ether (as described in U.S. Pat. No. 2,448,828), an α-hydrocarbon-substituted aromatic acyloin compound (as described in U.S. Pat. No. 2,722,512), a multi-nucleus quinone compound (as described in U.S. Pat. Nos. 3,046,127 and 2,951,758), a combination of tri-arylimidazole dimer and p-aminophenyl ketone (as described in U.S. Pat. No. 3,549,367), an acridine and a phenazine compound (as described in JP-A No. 60-105667 and U.S. Pat. No. 4,239,850) and an oxadiazole compound (as described in U.S. Pat. No. 4,212,970). An amount of the photopolymerization initiator is in the range of, based on a solid content of a coating liquid of the optically anisotropic layer, preferably from 0.01 to 20% by mass, and more preferably from 0.5 to 5% by mass.

Light irradiation for polymerization is performed by preferably using an ultraviolet ray. An irradiation energy is preferably from 10 mJ/cm$^2$ to 50 J/cm$^2$, and more preferably from 50 mJ/cm$^2$ to 800 mJ/cm$^2$. In order to accelerate the photopolymerization reaction, the light irradiation may be performed under a heating condition. Further, since an oxygen concentration in the atmosphere is concerned with a degree of polymerization, when a desired degree of polymerization is not attained in the air, an oxygen concentration is preferably reduced by being replaced by nitrogen or the like. The oxygen concentration is preferably 10% or less, more preferably 7% or less, and most preferably 3% or less.

Polymerizable Monomer

The liquid crystalline composition according to the present invention may be added with a polymerizable monomer. The polymerizable monomer usable in the present invention is not particularly limited, so long as it has compatibility with a compound contained in the liquid crystalline composition R and the liquid crystalline composition D, does not generate a tilt angle change of the liquid crystalline composition and does not inhibit the alignment of the liquid crystalline composition. Among these monomers, a compound having a polymerization-active ethylenic unsaturated group, for example, a vinyl group, a vinyloxy group, an acryloyl group, or methacryloyl group is preferably used. An amount of the aforementioned polymerizable monomer is in the range of, based on the liquid crystalline compound, ordinarily from 0.5 to 50% by mass, and preferably from 1 to 30% by mass. Further, in a case in which a monomer having 2 or more reactive functional groups is used, an effect to enhance adhesion between the alignment film and the optically anisotropic layer can be expected; the case is particularly favorable.

Coating Solvent

As for solvents used for preparing the liquid crystalline composition according to the present invention, an organic solvent is preferably used. Examples of such organic solvents include an amide (for example, N,N-dimethylformamide), a sulfoxide (for example, dimethylsulfoxide), a heterocyclic compound (for example, pyridine), a hydrocarbon (for example, toluene or hexane), an alkyl halide (for example, methyl acetate or butyl acetate), a ketone (for example, acetone, methyl ethyl ketone, methyl isobutyl ketone or cyclohexanone), an ether (for example, tetrahydrofuran or 1,2-dimethoxy ethane). An alkyl halide, an ester or a ketone is preferable. Two or more types of organic solvents may simultaneously be used.

Coating Method

The optically anisotropic layer is formed by first preparing a coating solution of the liquid crystalline composition according to the present invention by using any one of the aforementioned solvents, applying the thus-prepared coating solution on an alignment film and, then, subjecting the liquid crystalline composition according to the present invention to an alignment treatment. Application of the coating solution can be performed by a known method (for example, a wire bar coating method, an extruding coating method, a direct gravure coating method, a reverse gravure coating method or a direct coating method).

Alignment Film

An alignment film can be provided by, for example, subjecting an organic compound (preferable a polymer) to a rubbing treatment, obliquely evaporating an inorganic compound, forming a layer having a microgroove, or accumulating an organic compound (for example, ω-tricosanoic acid or stearyl acid methyl ester) by using a Langmuir-Blodgett method (LB film). Further, an alignment film which generates an alignment function by applying an electric field, applying a magnetic field or irradiating light is known.

The alignment film may be any type of film, so long as a desired alignment is provided to the liquid crystalline composition according to the present invention of the optically anisotropic layer provided on the alignment film; however, according to the present invention, the alignment film formed by performing a rubbing treatment or irradiating the light is preferable. The alignment film formed by subjecting the polymer to a rubbing treatment is particularly preferable. The rubbing treatment can ordinarily be performed by rubbing a surface of a polymer layer with paper or a cloth in a same direction several times and, particularly, according to the present invention, it is preferably performed in accordance with a method as described in "Ekisho Binran (*Handbook of Liquid Crystals*)" (Maruzen). Thickness of the alignment film is preferably from 0.01 to 10 μm, and more preferably from 0.05 to 3 μm.

Rubbing Density of Alignment Film

A relation between a rubbing density of the alignment film and a pre-tilt angle of the liquid crystalline compound at an interface facing the alignment film exists such that, as the rubbing density becomes higher, the pre-tilt angle becomes smaller, while, as the rubbing density becomes smaller, the pre-tilt angle becomes larger and, accordingly, the pre-tilt angle can be adjusted by changing the rubbing density of the alignment film.

As for methods for changing the rubbing density of the alignment film, a method as described in "*Ekisho Binran (Handbook of Liquid Crystals)*" edited by Editing Committee for Handbook of Liquid Crystals (Maruzen, 2000) can be used. The rubbing density (L) is quantified by the following formula (A):

$$L = Nl\{1+(2\pi rn/60v)\} \quad (A),$$

wherein N represents rubbing times; l represents a contact length of rubbing roller; r represents a radius of the roller; n represents rotation (rpm) of the roller; and v represents a transfer speed (second) of stage. For allowing the rubbing density to be higher, the rotation of the roller is allowed to be increased; the contact length of the rubbing roller is allowed to be longer; the radius of the roller is allowed to be larger; rotation of the roller is allowed to be larger; or the transfer speed of the stage is allowed to be lowered. For allowing the rubbing density to be lower, measures opposite to the aforementioned measures may be taken.

Transparent Support

As for a transparent support for the retardation film according to the present invention, a material therefor is not particularly limited, so long as it is mainly optically isotropic and has 80% or more of light transmittance, but a polymer film is preferable.

Films of such polymers, as specific examples, as cellulose acylates (for example, cellulose diacetate and cellulose triacetate), a norbornene-type polymer and poly (meth) acrylate esters can be mentioned. Many of polymers available in the market can also favorably be used. Among these polymers, from the standpoint of optical performance, cellulose esters are preferable, and lower fatty acid esters of cellulose are more preferable. The lower fatty acid is a fatty acid having 6 or less carbon atoms, and the number of carbon atoms is preferably 2 (cellulose acetate), 3 (cellulose propionate) or 4 (cellulose butyrate), and cellulose acetate is particularly preferable. A mixed fatty acid ester such as cellulose acetate propionate or cellulose acetate butyrate may be used. Further, even a polymer which easily exhibits birefringence such as polycarbonate or polysulfon which has conventionally been known can be used so long as the birefringence thereof is lowered by being modified by a molecule as described in WO00/26705.

Hereinafter, a cellulose acylate (particularly, cellulose triacetate) which is preferably used as a transparent support is described in detail.

As for the cellulose acylate, cellulose acetate having from 55.0 to 62.5% of acetylation degree is preferably used. Particularly, cellulose acetate having from 57.0 to 62.0% of acetylation degree is preferable. The acetylation degree means a bonded acetic acid volume per cellulose unit mass. The acetylation degree complies with a measurement and calculation of acetylation degree set by ASTM: D-817-91 (testing method of cellulose acetate and the like). A viscosity-average degree of polymerization (DP) of cellulose ester is preferably 250 or more, and more preferably 290 or more. Further, in the cellulose ester used for the present invention, a molecular weight distribution of Mw/Mn by a gel permeation chromatography (Mw represents mass average molecular weight while Mn represents number average molecular weight) is preferably narrow. A specific value of Mw/Mn is preferably from 1.0 t 1.7, more preferably from 1.3 to 1.65, and most preferably from 1.4 to 1.6.

In cellulose acylate, hydroxyl groups at the 2nd, 3rd, 6th position of cellulose are not evenly allotted with $\frac{1}{3}$ of an entire substitution degree, respectively, but the substitution degree of the hydroxyl group at the 6th position tends to be small. The substitution degree of the hydroxyl group at the 6th position of cellulose is preferably larger than those of the hydroxyl groups at the 2nd and 3rd positions. It is preferable that the hydroxyl group at the 6th position is substituted by an acyl group by 30 to 40% on the basis of the entire substitution degree, more preferably by 31% or more, and particularly preferably by 32% or more. The substitution degree at the 6th position is preferably 0.88 or more. The hydroxyl group at the 6th position may be substituted by any one of other acyl groups each having 3 or more carbon atoms (for example, propionyl, butylyl, valeroyl, benzoyl, acryloyl) than an acetyl group. The substitution degree at each position can be measured by NMR. Cellulose esters in which the substitution degree of the hydroxyl group at the 6th position is high can be synthesized with reference to a synthesis example 1 as described in JP-A No. 11-5851, paragraphs of from 0043 to 0044, a synthesis example 2 as described in a same publication, paragraphs of from 0048 to 0049 and a synthesis example 3 as described in a same publication, paragraphs of from 0051 to 0052.

In order to adjust the retardation, the polymer film used for the transparent support, particularly a cellulose acylate film, can comprise an aromatic compound having at least 2 aromatic rings as a retardation enhancing agent. When such retardation enhancing agent is used, the retardation enhancing agent is used in the range of, based on 100 parts by mass of cellulose acylate, from 0.01 to 20 parts by mass, preferably from 0.05 to 15 parts by mass, and more preferably from 0.1 to 10 parts by mass. Two types or more of aromatic compounds may simultaneously be used.

Examples of aromatic rings of the aromatic compounds include an aromatic hydrocarbon ring and an aromatic heterocycle.

The aromatic hydrocarbon ring is particularly preferably a 6-membered ring (namely, benzene ring).

The aromatic heterocycle is ordinarily an unsaturated heterocycle. The aromatic heterocycle is preferably a 5-membered ring, a 6-membered ring or a 7-membered ring, more preferably a 5-membered ring or a 6-membered ring. The aromatic heterocycle ordinarily has a highest number of double bonds. As for hetero atoms, a nitrogen atom, an oxygen atom or a sulfur atom is preferable, and a nitrogen atom is particularly preferable.

As for such aromatic rings, a benzene ring, a furan ring, a thiophene ring, a pyrrole ring, an oxazole ring, a thiazole ring, an imidazole ring, a triazole ring, a pyridine ring, a pyrimidine ring, a pyrazine ring or 1,3,5-triazine ring is preferable, and a benzene ring or 1,3,5-triazine ring is more preferable. The aromatic compound particularly preferably has at least one 1,3,5-triazine ring.

Examples of the aforementioned aromatic heterocycles include a furan ring, a thiophene ring, a pyrrole ring, an oxazole ring, an isooxazole ring, thiazole ring, an isothiazole ring, an imidazole ring, a pyrazole ring, a furazane ring, a triazole ring, a pyrane ring, a pyridine ring, a pyridazine ring, a pyrimidine ring, a pyrazine ring, and a 1,3,5-triazine ring.

The number of aromatic ring which the aromatic compound has is preferably from 2 to 20, more preferably from 2 to 12, still more preferably from 2 to 8, and most preferably from 2 to 6. A bonding relation between two aromatic rings can be classified to (a) a case of forming a condensed ring; (b) a case of directly bonding by a single bond; and (c) a case of bonding via a linking group (because of the aromatic ring, a spiro bond can not be formed). The bonding relation may be any one of (a) to (c) Such retardation enhancing agents as described above are described in WO01/88574A1, WO00/2619A1, JP-A Nos. 2000-11191 and 2000-275434 and Japanese Patent Application No. 2002-70009.

The cellulose acylate film is preferably produced from a prepared cellulose acylate solution (dope) by a solvent cast method. The dope may be added with the aforementioned retardation enhancing agent.

The dope is cast on a drum or band and, then, a solvent is evaporated, to thereby form a film. A concentration of the dope is preferably adjusted before being cast such that a solid content becomes from 18 to 35%. A surface of the drum or band is preferably subjected to mirror finish. Such casting and drying method of the solvent cast method are described in, for example, U.S. Pat. Nos. 2,336,310, 2,367,603, 2,492,078, 2,492,977, 2,492,978, 2,607,704, 2,739,069 and 2,739,070, GBP Nos. 640,731 and 736,892, JP-B Nos. 45-4554 and 49-5614, JP-A Nos. 60-176834, 60-203430 and 62-115035.

The aforementioned dope is preferably cast on the drum or band having a surface temperature of 10° C. or less. After cast on the drum or band, the dope is blown with a wind air for 2 seconds or more to be dried. The resultant film is, then, peeled, and further blown with a hot wind air in which temperatures are subsequently changed from 100° C. to 160° C. in order to evaporate the residual solvent. The aforementioned method is described in JP-B No. 5-17844. By performing the method, a period of time of from casting to peeling can be shortened. For performing this method, the cast dope must form a gel at the surface temperature of the drum or band.

By using the prepared cellulose acylate solution (dope), a film is formed by allowing the dope to be cast in 2 layers. The dope is cast on the drum or band and, then, the solvent is allowed to be evaporated to form a film. The concentration of the dope is preferably adjusted before being cast such that the solid content thereof becomes in the range of from 10 to 40%. The surface of the drum or band is preferably subjected to mirror finishing.

When a plurality of cellulose acylate solutions are cast to form two or more layers, for example, the solution containing cellulose acylate is allowed to be cast from a plurality of outlets which have been arranged at intervals along an advancing direction of the support in a stacking manner, to thereby form a laminated film. For example, methods as described in JP-A Nos. 61-158414, 1-122419 and 11-198285 are mentioned. Further, cellulose acylate solutions may be cast from two outlets to form a film. For example, JP-B No. 60-27562, JP-A Nos. 61-94724, 61-104813, 61-158413 and 6-134933. Further, a cast method, as described in JP-A No. 56-162617, in which a flow of high-viscous cellulose acetate solution may be enclosed with a low-viscous one and, then, the high- and low-viscous cellulose acetate solutions may simultaneously be extruded to form a cellulose acetate film may be used.

In the cellulose acylate film, the retardation can be adjusted by further performing a drawing treatment. A drawing ratio is preferably in the range of from 0 to 100%. When the cellulose acylate film used for the present invention is drawn, tenter drawing is favorably used and, in order to control the slow axis in a highly accurate manner, a difference between right- and left-clipping speeds, a difference between right- and left-releasing timings, or the like is preferably allowed to be as small as possible.

A plasticizer can be added to the cellulose acylate film to improve mechanical properties or to increase a drying speed. Examples of such plasticizers include a phosphoric acid ester and a carboxylic acid ester. Examples of such phosphoric acid esters include triphenyl phosphate (TPP), diphenylbiphenyl phosphate and tricresyl phosphate (TCP). Examples of such carboxylic acid esters include a phthalic acid ester and a citric acid ester. Examples of such phthalic acid esters include dimethyl phthalate (DMP), diethyl phthalate (DEP), dibutyl phthalate (DBP), dioctyl phthalate (DOP), diphenyl phthalate (DPP) and di-2-ethylhexyl phthalate (DEHP). Examples of such citric acid esters include triethyl o-acetylcitrate (OACTE) and tributyl o-acetylcitrate (OACTB). Examples of other carboxylic acid esters include butyl oleate, methylacetyl ricinolate, dibutyl sebacate and various types of trimellitic acid esters. Phthalic acid ester-type plasticizers (DMP, DEP, DBP, DOP, DPP, DEHP) are preferably used. Particularly preferred are DEP and DPP. An amount of the plasticizer is in the range, based on the amount of cellulose ester, of preferably from 0.1 to 25% by mass, more preferably from 1 to 20% by mass, and most preferably from 3 to 15% by mass.

A deterioration inhibitor (for example, an anti-oxidant, a peroxide decomposer, a radical inhibitor, a metal inactivating agent, an oxygen scavenger, an amine) or an ultraviolet inhibitor may be added to the cellulose acylate film. The deterioration inhibitor is described in JP-A Nos. 3-199201, 5-1907073, 5-194789, 5-271471 and 6-107854. An amount of the deterioration inhibitor is in the range, based on the solution (dope) to be prepared, of preferably from 0.01 to 1% by mass, more preferably from 0.01 to 0.2% by mass. When the amount thereof is less than 0.01% by mass, the deterioration inhibitor gives little effect. When it is more than 1% by mass, the inhibitor often bleeds out (oozes out) to a surface of the film. Examples of particularly favorable deterioration inhibitors include butylated hydroxytoluene (BHT). The ultraviolet inhibitor is described in JP-A No. 7-11056.

The cellulose acylate film is preferably subjected to a surface treatment. Examples of specific methods of such surface treatments include a corona discharge treatment, a glow discharge treatment, a flame treatment, an acid or alkali treatment and an ultraviolet ray treatment. Further, an undercoat layer is preferably provided as described in JP-A No. 7-333433.

From the standpoint of ensuring planarity of the film, the above treatments are performed by allowing a temperature of the cellulose acylate film to be preferably Tg (glass transition temperature) or less, specifically, 150° C. or less.

From the standpoint of adhesion between the transparent support and the alignment film or the like, it is particularly preferable that the surface treatment of the cellulose acylate film is the acid or alkali treatment, namely, to perform a saponification treatment on the cellulose acylate. The surface treatment thereof is specifically described below taking an alkali saponification treatment as an example. The alkali saponification treatment is preferably performed by a cycle of dipping a film surface in an alkali solution, neutralizing the thus-dipped film surface with an acidic solution, and washing and drying the thus-neutralized film surface. Examples of such alkali solutions include a potassium hydroxide solution and a sodium hydroxide solution. The normality of a hydroxyl ion is in the range of preferably from 0.1 to 3.0 N, more preferably from 0.5 to 2.0 N. The temperature of the alkali solution is in the range of preferably from room temperature to 90° C., more preferably from 40 to 70° C.

Further, a surface energy of the cellulose acylate film is preferably 55 mN/m or more, and more preferably in the range of from 60 to 75 mN/m.

The surface energy can be measured by any one of a contact angle method, a wet heating method and an adsorption method (these methods are described in *Nure no Kiso to Oyo* (*Elemental and Application of Wetting*) published by Realize Co., Ltd, 1989). In a case of the cellulose acylate film used for the present invention, the contact angle method is preferably used. Specifically speaking, two solutions each having a known surface energy are dropped on the cellulose acylate film and, then, an angle between a tangent to such droplet and a film surface at a crossing point between the droplet surface and the film surface, which is an angle facing the droplet, is defined as a contact angle and, subsequently, the surface energy of the film can be calculated from the measured contact angle.

Thickness of the cellulose acylate film is in the range of ordinarily preferably from 5 to 500 μm, preferably from 20 to 250 μm, more preferably from 30 to 180 μm, and particularly preferably from 30 to 110 μm.

Elliptically Polarizing Film

An elliptically polarizing film can be prepared by laminating the retardation film according to the present invention and a polarizing film. By utilizing the retardation film according to the present invention, the elliptically polarizing film which can enlarge a viewing angle of a liquid crystal display device can be provided.

Examples of such polarizing films include an iodine-type polarizing film, a dye-type polarizing film using a dichromatic dye and a polyene polarizing film. The iodine-type polarizing film and the dye-type polarizing film are ordinarily prepared by using a polyvinyl alcohol-type film. A polarizing axis of the polarizing film corresponds to a direction perpendicular to a drawing direction of the film.

The polarizing film is laminated to the retardation film on a side of an optically anisotropic layer thereof. It is preferable that a transparent protective film is formed on a side of the polarizing film opposite to a side on which the retardation film is laminated. The transparent protective film preferably has 80% or more of light transmittance. As for the transparent protective film, ordinarily a cellulose ester film, preferably a triacetyl cellulose film is used. The cellulose ester film is preferably formed by a solvent cast method.

Thickness of the transparent protective film is preferably from 20 to 500 µm, and more preferably from 50 to 200 µm.

Liquid Crystal Display Device

By utilizing the retardation film according to the present invention, a liquid crystal display device having an enlarged viewing angle can be provided. The retardation film for a liquid crystal cell of TN mode (optical compensatory sheet) is described in JP-A No. 6-214116, U.S. Pat. Nos. 5,583,679 and 5,646,703, and GP-A No. 3,911,620A1. Further, the retardation film for a liquid crystal cell of IPS mode or FLC mode is described in JP-A No. 10-5482. Still further, the retardation film for a liquid crystal cell of OCB mode or HAN mode is described in U.S. Pat. No. 5,805,253 and WO96/37804. Yet still further, the retardation film for a liquid crystal cell of STN mode is described in JP-A No. 9-26572. Furthermore, the retardation film for a liquid crystal cell of VA mode is described in Japanese Patent No. 2866372.

According to the present invention, retardation films for liquid crystal cells of various types of modes (optical compensatory sheets) can be prepared with reference to the aforementioned patents documents. The retardation film according to the present invention can be used in liquid crystal display devices of various types of modes such as TN (Twisted Nematic), IPS (In-Plane Switching), FLC (Ferroelectric Liquid Crystal), OCB (Optically comensatory Bend), STN (Super Twisted Nematic), VA (Vertically Aligned) and HAN (Hybrid Aligned Nematic) modes.

The liquid crystal display device comprises a liquid crystal cell, a polarizing element and a retardation film (optically compensatory sheet). The polarizing element ordinarily comprises a polarizing film and a protective film. The polarizing film and the protective film can use those as described in the aforementioned elliptical polarity.

The present invention is described below by referring to Examples, however, the present invention is not limited to these Examples.

EXAMPLE 1

Confirmation of Liquid Crystal Phase by Contact Test(Mixture of (C-1) and (D-3))

(Confirmation of Liquid Crystal Phase Satisfying the Numerical Formula (I))

A liquid crystalline compound (C-1) to be described below was injected into a horizontal alignment cell having a cell gap of 5 µm (KSRP-05/A107M1NSS(ZZ); available from K.K. EHC) at 230° C. and subjected to be homogeneously aligned at 180° C. In the thus-established state, an angle dependence of retardation was measured. When the value of (nx−nz)/(nx−ny) was obtained, it was approximately 1.0 and, accordingly, it was found that the compound (C-1) exhibits a liquid crystal phase satisfying the numerical formula (I).

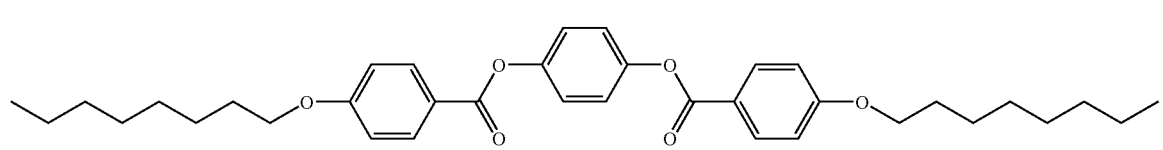

C-1

(Confirmation of Liquid Crystal Phase Satisfying the Numerical Formula (II))

The aforementioned liquid crystalline compound (D-3) was injected into a horizontal alignment cell having a cell gap of 10 µm (KSRP-10/A107M1NSS (ZZ); available from K.K. EHC) at 170° C. and subjected to be homeotropicly aligned t at 140° C. In the thus-established state, an angle dependence of retardation was measured and a conoscope observation was conducted. It was found that (nx−nz)/(nx−ny)=∞ (namely, nx=ny) and, accordingly, the compound (D-3) exhibits a liquid crystal phase satisfying the numerical formula (II).

(Contact Test)

(C-1) and (D-3) were placed on slide glass, covered with cover glass, heated at 200° C. and, then, crystallinity of an overlapping portion of (C-1) and (D-3) at the time of reducing temperature was observed. It was found that a liquid crystal phase was exhibited at any mixing ratio therebetween. Although the temperature at which an isotropic liquid phase is shifted into a liquid crystal phase differs depending on the mixing ratios, the temperature at which a lowest isotropic liquid phase was shifted to the liquid crystal phase was 110° C. (mixing ratio (by mass) was approximately (C-1):(D-3)=1:5.5).

EXAMPLE 2

Confirmation of Liquid Crystal Phase by Contact Test (Mixture of (C-2) and (D-3))

(Confirmation of Liquid Crystal Phase Satisfying the Numerical Formula (I))

A liquid crystalline compound (C-2) (Kelly, S. M. et al., Helv. Chim. Acta, Vol. 71, page 461 (1988)) to be described below was injected into a horizontal alignment cell having a cell gap of 5 µm (KSRP-05/A107M1NSS(ZZ); available from K.K. EHC) at 200° C. and subjected to be homogeneously aligned at 90° C. In the thus-established state, an angle dependence of retardation was measured. When the value of (nx−nz)/(nx−ny) was obtained, it was approximately 1.0 and, accordingly, it was found that the compound (C-2) exhibits a liquid crystal phase satisfying the numerical formula (I).

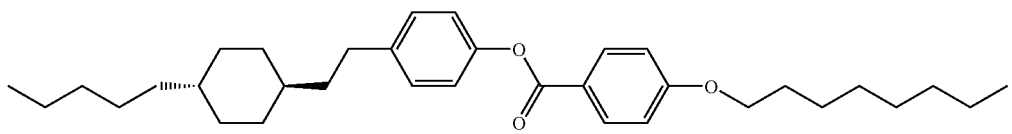

C-2

(Contact Test)

(C-2) and (D-3) were placed on slide glass, covered with cover glass, heated at 200° C. and, then, crystallinity of an overlapping portion of (C-2) and (D-3) at the time of reducing temperature was observed. It was found that a liquid crystal phase was exhibited at any mixing ratio therebetween. Although the temperature at which an isotropic liquid phase is shifted into a liquid crystal phase differs depending on the mixing ratios, the temperature at which a lowest isotropic liquid phase was shifted to the liquid crystal phase was 95° C. (mixing ratio (by mass) was approximately (C-2):(D-3)=1:5).

EXAMPLE 3

Confirmation of Liquid Crystal Phase by Contact Test (Mixture of (m-4) and (D-3))

(Confirmation of Liquid Crystal Phase Satisfying the Numerical Formula (I))

The aforementioned liquid crystalline compound (m-4) was injected into a horizontal alignment cell having a cell gap of 5 μm (KSRP-05/A107M1NSS(ZZ); available from K.K. EHC) at 200° C. and subjected to be homogeneously aligned at 130° C. In the thus-established state, an angle dependence of retardation was measured. When the value of (nx−nz)/(nx−ny) was obtained, it was approximately 1.0 and, accordingly, it was found that the compound (m-4) exhibits a liquid crystal phase satisfying the numerical formula (I).

(Contact Test)

(m-4) and (D-3) were placed on slide glass, covered with cover glass, heated at 200° C. and, then, crystallinity of an overlapping portion of (m-4) and (D-3) at the time of reducing temperature was observed. It was found that a liquid crystal phase was exhibited at any mixing ratio therebetween. Although the temperature at which an isotropic liquid phase is shifted into a liquid crystal phase differs depending on the mixing ratios, the temperature at which a lowest isotropic liquid phase was shifted to the liquid crystal phase was 105° C. (mixing ratio (by mass) was approximately (m-4):(D-3)=1:4).

EXAMPLE 4

Confirmation of Liquid Crystal Phase by Contact Test (Mixture of (m-22) and (D-3))

(Confirmation of Liquid Crystal Phase Satisfying the Numerical Formula (I))

The aforementioned liquid crystalline compound (m-22) was injected into a horizontal alignment cell having a cell gap of 5 μm (KSRP-05/A107M1NSS(ZZ); available from K.K. EHC) at 200° C. and subjected to be homogeneously aligned at 130° C. In the thus-established state, an angle dependence of retardation was measured. When the value of (nx−nz)/(nx−ny) was obtained, it was from 1.0 to less than 1.1 and, accordingly, it was found that the compound (m-22) exhibits a liquid crystal phase satisfying the numerical formula (I).

(Contact Test)

(m-22) and (D-3) were placed on slide glass, covered with cover glass, heated at 200° C. and, then, crystallinity of an overlapping portion of (m-22) and (D-3) at the time of reducing temperature was observed. It was found that a liquid crystal phase was exhibited at any mixing ratio therebetween. Although the temperature at which an isotropic liquid phase is shifted into a liquid crystal phase differs depending on the mixing ratios, the temperature at which a lowest isotropic liquid phase was shifted to the liquid crystal phase was 110° C. (mixing ratio (by mass) was approximately (m-22):(D-3)=1:3).

EXAMPLE 5

Confirmation Of Liquid Crystal Phase by Contact Test (Mixture of (m-22) and (Dmix-1))

(Confirmation of Liquid Crystal Phase Satisfying the Numerical Formula (II))

0.9 g of (D-3) and 0.1 g of a discotic liquid crystalline compound (TP-1) to be described below were dissolved in $CH_2Cl_2$ and, then, the solvent in the resultant solution was evaporated, to thereby obtain (Dmix-1). The thus-obtained (Dmix-1) was injected into a horizontal alignment cell having a cell gap of 10 μm (KSRP-10/A107M1NSS(ZZ); available from K.K. EHC) at 170° C. and subjected to be homeotropicly aligned at 120° C. In the thus-established state, an angle dependence of retardation was measured and a conoscope observation was conducted. It was found that (nx−nz)/(nx−ny)=∞ (namely, nx=ny) and, accordingly, the compound (Dmix-1) exhibits a liquid crystal phase satisfying the numerical formula (II).

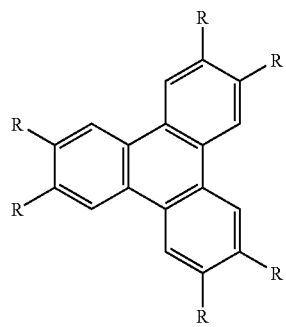

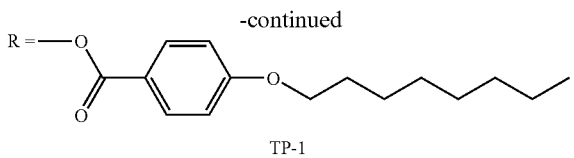

TP-1

(Contact Test)

(m-22) and (Dmix-1) were placed on slide glass, covered with cover glass, heated at 200° C. and, then, crystallinity of an overlapping portion of (m-22) and (Dmix-1) at the time of reducing temperature was observed. It was found that a liquid crystal phase was exhibited at any mixing ratio therebetween. Although the temperature at which an isotropic liquid phase is shifted into a liquid crystal phase differs depending on the mixing ratios, the temperature at which a lowest isotropic liquid phase was shifted to the liquid crystal phase was 102° C. (mixing ratio (by mass) was approximately (m-22):(Dmix-1)=1:3).

EXAMPLE 6

Preparation of Retardation Film and Confirmation of Biaxiality (Mixture System of (m-22) and (D-3))

0.3 g of (D-3) and 0.1 g of (m-22) were dissolved in $CH_2Cl_2$ and, then, the solvent was evaporated, to thereby obtain (BAmix-1). It was clear from an observation under a polarizing microscope that (BAmix-1) exhibits a nematic phase at 110° C. or less when it is cooled from 150° C.

Next, the thus-obtained (BAmix-1) was injected into a horizontal alignment cell having a cell gap of 5 μm (KSRP-05/A107M1NSS (ZZ); available from K.K. EHC) at 200° C. and, then, when it was cooled down to 107° C., a nematic phase transition occurred to allow it to be in a homeotropic alignment and in a dark field. Successively, when it was cooled to 100° C., a liquid crystal transition occurred and it was shifted to a biaxial nematic phase. After it was kept at 100° C. for 3 minutes, an angle dependence of retardation was measured. When the value of (nx−nz)/(nx−ny) was obtained, it was 4.0.

After (BAmix-1) is subjected to be aligned at 100° C., it was rapidly cooled down to room temperature, to thereby obtain a biaxial retardation film.

EXAMPLE 7

Preparation of Retardation Film and Confirmation of Biaxiality (Mixture System of (m-22) and (Dmix-1))

0.3 g of (Dmix-1) and 0.1 g of (m-22) were dissolved in $CH_2Cl_2$ and, then, the solvent was evaporated, to thereby obtain (BAmix-2). It was clear from an observation under a polarizing microscope that (BAmix-2) exhibits a nematic phase at 102° C. or less when it is cooled from 150° C.

Next, the thus-obtained (BAmix-2) was injected into a horizontal alignment cell having a cell gap of 5 μm (KSRP-05/A107M1NSS (ZZ); available from K.K. EHC) at 200° C. and, then, when it was cooled down to 102° C., a nematic phase transition occurred to allow it to be in a homeotropic alignment and in a dark field. Successively, when it was cooled to 100° C., a liquid crystal transition occurred and it was shifted to a biaxial nematic phase. After it was kept at 100° C. for 3 minutes, an angle dependence of retardation was measured. When the value of (nx−nz)/(nx−ny) was obtained, it was 1.5.

After (BAmix-2) was subjected to be aligned at 100° C., it was rapidly cooled down to room temperature, to thereby obtain a biaxial retardation film.

EXAMPLE 8

Preparation of Retardation Film (Formation of Alignment Film)

Modified polyvinyl alcohol to be described below and glutaraldehyde (5% by mass on the basis of modified vinyl alcohol) were dissolved in a mixed solvent of methanol/water (percentage by volume=20/80), to thereby prepare a 5% by mass solution.

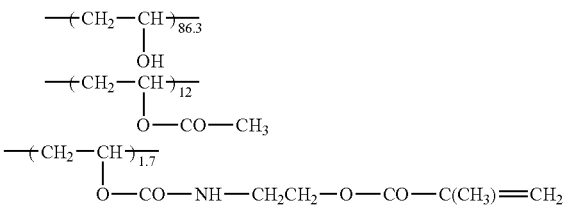

The thus-prepared solution was applied on a glass substrate, dried at 100° C. with a hot wind air for 120 seconds and, then, subjected to a rubbing treatment, to thereby form an alignment film. Thickness of the thus-formed alignment film was 0.5 μm.

(Formation of Optically Anisotropic Layer)

On the thus-prepared alignment film which has been subjected to the rubbing treatment, a coating solution for optically anisotropic layer having a composition to be described below was applied by using a spin coater.

| (Coating solution for optically anisotropic layer) | |
| --- | --- |
| Aforementioned liquid crystalline compound D-8 | 69.7 parts by mass |
| Aforementioned liquid crystalline compound TO-3 | 30.3 parts by mass |
| Air interface alignment-controlling agent V-(1) | 0.2 part by mass |
| IRGACURE 907 (available from Nagase & Co.) | 1.0 part by mass |
| Chloroform | 700 parts by mass |

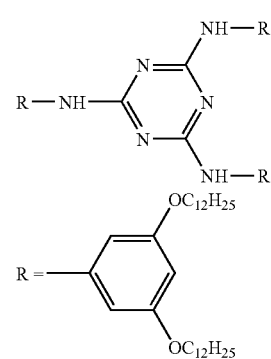

V-(1)

The glass substrate on which the aforementioned optically anisotropic layer had been applied was placed in a thermostat set at 130° C., heated to 120° C., cooled to 95° C. and held at 95° C. for 2 minutes. Next, the resultant glass substrate was placed in a thermostat set at 80° C. having an oxygen concentration of 2% and, after 5 minutes, irradiated with an ultraviolet ray of 600 mJ, to thereby fix an alignment state of the optically anisotropic layer. The resultant glass substrate was cooled down to room temperature to prepare a retardation film. Thickness of the optically anisotropic layer was 1.0 μm. A slow axis was parallel to a rubbing direction.

When an angle dependence of retardation of the thus-obtained retardation film was measured, it was found that an nx direction was parallel to a glass substrate face while an nz direction was perpendicular to the glass substrate face. Further, when the value of (nx−nz)/(nx−ny) was obtained, it was 4.0.

EXAMPLE 9

Preparation of Retardation Film (Formation of Optically Anisotropic Layer)

On the alignment film which has been prepared in Example 8 and been subjected to the rubbing treatment, a coating solution for optically anisotropic layer having a composition described below was applied by using a spin coater.

| (Coating solution for optically anisotropic layer) | |
| --- | --- |
| Aforementioned liquid crystalline compound D-8 | 68.8 parts by mass |

| -continued | |
| --- | --- |
| (Coating solution for optically anisotropic layer) | |
| Aforementioned liquid crystalline compound TO-3 | 31.2 parts by mass |
| Air interface alignment-controlling agent V-(1) | 0.2 part by mass |
| IRGACURE 907 (available from Nagase & Co.) | 1.0 part by mass |
| Chloroform | 700 parts by mass |

The glass substrate on which the aforementioned optically anisotropic layer had been applied was placed in a thermostat set at 130° C., heated to 120° C., cooled to 95° C. and held at 95° C. for 2 minutes. Next, the resultant glass substrate was placed in a thermostat set at 70° C. having an oxygen concentration of 2% and, after 5 minutes, irradiated with an ultraviolet ray of 600 mJ, to thereby fix an alignment state of the optically anisotropic layer. The resultant glass substrate was cooled down to room temperature to prepare a retardation film. Thickness of the optically anisotropic layer was 1.0 μm. A phase-retarding axis was parallel to a rubbing direction.

When an angle dependence of retardation of the thus-obtained retardation film was measured, it was found that an nx direction was parallel to a glass substrate face while an nz direction was perpendicular to the glass substrate face. Further, when the value of (nx−nz)/(nx−ny) was obtained, it was 2.0.

EXAMPLE 10

Synthesis of D-9

D-9 was synthesized in accordance with the following scheme:

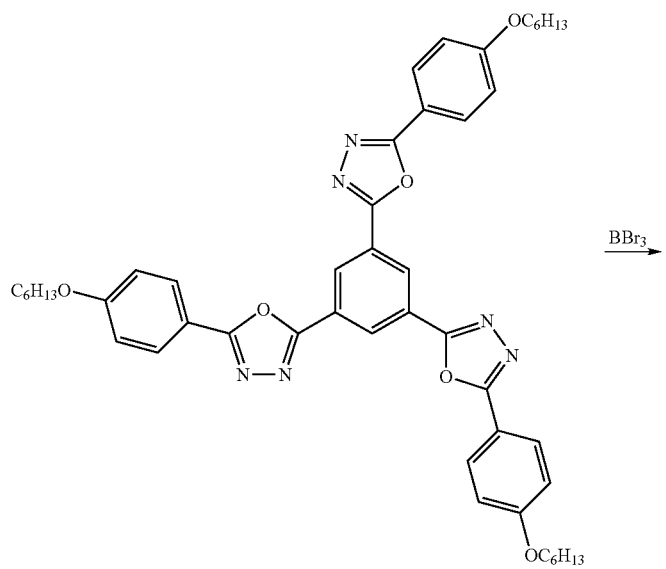

D-3

-continued

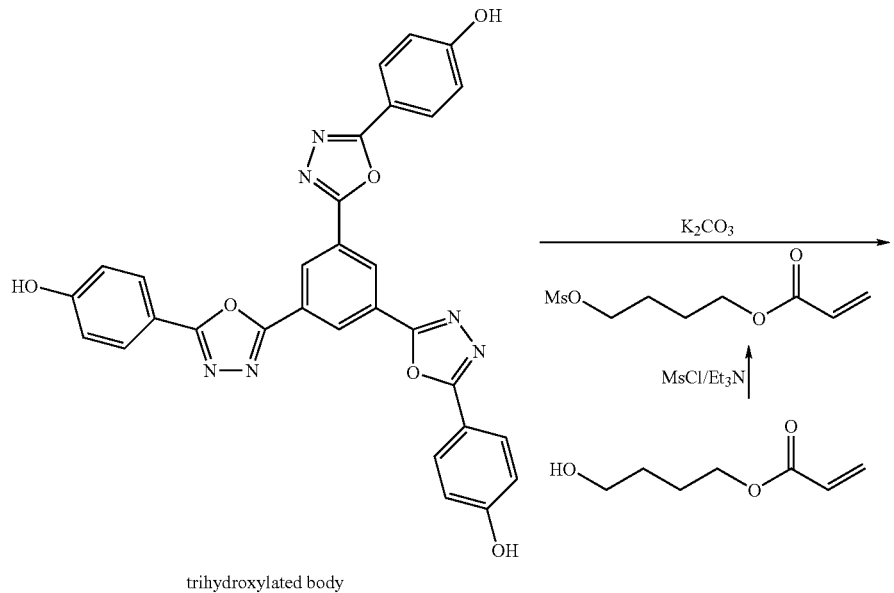

trihydroxylated body

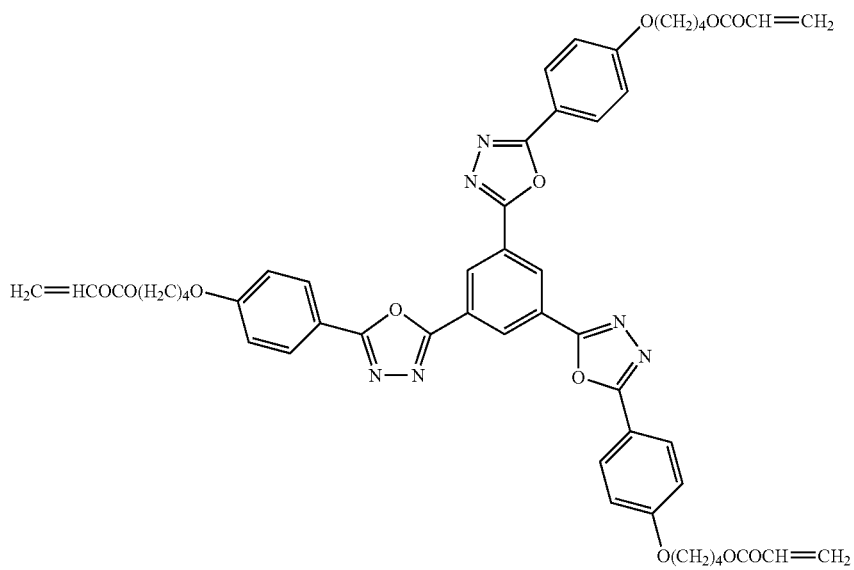

D-9

5.0 g of (D-3) which had been synthesized in accordance with a method described in a document (Kim, Bong, Gi et al., *Molecular Crystals and Liquid Crystals*, Vol. 370, page 391, (2001)) was dissolved in 100 ml of $CH_2Cl_2$ and, then, added with 75 ml of boron tribromide (1.0M $CH_2Cl_2$ solution). The resultant mixture was stirred for 12 hours at 40° C. to obtain a reaction solution. The thus-obtained reaction solution was added with water to precipitate a crystal. The thus-precipitated crystal was collected by filtration, dried and, as a result, 3.0 g of a trihydroxylated body.

Firstly, 6.5 g of 4-hydroxybutylacrylate and 8.0 g of triethyl amine were dissolved in 100 ml of ethyl acetate to prepare a first solution. Next, another solution which had been prepared by dissolving 4.2 g of methane sulfonylchloride in 50 ml of ethyl acetate was added to the first solution in a dropping manner at a reaction temperature of 30° C. or less. The resultant mixture was stirred for 0.5 hour and, then, added with 100 ml of water to rinse an ethyl acetate layer and, then, subjected to a separation treatment. After the result ant ethyl acetate layer was subjected to a distillation treatment, added with 0.5 g of the aforementioned trihydroxylated body, 0.8 g of potassium carbonate and dimethyl formamide and, then, stirred for 5 hours at 100° C. The resultant reaction liquid was added with water and, then, subjected to an extraction treatment by using CH₂Cl₂ to obtain an organic layer. The thus-obtained organic layer was concentrated and, then, purified by using a column chromatography and, as a resulT0.7 g of a crystal of (D-9).

¹H-NMR (solvent: CDCl₃, standard: tetramethylsilane) δ(ppm) 1.70-1.90 (6H, m) 1.90-2.00 (6H, m) 3.95-4.30 (12H, m) 5.80 (3H, d) 6.14 (3H, dd) 6.43 (3H, d) 7.08 (3H, d) 8.13 (3H, d) 9.02 (3H, s)

When a phase transition temperature of the thus-obtained D-9 was examined by a texture observation by a polarizing microscope, a transition of a crystal phase to a columnar phase occurred at around 131° C., while elevating a temperature. A transition of the columnar phase to a discotic nematic phase occurred at around 134° C. When the temperature went over 138° C., a transition of the discotic nematic phase to an isotropic liquid phase occurred. In other words, it was found that D-9 exhibits a liquid crystal phase in the range of from 131° C. to 138° C. and, particularly, the discotic nematic phase in the range of from 134° C. to 138° C.

D-9 (containing 0.1% by weight of hydroquinone monomethyl ether) injected into a horizontal alignment cell having a cell gap of 10 μm (KSRP-10/A107M1NSS (ZZ); available from K.K. EHC) at 150° C. and subjected to be homeotropicly aligned at 130° C. In the thus-established state, an angle dependence of retardation was measured and a conoscope observation was conducted. It was found that (nx−nz)/(nx−ny)=∞ (namely, nx=ny) and, accordingly, D-9 exhibits a liquid crystal phase satisfying the numerical formula (II).

EXAMPLE 11

(Synthesis of D-8)

D-8 was synthesized in accordance with the following scheme:

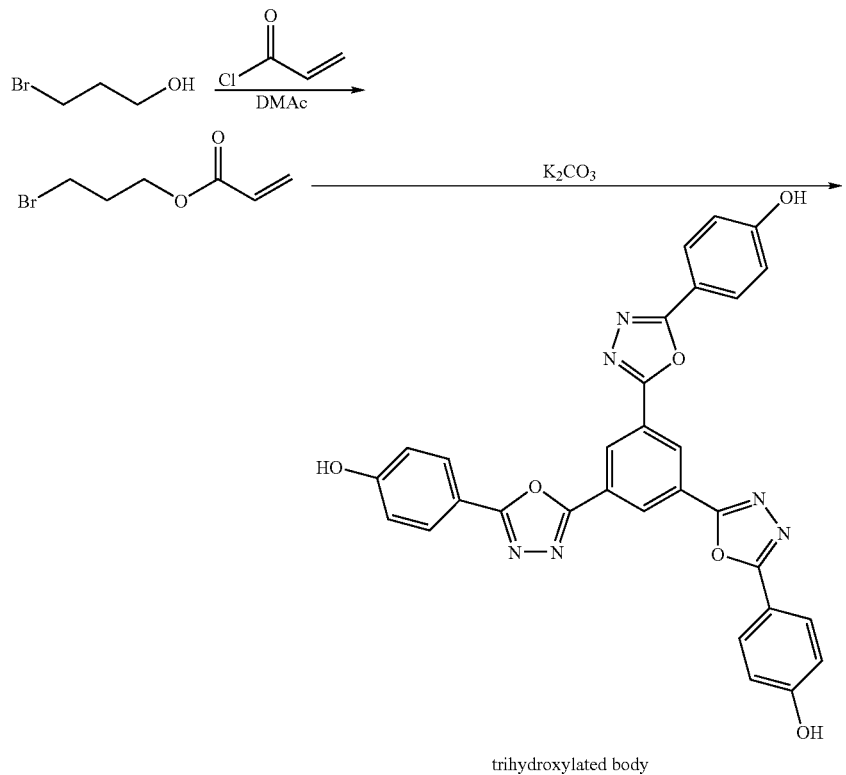

trihydroxylated body

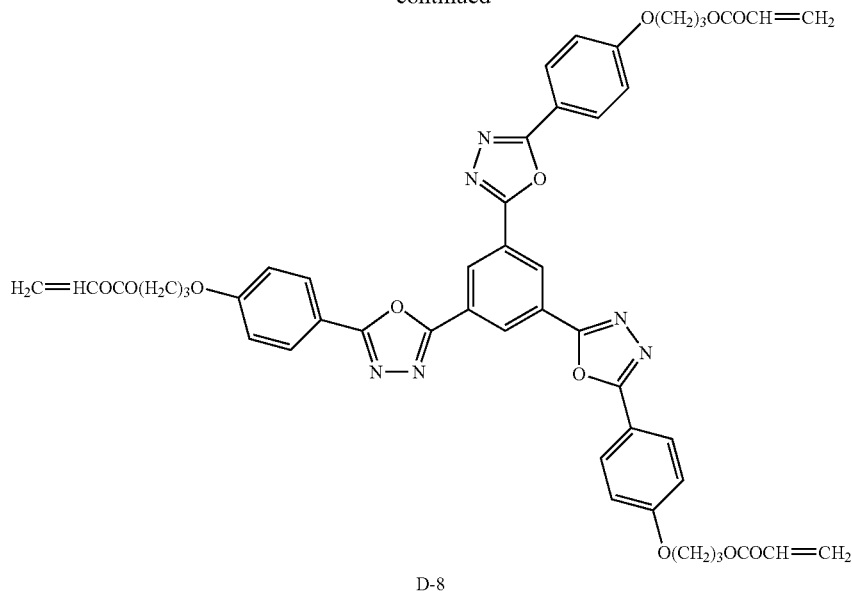

D-8

5 g of 3-bromo-1-propanol was dissolved in 20 ml of dimethyl acetamide and, then, added with 3.8 ml of acryloyl chloride in a dropping manner at a reaction temperature of 40° C. or less. The resultant mixture was stirred for 1 hour and, then, added with 200 ml of water and, then, subjected to an extraction treatment by using ethyl acetate/hexane. After a liquid separation was performed, the resultant organic layer was subjected to a distillation treatment and, then, added with 0.5 g of the trihydroxylated body as described in Example 10, 2.0 g of potassium carbonate and dimethyl formamide and, then, stirred for 10 hours at 100° C. The resultant reaction liquid was added with water and, then, subjected to an extraction treatment by using $CH_2Cl_2$. The resultant organic layer was concentrated and, then, purified by using a column chromatography and, as a resulT0.8 g of a crystal of D-8.

$^1$H-NMR (solvent: $CDCl_3$, standard: tetramethylsilane) δ(ppm) 2.15-2.30 (6H, m) 4.18 (6H, t) 4.43 (6H, t) 5.86 (3H, d) 6.16 (3H, dd) 6.45 (3H, d) 7.08 (6H, d) 8.16 (6H, d) 9.02 (3H, s)

When a phase transition temperature of the thus-obtained D-8 was examined by a texture observation by a polarizing microscope, a transition of a crystal phase to a discotic nematic phase occurred at around 125° C., while elevating a temperature. When the temperature went over 149° C., a transition of the discotic nematic phase to an isotropic liquid phase occurred. In other words, it was found that D-8 exhibits a discotic nematic phase in the range of from 125° C. to 149° C.

EXAMPLE 12

(Synthesis of D-7)

D-7 was synthesized in accordance with the following scheme:

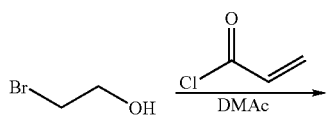

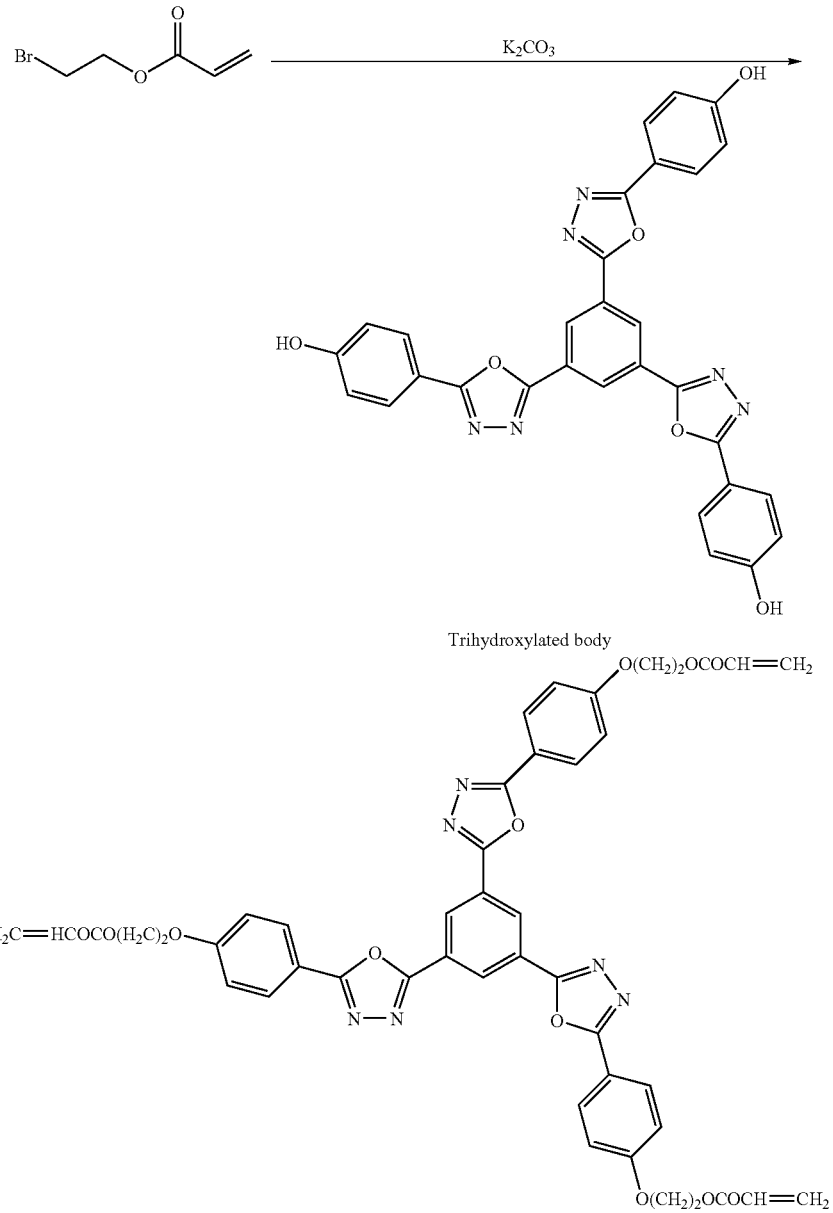

5 g of 2-bromoethanol was dissolved in 20 ml of dimethyl acetamide and, then, added with 3.9 ml of acryloyl chloride in a dropping manner at a reaction temperature of 40° C. or less. The resultant mixture was stirred for 1 hour and, then, added with 200 ml of water and, then, subjected to an extraction treatment by using ethyl acetate/hexane. After a liquid separation was performed, the resultant organic layer was subjected to a distillation treatment and, then, added with 0.5 g of the trihydroxylated body as described in Example 10, 2.0 g of potassium carbonate and dimethyl formamide and, then, stirred for 10 hours at 100° C. The resultant reaction liquid was added with water and, then, subjected to an extraction treatment by using $CH_2Cl_2$. The resultant extracted organic layer was concentrated and, then, purified by using a column chromatography and, as a resulTO.7 g of a crystal of D-7.

$^1$H-NMR (solvent: $CDCl_3$, standard: tetramethylsilane) δ(ppm) 4.34 (6H, t) 4.60 (6H, t) 5.88 (3H, d) 6.18 (3H, dd) 6.50 (3H, d) 7.12 (6H, d) 8.18 (6H, d) 9.02 (3H, s)

A phase transition temperature of the thus-obtained D-7 was examined by a texture observation by means of a polarizing microscope. While elevating a temperature, a transition of a crystal phase to an isotropic liquid phase occurred at around 165° C. When the temperature was gradually reduced from 170° C., a transition of the isotropic liquid phase to a discotic nematic phase occurred at around 155° C. When the temperature was further reduced, it was shifted again to the crystal phase. In other words, it was found that D-7 exhibits a discotic nematic phase in the range of from 155° C. to 130° C. at the time of reduction of the temperature.

EXAMPLE 13

(Synthesis of m-4)

m-4 was synthesized in accordance with the following scheme:

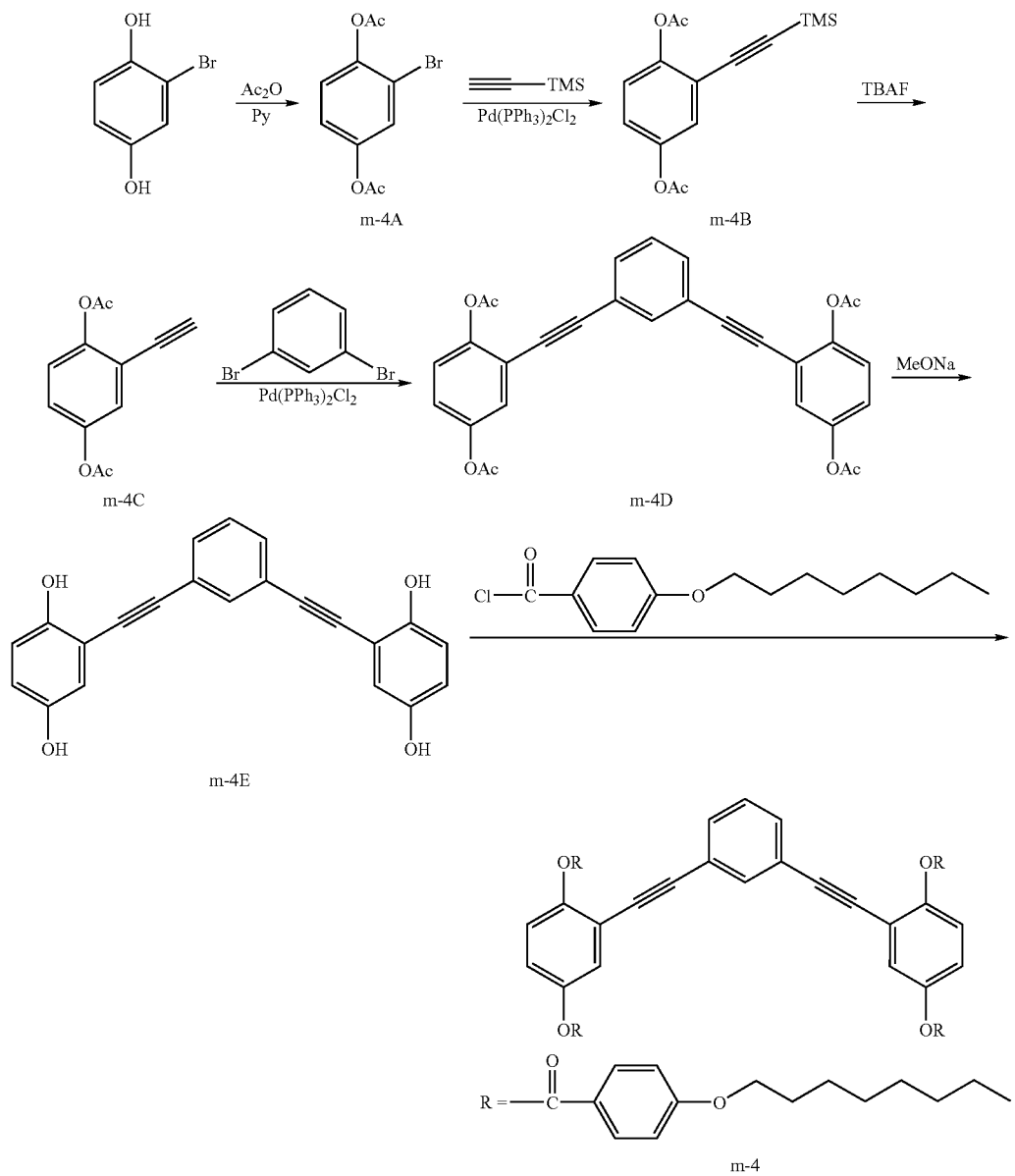

(Synthesis of m-4A)

25.0 g of bromohydroquinone was dissolved in 70 ml of pyridine (Py) and, then, added with 37 ml of acetic acid anhydrous ($Ac_2O$) at a reaction temperature of 50° C. or less in a dropping manner. The resultant reaction liquid was stirred for 3 hours and, then, added with water and, thereafter, subjected to an extraction treatment by using ethyl acetate to obtain an organic layer. The thus-obtained organic layer was rinsed with a saturated sodium bicarbonate solution, diluted hydrochloric acid, water and saturated brine in the stated order. Thereafter, the solvent was removed from the thus-rinsed organic layer by distillation under reduced pressure. The residual was allowed to be crystallized by using hexane, to thereby obtain 32.2 g of a crystal of m-4A.

(Synthesis of m-4B)

32.2 g of m-4A, 17.4 g of trimethylsilyl (TMS) acetylene, 0.5 g of triphenylphosphine, 0.25 g of bis(triphenylphosphine)palladium(II) dichloride and 80 mg of copper(I) iodide were dissolved in 200 ml of triethyl amine and, then, refluxed for 10 hours under a nitrogen atmosphere. Then, the resultant solution was cooled to precipitate triethyl amine hydrochloric acid salt. Thereafter, the thus-precipitated triethyl amine hydrochloric acid salt was collected by filtration and, then, an organic layer was subjected to a distillation treatment under reduced pressure. The resultant residual was purified by using a column chromatography, to thereby obtain 32.0 g of a crystal of m-4B.

(Synthesis of m-4C)

32.0 g of m-4B was dissolved in 200 ml of tetrahydrofuran and, then, added with 120 ml of a tetrahydrofuran solution (1.0 M solution) of tetrabutylammonium fluoride (TBAF) and, thereafter, stirred for 30 minutes at room temperature. The resultant reaction solution was added with water and, then, subjected to an extraction treatment by using ethyl acetate. The resultant extracted article was rinsed with saturated brine. The resultant organic layer was concentrated under reduced pressure and, then, purified by using a column chromatography, to thereby obtain 20.5 g of a crystal of m-4C.

(m-4D)

3.0 g of m-4C, 1.38 g of 1,3-dibromobenzene, 58 mg of triphenylphosphine, 29 mg of bis(triphenylphosphine)palladium(II) dichloride and 10 mg of copper(I) iodide were dissolved in 23 ml of triethyl amine and, then, refluxed for 10 hours under a nitrogen atmosphere. Then, the resultant solution was cooled and, then, added with 100 ml of methanol. The resultant precipitated crystal was collected by filtration and, then, purified by using a column chromatography, to thereby obtain 2.1 g of a crystal of m-4D.

(Synthesis of m-4E)

0.6 g of m-4D was dissolved in 30 ml of methanol and, then, added with 2 ml of sodium methoxide (28% methanol solution) under a nitrogen-bubbling atmosphere. The resultant solution was stirred for one hour at room temperature and, then, added with diluted hydrochloric acid and, thereafter, subjected to an extraction treatment by using ethyl acetate to obtain an organic layer. The thus-obtained organic layer was subjected to a distillation treatment under reduced pressure, to thereby obtain 0.4 g of a crystal of m-4E.

(Synthesis of m-4)

5.0 g of 4-octyloxybenzoic acid chloride which was obtained by an ordinary method, 0.4 g of m-4E were dissolved in 20 ml of tetrahydrofuran and, then, added with 3.0 ml of diisopropylethylamine and 0.1 g of dimethylaminopyridine and, thereafter, stirred for 6 hours at room temperature. The resultant reaction liquid was added with water and, then, subjected to an extraction treatment by using $CH_2Cl_2$. The thus-extracted article was concentrated under reduced pressure and, then, purified by using a column chromatography to obtain 1.1 g of a crystal of m-4. An NMR spectrum of the thus-obtained m-4 was as follows:

$^1$H-NMR (solvent: $CDCl_3$, standard: tetramethylsilane) δ(ppm) 0.85-0.95 (12H, m) 1.20-1.60 (40H, m) 1.70-1.90 (8H, m) 3.95-4.10 (8H, m) 6.90-7.00 (8H, m) 7.05-7.15 (4H, m) 7.27 (2H) 7.43 (2H, d) 7.46 (2H, d) 8.10-8.20 (8H, m)

Further, when a phase transition temperature of the thus-obtained m-4 was examined by a texture observation by a polarizing microscope, a transition of a crystal phase to a nematic liquid crystal phase occurred at around 105° C., while elevating a temperature. When the temperature was over 156° C., a transition of the nematic liquid crystal phase to an isotropic liquid phase occurred. In other words, it was found that m-4 exhibits a nematic liquid crystal phase in the range of from 105° C. to 156° C.

EXAMPLE 14

(Synthesis of m-22)

m-22 was synthesized in accordance with the following scheme:

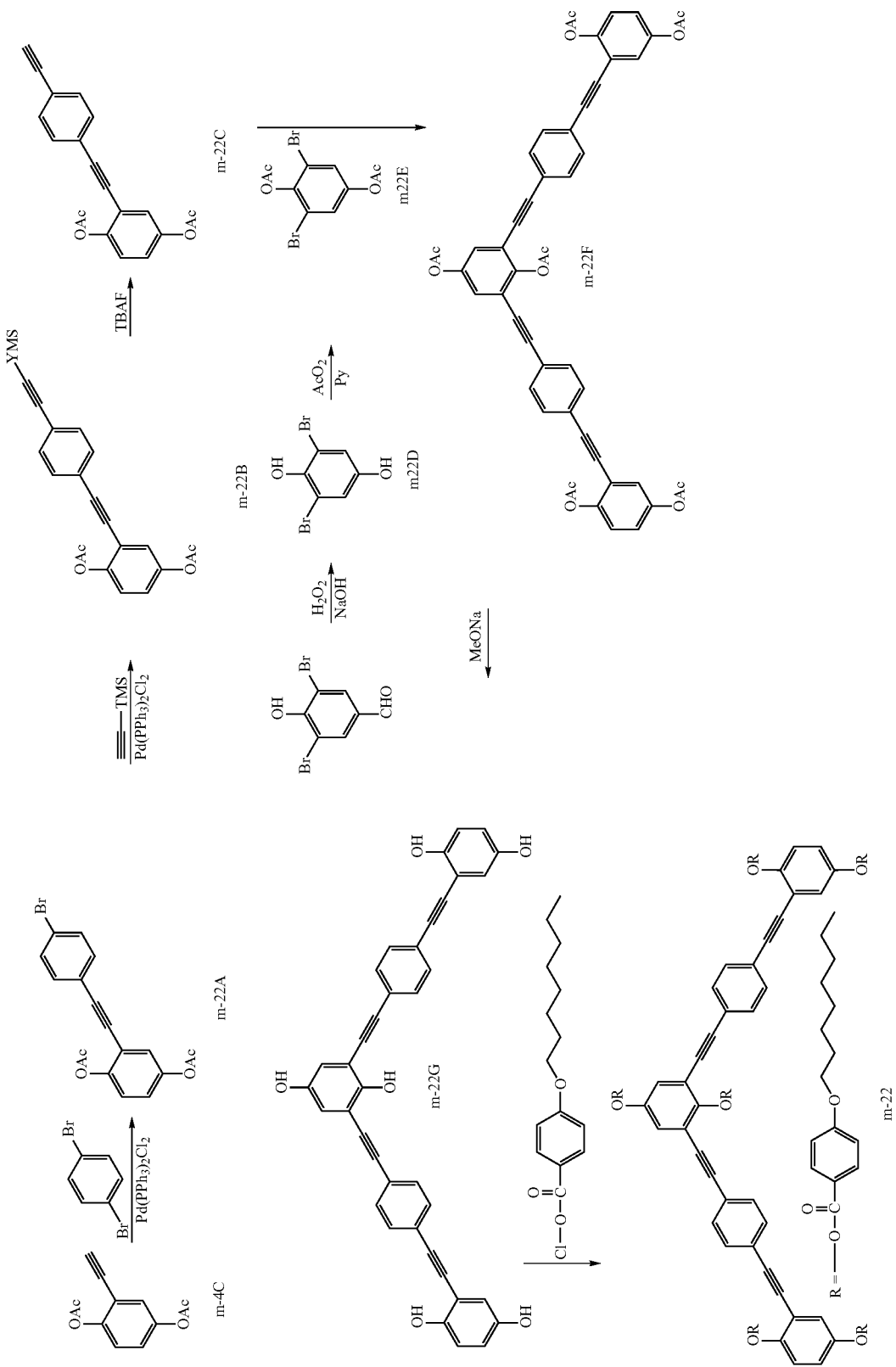

(Synthesis of m-22A)

3.0 g of m-4C obtained in accordance with Example 13, 10 g of 1,4-dibromobenzene, 58 mg of triphenylphosphine, 29 g of bis(triphenylphosphine)palladium(II) dichloride and 10 mg of copper(I) iodide were dissolved in 50 ml of triethyl amine and, then, refluxed for 10 hours under a nitrogen atmosphere. Then, the resultant solution was cooled. Thereafter, the reaction solution was added with water and, then, subjected to an extraction treatment by using ethyl acetate. The resultant extracted article was rinsed with saturated brine. The resultant organic layer was concentrated under reduced pressure and, then, purified by using a column chromatography, to thereby obtain 2.9 g of a crystal of m-22A.

(Synthesis of m-22B)

2.1 g of m-22A, 0.83 g of trimethylsilylacetylene, 24 mg of triphenylphosphine, 12 mg of bis(triphenylphosphine)palladium(II) dichloride and 4 mg of copper(I) iodide were dissolved in 20 ml of triethyl amine and, then, refluxed for 10 hours under a nitrogen atmosphere. Then, the resultant solution was cooled. Thereafter, the reaction liquid was added with water and, then, subjected to an extraction treatment by using ethyl acetate. The resultant extracted article was rinsed with saturated brine. The resultant organic layer was concentrated under reduced pressure and, then, purified by using a column chromatography, to thereby obtain 1.5 g of a crystal of m-22B.

(Synthesis of m-22C)

1.5 g of m-22B was dissolved in 200 ml of tetrahydrofuran and, then, added with 5 ml of a tetrahydrofuran solution (1.0 M solution) of tetrabutylammonium fluoride and, thereafter, stirred for 30 minutes at room temperature. The resultant reaction solution was added with water and, then, subjected to an extraction treatment by using ethyl acetate. The resultant extracted article was rinsed with saturated brine. The resultant organic layer was concentrated under reduced pressure and, then, purified by using a column chromatography, to thereby obtain 0.9 g of a crystal of m-22C.

(Synthesis of m-22D)

15.2 g of 3,5-dibromo-4-hydroxybenzaldehide was added with 200 ml of water and 54.3 ml of a 1 M sodium hydroxide solution and, then, heated at 50° C. and, thereafter, added with a solution in which 6.2 ml of hydrogen peroxide water (31%) was diluted with 20 ml of water in a dropping manner. The resultant mixture was allowed to react for 5 hours at 50° C. and, thereafter, added with hydrochloric acid to precipitate a crystal which was, then, collected by filtration. The thus-collected crystal was dried and, then, added with 100 ml of toluene, 7.0 g of octyl cyanoacetate, 1 ml of acetic acid and 0.5 g of ammonium chloride and, then, refluxed for 3 hours while removing water. The resultant reaction solution was added with water and, then, subjected to an extraction treatment by using ethyl acetate. The resultant extracted article was rinsed with saturated brine. The resultant organic layer was concentrated under reduced pressure. The resultant obtained crystal was added with hexane and, then, rinsed for 30 minutes while heating. In a heating state, filtration was conducted, to thereby obtain 7.4 g of a crystal of m-22D.

(Synthesis of m-22E)

7.35 g of m-22D was dissolved in 20 ml of pyridine and, then, added with 7.8 ml of acetic acid anhydrous in a dropping manner at a reaction temperature of 50° C. or less and, thereafter, stirred for 3 hours at 50° C. The resultant reaction liquid was added with water and, then, subjected to an extraction treatment by using ethyl acetate. The resultant extracted organic layer was rinsed with a saturated sodium bicarbonate, solution, water and saturated brine in the stated order. Thereafter, the solvent was removed therefrom by distillation under reduced pressure. The residual was allowed to be crystallized by using hexane, to thereby obtain 9.3 g of a crystal of m-22E.

(Synthesis of m-22F)

0.7 g of m-22C, 0.37 g of m-22E, 10 mg of triphenylphosphine, 5 mg of bis(triphenylphosphine)palladium(II) dichloride and 2 mg of copper(I) iodide were dissolved in 20 ml of triethyl amine and, then, refluxed for 10 hours under a nitrogen atmosphere. Then, the resultant solution was cooled. Thereafter, the resultant reaction liquid was added with water and, then, subjected to an extraction treatment by using ethyl acetate. The resultant extracted article was rinsed with saturated brine. The resultant organic layer was concentrated under reduced pressure and, then, purified by using a column chromatography, to thereby obtain 0.15 g of a crystal of m-22F.

(Synthesis of m-22G)

0.15 g of m-22F was dissolved in a mixed solution of 20 ml of tetrahydrofuran and 5 ml of methanol and, then, added with 0.4 ml of sodium methoxide (28% methanol solution) under a nitrogen-bubbling atmosphere. The resultant solution was stirred for one hour at room temperature and, then, added with diluted hydrochloric acid and, thereafter, subjected to an extraction treatment by using ethyl acetate to obtain an organic layer. The thus-obtained organic layer was subjected to a distillation treatment under reduced pressure, to thereby obtain 0.10 g of a crystal of m-22G.

(Synthesis of m-22)

0.05 g of m-22G and 0.4 g of 4-octyloxybenzoic acid chloride were dissolved in 10 ml of tetrahydrofuran and, then, added with 0.2 g of diisopropylethylamine and 0.01 g of 4-dimethylaminopyridine and, thereafter, stirred for 12 hours at room temperature. The resultant reaction liquid was added with water and, then, subjected to an extraction treatment by using ethyl acetate. The thus-extracted article was concentrated under reduced pressure and, then, purified by using a column chromatography to obtain 0.2 g of a crystal of m-22. An NMR spectrum of the thus-obtained m-22 was as follows:

$^1$H-NMR (solvent: $CDCl_3$, standard: tetramethylsilane) δ(ppm) 0.85-0.95 (18H, m) 1.20-1.60 (60H, m) 1.70-1.90 (12H, m) 3.95-4.10 (12H, m) 6.90-7.00 (12H, m) 7.00-7.50 (16H, m) 8.10-8.25 (12H, m)

When a phase transition temperature of the thus-obtained m-22 was examined by a texture observation by a polarizing microscope, a transition of a crystal phase to a nematic liquid crystal phase occurred at around 110° C., while elevating a temperature. When the temperature was over 156° C., a transition of the nematic liquid crystal phase to an isotropic liquid phase occurred. In other words, it was found that m-22 exhibits a nematic liquid crystal phase in the range of from 110° C. to 156° C.

EXAMPLE 15

(Synthesis of m-23)

m-23 was synthesized in accordance with the following scheme:

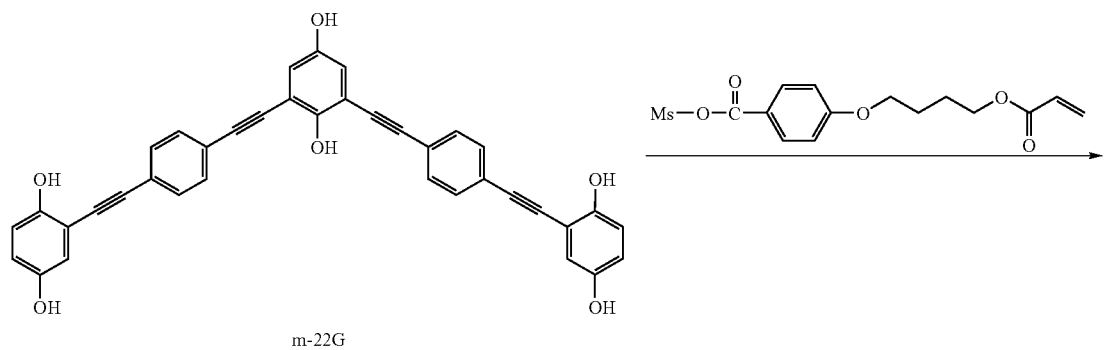

m-22G

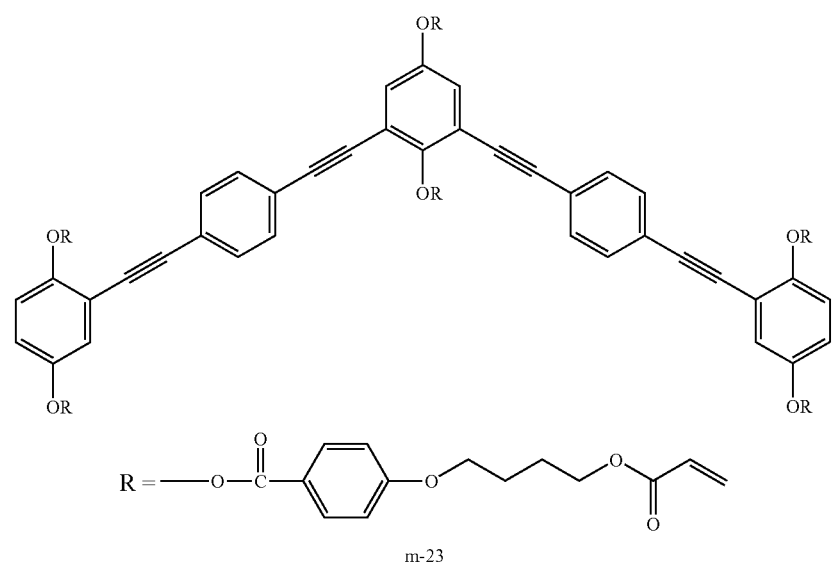

m-23

To a solution in which 0.43 g of methane sulfonyl chloride was dissolved in 10 ml of tetrahydrofuran and, then, cooled, 1.0 g of 4-(4-acryloyloxybtyloxy)benzoic acid, and 10 ml of a tetrahydrofuran solution of 0.51 g of diisopropylethylamine were added in a dropping manner. The resultant mixture was stirred for one hour a T0° C. and, then, added with 0.51 g of diisopropylethylamine and 0.02 g of 4-dimethylaminopyridine and, thereafter, added with 10 ml of tetrahydrofuran of 0.05 g of m-22 G obtained in accordance with Example 14. The resultant mixture was stirred for 12 hours at room temperature. The resultant reaction solution was added with water and, then, subjected to an extraction treatment by using ethyl acetate. The resultant extracted article was concentrated under reduced pressure and, then, purified by using a column chromatography, to thereby obtain 0.15 g of a crystal of m-23. An NMR spectrum of the thus-obtained m-23 was as follows:

$^1$H-NMR (solvent: CDCl$_3$, standard: tetramethylsilane) δ(ppm) 1.70-1.90 (12H, m) 1.90-2.00 (12H, m) 3.95-4.30 (24H, m) 5.7.5-5.80 (6H, m) 6.05-6.20 (6H, m) 6.35-6.50 (6H, m) 6.90-7.00 (12H, m) 7.00-7.50 (16H, m) 8.10-8.25 (12H, m)

When a phase transition temperature of the thus-obtained m-23 was examined by a texture observation by a polarizing microscope, a transition of a crystal phase to an isotropic liquid phase occurred at around 100° C., while elevating a temperature. Then, when the temperature was gradually reduced from 110° C., a transition of the isotropic liquid phase to a nematic phase occurred at around 95° C. When the temperature was down to room temperature, it was shifted again to the crystal phase. In other words, it was found that, at the time of reducing temperature, m-23 exhibits the nematic phase in the range of from 95° C. to room temperature.

A m-23 (containing 0.1% by weight of hydroquinone monomethyl ether) was injected into a horizontal alignment cell having a cell gap of 5 μm (KSRP-05/A107M1NSS(ZZ); available from K.K. EHC) at 120° C. and subjected to be homogeneously aligned at 80° C. In the thus-established state, an angle dependence of retardation was measured. When the value of (nx−nz)/(nx−ny) was obtained, it was from 1.0 to less than 1.1 and, accordingly, it was found that m-23 exhibits a liquid crystal phase satisfying the numerical formula (I).

EXAMPLE 16

(Synthesis of TO-3)

TO-3 was prepared in accordance with the following scheme:

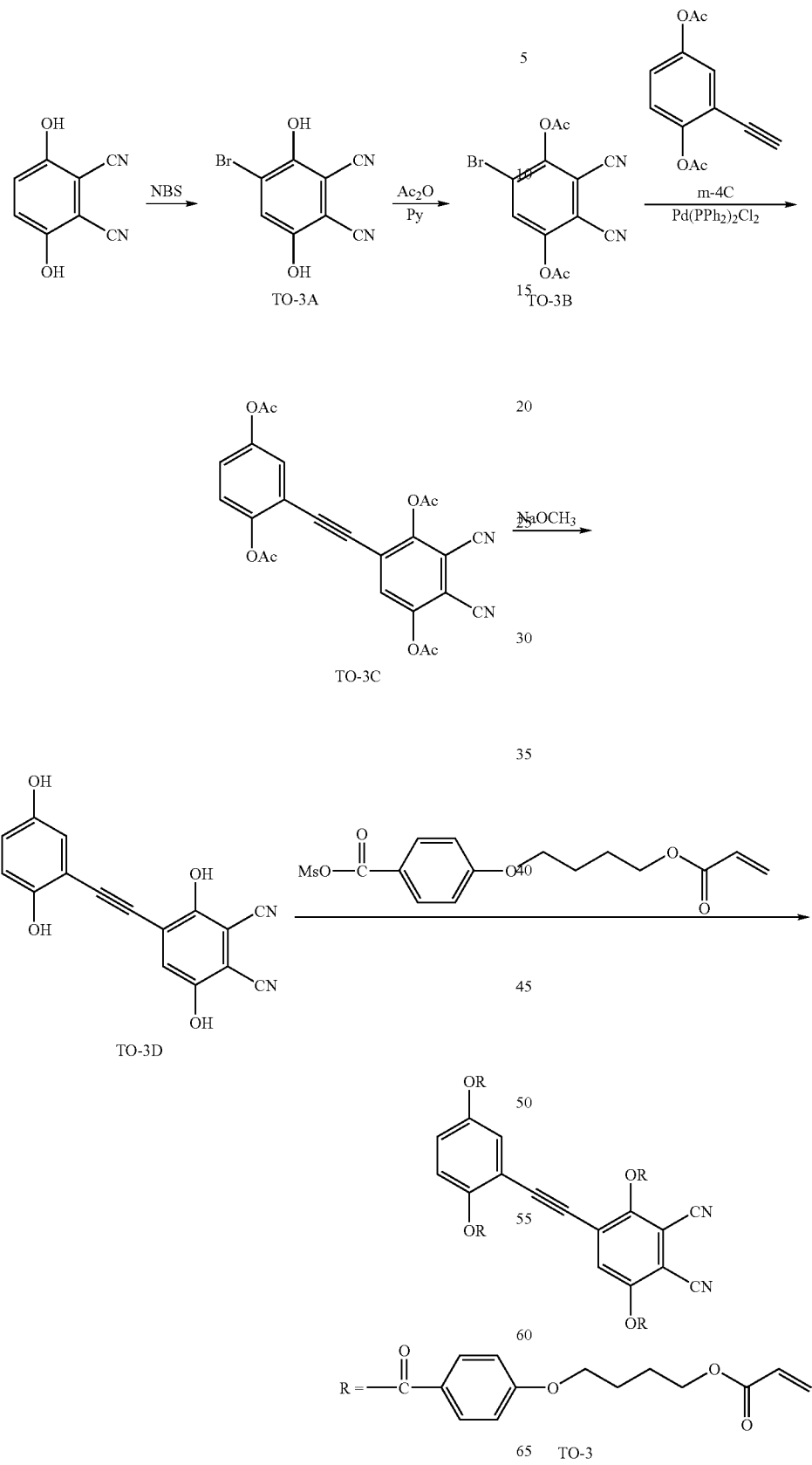

(Synthesis of TO-3A)

20.4 g of 2,3-dicyanohydroquinone was dissolved in 150 ml of t-butanol and, then, added with 22.6 g of NBS(N-bromosuccinimide) and, thereafter, stirred for 4 hours at room temperature. The resultant liquid was added with 1 L of water to precipitate a crystal. The thus-precipitated crystal was removed by filtering. The resultant filtrate was added with concentrated hydrochloric acid and, then, subjected to an extraction treatment by using ethyl acetate. The resultant extracted organic layer was concentrated under reduced pressure and, then, purified by using a column chromatography, to thereby obtain 8.5 g of TO-3A.

(Synthesis of TO-3B)

8.0 g of TO-3A was dissolved in 50 ml of tetrahydrofuran and, then, added with 25 ml of pyridine (Py) and 20 ml of acetic acid anhydrous ($Ac_2O$) in a dropping manner and, thereafter, stirred for 12 hours. The resultant reaction solution was added with 1 L of water to precipitate a crystal. The thus-precipitated crystal was collected by filtering and, the, dried. The thus-obtained crystal was purified by using a column chromatography, to thereby obtain 9.7 g of TO-3B.

(Synthesis of TO-3C)

3.0 g of TO-3B, 2.43 g of m-4C which had been obtained in accordance with Example 13, 60 mg of triphenylsulfine, 30 mg of bis(triphenylphosphine)palladium(II) dichloride and 10 mg of copper(I) iodide were dissolved in 100 ml of triethylamine and, then, heated for 5 hours at 60° C. under a nitrogen atmosphere and, thereafter, cooled. The resultant reaction solution was added with methanol to precipitate a crystal. The thus-precipitated crystal was collected by filtering and, then, dried. The thus-obtained crystal was purified by using a column chromatography, to thereby obtain 1.7 g of TO-3C.

(Synthesis of TO-3D)

1.7 g of TO-3C was dissolved in 40 ml of tetrahydrofuran and, then, added with 5 ml of sodium methoxide (28 methanol solution) and 20 ml of methanol. The resultant mixture was stirred for 30 minutes at room temperature and, then, added with diluted hydrochloric acid and, thereafter, subjected to an extraction treatment by using ethyl acetate. The resultant extracted organic layer was subjected to a distillation treatment under reduced pressure, to thereby obtain 1.0 g of TO-3D.

(Synthesis of TO-3)

0.43 g of methane sulfonylchloride was dissolved in 10 ml of tetrahydrofuran and cooled down to 0° C. The resultant solution was added with 1.0 g of 4-(4-acryloyloxybutyloxy) benzoic acid and 10 ml of a tetrahydrofuran solution of 0.51 g of diisopropylethylamine in a dropping manner and, then, stirred for 1 hour at 0° C. and, thereafter, added with 0.51 g of diisopropylamine and 0.02 g of 4-dimethylaminopyridine and, subsequently, added with 10 ml of a tetrahydrofuran solution of 0.14 g of TO-3D and, then, stirred for 12 hours at room temperature. The resultant reaction solution was added with water and, then, subjected to an extraction treatment by using $CH_2Cl_2$. The resultant extracted article was concentrated under reduced pressure and, then, purified by using a column chromatography, to thereby obtain 0.32 g of a crystal of TO-3. An NMR spectrum of the thus-obtained TO-3 was as follows:

$^1$H-NMR (solvent: $CDCl_3$, standard: tetramethylsilane) 67(ppm) 1.70-1.90 (8H, m) 1.90-2.00 (8H, m) 3.90-4.00 (4H, m) 4.08-4.18 (4H, m) 4.19-4.30 (8H, m) 5.80-5.90 (4H, m) 6.07-6.20 (4H, m) 6.36-6.48 (4H, m) 6.90-7.05 (9H, m) 7.25 (1H, dd) 7.32 (1H, d) 7.47 (1H, d) 8.06-8.20 (8H, m)

When a phase transition temperature of the thus-obtained TO-3 was examined by a texture observation by a polarizing microscope, a transition of a crystal phase to a nematic liquid crystal phase occurred at around 122° C., while elevating a temperature. Then, when the temperature was over 195° C., a transition of the nematic liquid crystal phase to a isotropic liquid phase occurred. In other words, it was found that TO-3 exhibits the nematic liquid crystal phase in the range of from 122° C. to 195° C.

TO-3 (containing 0.1% by weight of hydroquinone monomethyl ether) was injected into a horizontal alignment cell having a cell gap of 5 μm (KSRP-05/A107M1NSS(ZZ); available from K.K. EHC) at 130° C. and subjected to be homogeneously aligned at 130° C. In the thus-established state, an angle dependence of retardation was measured. When the value of (nx−nz)/(nx−ny) was obtained, it was from 1.0 to less than 1.1 and, accordingly, it was found that TO-3 exhibits a liquid crystal phase satisfying the numerical formula (I).

The present application claims foreign priority based on Japanese Patent Application Nos. JP2003-276042, JP2003-330969 and JP2004-135438, filed Jul. 17 of 2003, Sep. 24 of 2003 and Apr. 30 of 2004, respectively the contents of which is incorporated herein by reference.

What is claimed is:

1. A liquid crystalline composition, which comprises:
a liquid crystalline composition R which exhibits a liquid crystal phase having a positive birefringence; and
a liquid crystalline composition D which exhibits a liquid crystal phase having a negative birefringence,
wherein the liquid crystalline composition D comprises a compound represented by the following formula (D-2):

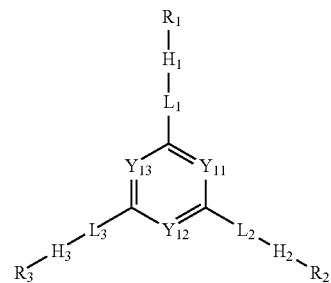

wherein $Y_{11}$, $Y_{12}$ and $Y_{13}$ each independently represent a methine group or a nitrogen atom;
$H_1$, $H_2$ and $H_3$ each independently represent a divalent 5-membered cyclic group;
$L_1$, $L_2$ and $L_3$ each independently represent a single bond or a divalent linking group;
$R_1$, $R_2$ and $R_3$ each independently represent an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, an alkylsulfonylamino group, an arylsulfonylamino group, a sulfamoyl group, a carbamoyl group, an alkylthio group, an arylthio group, an alkylsulfonyl group, an arylsulfonyl group, an alkylsulfinyl group, an arylsulfinyl group, an ureido group, a phosphoric acid amido group, a hydroxyl group, a mercapto group, a halogen atom, a cyano group, a sulfo group, a carboxyl group, a nitro group, a hydroxamic acid group, a sulfino group, a hydrazino group, an imino group, a heterocyclic group or a silyl group.

2. The liquid crystalline composition according to claim 1, wherein the formula (D-2) is represented by the following formula (I):

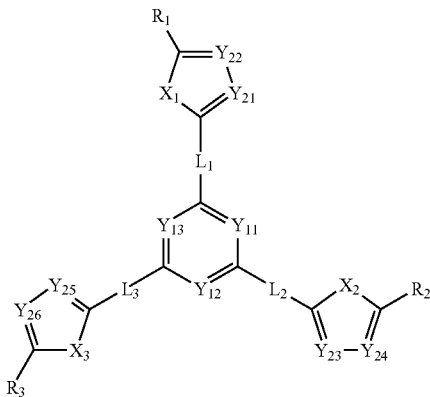

wherein $Y_{11}$, $Y_{12}$, $Y_{13}$, $L_1$, $L_2$, $L_3$, $R_1$, $R_2$ and $R_3$ are identical to those as defined in the formula (D-2);

$Y_{21}$, $Y_{22}$, $Y_{23}$, $Y_{24}$, $Y_{25}$ and $Y_{26}$ each independently represent a methine group or a nitrogen atom;

$X_1$, $X_2$ and $X_3$ each independently represent an oxygen atom, a sulfur atom, a methylene group or an imino group.

3. The liquid crystalline composition according to claim 1, wherein the liquid crystalline composition R comprises a compound having a rectangular plate-like shape.

4. The liquid crystalline composition according to claim 3, wherein the compound having the rectangular plate-like shape has at least two core moieties each of which has liquid crystallinity, the at least two core moieties being linked by at least one covalent bond to form the rectangular plate-like shape.

5. The liquid crystalline composition according to claim 3, wherein the compound having the rectangular plate-like shape is a liquid crystalline compound represented by the following formula (R-I):

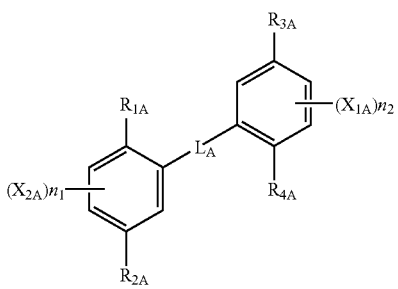

wherein $L_A$ represents —=— or —=—=—;

$X_{1A}$ and $X_{2A}$ each independently represent a halogen atom, a carboxyl group, a hydroxyl group, a cyano group, a nitro group, an alkyl group or an alkyloxy group;

$n_1$ and $n_2$ each independently represent an integer of from 0 to 3; and $R_{1A}$, $R_{2A}$, $R_{3A}$ and $R_{4A}$ are each independently represented by the following formula (R-IA):

*-($L_{1A}$-divalent cyclic group)$_p$-$L_{2A}$-divalent chain group-$Q_{1A}$, wherein * denotes a position to be bonded to the benzene ring in the formula (R-I);

$L_{1A}$ and $L_{2A}$ each independently represent a single bond or a divalent linking group;

the divalent cyclic group is a divalent linking group having at least one cyclic structure;

the divalent chain group is an alkylene group, a substituted alkylene group, an alkenylene group, a substituted alkenylene group, an alkynylene group or a substituted alkynylene group, wherein the —CH$_2$— group in the alkylene group and the substituted alkylene group may be substituted with one of —O— or —S—, and when the alkenylene group, the substituted alkenylene group, the alkynylene group or the substituted alkynylene group contains —CH$_2$— group, the —CH$_2$— group may be substituted with one of —O— or —S—;

$Q_{1A}$ represents a polymerizable group; and p represents an integer of from 0 to 3.

6. A liquid crystalline composition, which comprises:
a liquid crystalline composition R which exhibits a liquid crystal phase having a positive birefringence; and
a liquid crystalline composition D which exhibits a liquid crystal phase having a negative birefringence,
wherein the liquid crystalline composition exhibits a liquid crystal phase in a mixed state of the liquid crystalline composition R and the liquid crystalline composition D, at any mixing ratio of the liquid crystalline composition R to the liquid crystalline composition D, and
wherein the liquid crystalline composition D comprises a compound represented by the following formula (D-2):

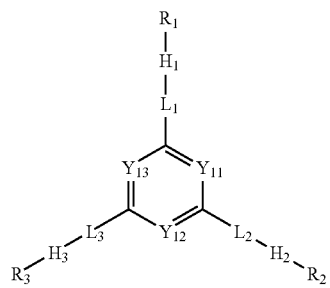

wherein $Y_{11}$, $Y_{12}$ and $Y_{13}$ each independently represent a methine group or a nitrogen atom;

$H_1$, $H_2$ and $H_3$ each independently represent a divalent 5-membered cyclic group;

$L_1$, $L_2$ and $L_3$ each independently represent a single bond or a divalent linking group;

$R_1$, $R_2$ and $R_3$ each independently represent an alkyl group, an alkenyl group, an alkynyl group, an aryl group, an amino group, an alkoxy group, an aryloxy group, an acyl group, an alkoxycarbonyl group, an aryloxycarbonyl group, an acyloxy group, an acylamino group, an alkoxycarbonylamino group, an aryloxycarbonylamino group, an alkylsulfonylamino group, an arylsulfonylamino group, a sulfamoyl group, a carbamoyl group, an alkylthio group, an arylthio group, an alkylsulfonyl group, an arylsulfonyl group, an alkylsulfinyl group, an arylsulfinyl group, an ureido group, a phosphoric acid amido group, a hydroxyl group, a mercapto group, a halogen atom, a cyano group, a sulfo group, a carboxyl group, a nitro group, a hydroxamic acid group, a sulfino group, a hydrazino group, an imino group, a heterocyclic group or a silyl group.

7. The liquid crystalline composition according to claim 1, wherein the liquid crystal phase having the positive birefringence is a nematic phase.

8. The liquid crystalline composition according to claim 1, wherein the liquid crystal phase having the negative birefringence is a discotic nematic phase.

9. The liquid crystalline composition according to claim 1, which exhibits a liquid crystal phase at a temperature of from 20° C. to 300° C.

10. The liquid crystalline composition according to claim 1, which exhibits a liquid crystal phase satisfying the following numerical formula (III):

$$1.1 \leq (nx-nz)/(nx-ny) \leq 20,$$

wherein nx, ny and nz represent refractive indices in three perpendicular directions to each other in the liquid crystal phase, while nx denotes a largest refractive index and nz denotes a smallest refractive index.

11. A retardation film comprising: a transparent support; and at least one optically anisotropic layer formed from a liquid crystalline composition according to claim 1.

12. An elliptically polarizing film comprising: a retardation film according to claim 11 and a polarizing film.

13. A liquid crystalline compound represented by the following formula (II):

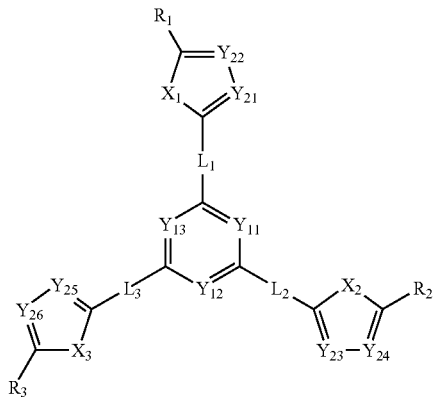

wherein $Y_{11}$, $Y_{12}$, $Y_{13}$, $Y_{21}$, $Y_{22}$, $Y_{23}$, $Y_{24}$, $Y_{25}$ and $Y_{26}$ each independently represent a methine group or a nitrogen atom;

$X_1$, $X_2$ and $X_3$ each independently represent an oxygen atom, a sulfur atom, a methylene group or an imino group;

$L_1$, $L_2$ and $L_3$ each independently represent a single bond or a divalent linking group;

$R_1$, $R_2$ and $R_3$ each independently represent the following formula (V):

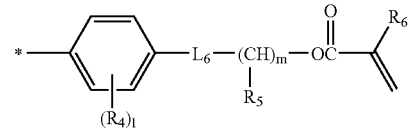

wherein * denotes a position to be bonded to the 5-membered ring in the formula (II);

$R_4$ represents a halogen atom, an alkyl group having from 1 to 8 carbon atoms, an alkyloxy group having from 2 to 8 carbon atoms, an alkoxycarbonyl group having from 2 to 8 carbon atoms, a nitro group or a cyano group;

l represents an integer of from 0 to 4;

$L_6$ represents at least one group selected from the group consisting of —O—, —CO—O, —O—CO—, —O—CO—O and —CH$_2$—, wherein  denotes a position to be bonded to the benzene ring in the formula (V);

$R_5$ represents a hydrogen atom, a methyl group, an ethyl group or a propyl group;

m represents an integer of from 2 to 16; and $R_6$ represents a hydrogen atom or a methyl group.

14. The liquid crystalline composition according to claim 6, wherein the liquid crystal phase having the positive birefringence is a nematic phase.

15. The liquid crystalline composition according to claim 6, wherein the liquid crystal phase having the negative birefringence is a discotic nematic phase.

16. The liquid crystalline composition according to claim 6, which exhibits a liquid crystal phase at a temperature of from 20° C. to 300° C.

17. The liquid crystalline composition according to claim 6, which exhibits a liquid crystal phase satisfying the following numerical formula (III):

$$1.1 \leq (nx-nz)/(nx-ny) \leq 20,$$

wherein nx, ny and nz represent refractive indices in three perpendicular directions to each other in the liquid crystal phase, while nx denotes a largest refractive index and nz denotes a smallest refractive index.

18. A retardation film comprising: a transparent support; and at least one optically anisotropic layer formed from a liquid crystalline composition according claim 6.

* * * * *